United States Patent
Isken et al.

(10) Patent No.: US 12,203,868 B2
(45) Date of Patent: Jan. 21, 2025

(54) QUALITATIVE OR QUANTITATIVE CHARACTERIZATION OF A COATING SURFACE

(71) Applicant: EVONIK OPERATIONS GMBH, Essen (DE)

(72) Inventors: Philipp Isken, Altenberge (DE); Sandra Bittorf, Witten (DE); Oliver Kroehl, Cologne (DE); Claudia Bramlage, Essen (DE); Markus Vogel, Kamp-Lintfort (DE); Stefan Silber, Krefeld (DE); Gaetano Blanda, Haltern am See (DE); Olivia Lewis, Berlin (DE); Daniel Haake, Potsdam (DE)

(73) Assignee: EVONIK OPERATIONS GMBH, Essen (DE)

( * ) Notice: Subject to any disclaimer, the term of this patent is extended or adjusted under 35 U.S.C. 154(b) by 625 days.

(21) Appl. No.: 17/477,025

(22) Filed: Sep. 16, 2021

(65) Prior Publication Data
US 2022/0084181 A1    Mar. 17, 2022

(30) Foreign Application Priority Data
Sep. 17, 2020   (EP) .................................... 20196660

(51) Int. Cl.
*G06K 9/00* (2022.01)
*B25J 9/16* (2006.01)
(Continued)

(52) U.S. Cl.
CPC ........ *G01N 21/8851* (2013.01); *B25J 9/1697* (2013.01); *G01N 21/8422* (2013.01);
(Continued)

(58) Field of Classification Search
None
See application file for complete search history.

(56) References Cited

U.S. PATENT DOCUMENTS 6,088,116 A    7/2000 Pfanstiehl
6,462,813 B1   10/2002 Haven et al.
(Continued)

FOREIGN PATENT DOCUMENTS

CN   111444617 A   7/2020
EP   2602763 A1   6/2013
(Continued)

OTHER PUBLICATIONS

Wang et al., "Virtual-reality-based point-and-direct robotic inspection in manufacturing," in IEEE Transactions on Robotics and Automation, vol. 12, No. 4, pp. 516-531, Aug. 1996. (Year: 1996).*
(Continued)

*Primary Examiner* — Feng Niu
(74) *Attorney, Agent, or Firm* — PERRY + CURRIER INC.

(57) ABSTRACT

A method for qualitative and/or quantitative characterization of a coating surface is provided, comprising:
  providing a program recognizing coating surface defect types;
  determining, by the program, whether a camera(s) coupled to the program is within a predefined distance range and/or within a predefined image acquisition angle range relative to a currently presented coating surface;
  depending on the determination:
    generating a feedback signal indicative of whether adjustment of the position of the camera(s) is within predefined distance range and/or within the predefined image acquisition angle range; and/or
    automatically adjusting the relative distance of the camera and and/or automatically adjusting the angle of the camera;
(Continued)

enabling the camera to acquire an image of the coating surface only when the camera(s) is/are within the predefined distance range and/or image acquisition angle range;

processing the digital image for recognizing coating surface defects; and outputting a characterization of the coating surface.

15 Claims, 12 Drawing Sheets

(51) Int. Cl.
| | |
|---|---|
| *G01N 21/84* | (2006.01) |
| *G01N 21/88* | (2006.01) |
| *G05B 19/418* | (2006.01) |
| *G06F 16/51* | (2019.01) |
| *G06N 20/00* | (2019.01) |
| *G06T 7/00* | (2017.01) |
| *G06T 7/11* | (2017.01) |
| *G16C 60/00* | (2019.01) |
| *G16C 20/30* | (2019.01) |
| *G16C 20/70* | (2019.01) |

(52) U.S. Cl.
CPC ... *G01N 21/8806* (2013.01); *G05B 19/41875* (2013.01); *G06F 16/51* (2019.01); *G06N 20/00* (2019.01); *G06T 7/0004* (2013.01); *G06T 7/001* (2013.01); *G06T 7/11* (2017.01); *G16C 60/00* (2019.02); *G01N 2021/8427* (2013.01); *G01N 2021/8854* (2013.01); *G01N 2021/8861* (2013.01); *G01N 2021/8864* (2013.01); *G01N 2021/8874* (2013.01); *G01N 2021/888* (2013.01); *G01N 2021/8887* (2013.01); *G05B 2219/37206* (2013.01); *G05B 2219/37451* (2013.01); *G05B 2219/45013* (2013.01); *G06T 2207/20081* (2013.01); *G06T 2207/20084* (2013.01); *G06T 2207/30108* (2013.01); *G06T 2207/30156* (2013.01); *G16C 20/30* (2019.02); *G16C 20/70* (2019.02); *Y02P 90/02* (2015.11)

(56) References Cited

U.S. PATENT DOCUMENTS

| | | | |
|---|---|---|---|
| 6,542,248 B1 | 4/2003 | Schwarz | |
| 9,007,458 B2* | 4/2015 | Terreno | G06T 7/136 |
| | | | 348/128 |
| 10,240,982 B2 | 3/2019 | Shimada | |
| 10,473,594 B2* | 11/2019 | Heikkilä | H04N 23/90 |
| 10,533,849 B2* | 1/2020 | Sano | G01N 21/94 |
| 10,726,543 B2* | 7/2020 | Bian | G01N 21/8851 |
| 11,024,020 B2* | 6/2021 | de Bonfim Gripp | G06V 10/82 |
| 11,131,635 B2 | 9/2021 | Gupta et al. | |
| 11,270,110 B2* | 3/2022 | Kadambi | G01B 11/24 |
| 11,373,418 B2* | 6/2022 | Motoyama | G06T 7/20 |
| 11,494,891 B2* | 11/2022 | Sohn | G06V 10/82 |
| 11,747,206 B2* | 9/2023 | Paredes | G01J 3/0272 |
| | | | 356/402 |
| 2004/0252308 A1 | 12/2004 | Prakash et al. | |
| 2012/0026512 A1 | 2/2012 | Schwarz | |
| 2013/0147947 A1* | 6/2013 | Terreno | G06T 7/11 |
| | | | 348/135 |
| 2017/0069075 A1 | 3/2017 | Okuda | |
| 2017/0069076 A1 | 3/2017 | Yoshimuta | |
| 2017/0148102 A1* | 5/2017 | Franke | G06Q 30/0601 |
| 2018/0017501 A1* | 1/2018 | Trenholm | G01R 31/308 |
| 2018/0038805 A1* | 2/2018 | Heikkilä | G01S 17/06 |
| 2019/0080446 A1* | 3/2019 | Kuzmin | G06V 30/144 |
| 2019/0287237 A1 | 9/2019 | de Bonfim Gripp et al. | |
| 2019/0331483 A1* | 10/2019 | Sano | G01N 21/94 |
| 2020/0166909 A1 | 5/2020 | Noone et al. | |
| 2020/0167905 A1* | 5/2020 | Bian | G01N 21/91 |
| 2020/0210635 A1 | 7/2020 | Washburn et al. | |
| 2020/0257933 A1 | 8/2020 | Steingrimsson et al. | |
| 2020/0272834 A1* | 8/2020 | Motoyama | G06F 18/251 |
| 2021/0201472 A1* | 7/2021 | Sohn | G06V 10/82 |
| 2021/0264147 A1* | 8/2021 | Kadambi | G06F 18/2413 |
| 2021/0356404 A1 | 11/2021 | Safai | |
| 2022/0082508 A1 | 3/2022 | Isken et al. | |
| 2022/0113193 A1* | 4/2022 | Paredes | G01J 3/0272 |
| 2023/0360196 A1* | 11/2023 | Martins Loureiro | G06T 7/0004 |

FOREIGN PATENT DOCUMENTS

| | | |
|---|---|---|
| KR | 20190032908 A | 3/2019 |
| WO | WO-2018208360 A2 | 11/2018 |
| WO | WO-2018208360 A3 | 11/2018 |
| WO | WO-2019159425 A1 * | 8/2019 |
| WO | WO-2019171498 A1 | 9/2019 |

OTHER PUBLICATIONS

Ghorai et al., "Automatic Defect Detection on Hot-Rolled Flat Steel Products," in IEEE Transactions on Instrumentation and Measurement, vol. 62, No. 3, pp. 612-621, Mar. 2013. (Year: 2013).*

Ebayyeh et al., "A Review and Analysis of Automatic Optical Inspection and Quality Monitoring Methods in Electronics Industry," in IEEE Access, vol. 8, pp. 183192-183271, 2020 (Year: 2020).*

Luo et al., "Automated Visual Defect Detection for Flat Steel Surface: A Survey," in IEEE Transactions on Instrumentation and Measurement, vol. 69, No. 3, pp. 626-644, Mar. 2020 (Year: 2020).*

Liu et al., "Automated construction quality assessment: A review," 2015 10th International Symposium on Mechatronics and its Applications (ISMA), Sharjah, United Arab Emirates, 2015, pp. 1-6. (Year: 2016).*

Khalaj, Gholamreza. "Artificial neural network to predict the effects of coating parameters on layer thickness of chromium carbonitride coating on pre-nitrided steels." Neural Computing and Applications 23.3 (2013): 779-786.

Li, Junchen, et al. "A review on high entropy alloys coatings: fabrication processes and property assessment." Advanced Engineering Materials 21.8 (2019): 1900343.

Tatlier, Melkon, et al. "Coatings of Na-aluminosilicate zeolites prepared using predictions from an artificial neural network method." Journal of Porous Materials 15.4 (2008): 389-395.

* cited by examiner

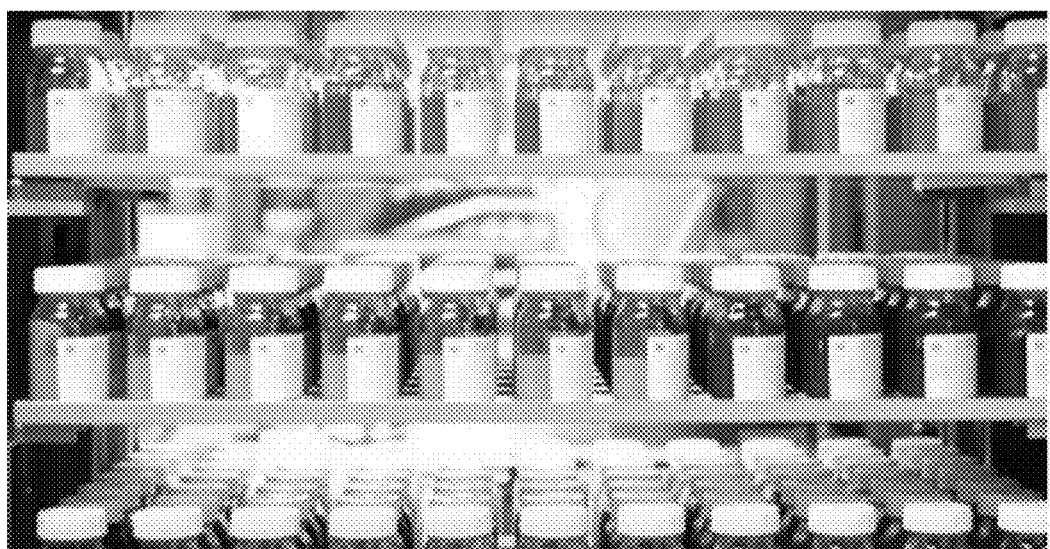
Fig. 8A
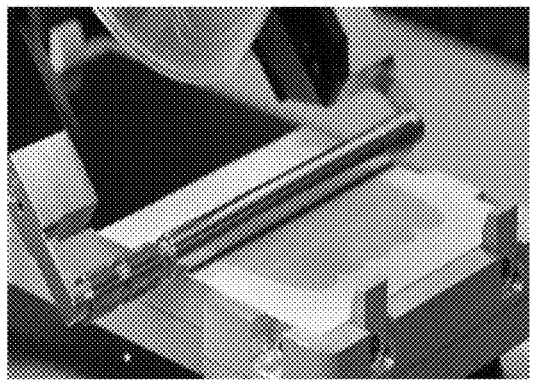 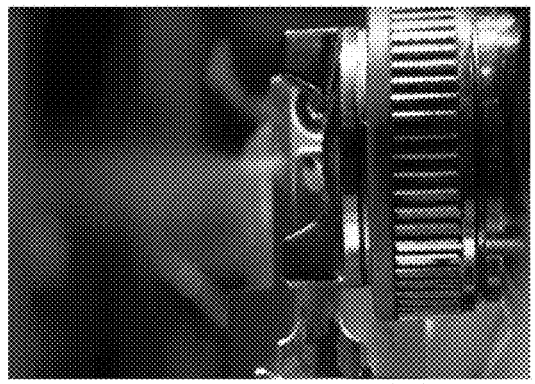
Fig. 8B    Fig. 8C
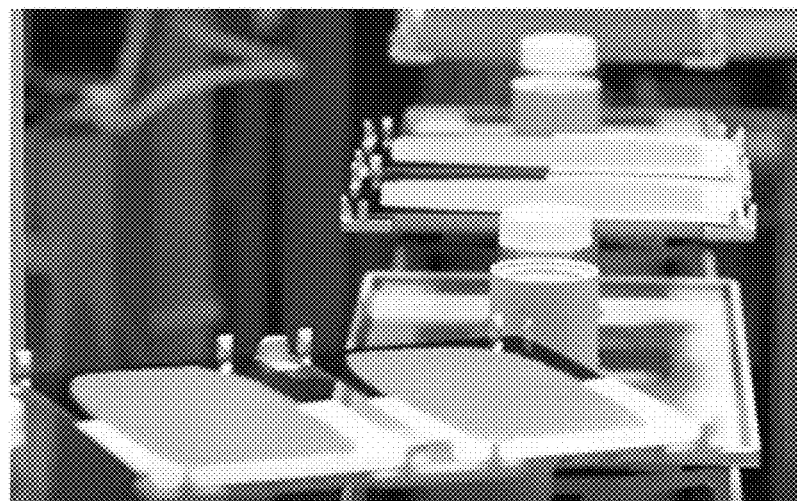
Fig. 8D

QUALITATIVE OR QUANTITATIVE CHARACTERIZATION OF A COATING SURFACE

TECHNICAL FIELD

The invention relates to the identification of coating defects and to the characterization of coating surfaces, in particular coating surfaces based on coating compositions for paints, varnishes, printing inks, grinding resins, pigment concentrates or other coating compositions.

BACKGROUND

Paint and varnish coatings can have a variety of defects that negatively influence the appearance or technical properties of the coated object. The coating defects can be, for example, foam, craters, clouding, levelling problems, corrosion, wetting problems, floating of pigments (floating), sagging, agglomeration, or bubble formation, whereby several defects can occur simultaneously and can influence each other. To investigate and avoid these problems, test substrates are coated with the formulation during formulation development and examined for defects. Depending on the intended field of application, different substrates are used, for example wood, plastic, paper/cardboard, glass, or metal. Furthermore, different pretreatments of the substrate are possible, and the pretreatments may further complicate matters. Due to the number of interdependent process parameters, large number of coating compositions, pretreatment approaches and substrate types, it is currently impossible to predict whether or not a particular coating composition will provide a coating of acceptable quality if applied on a particular substrate. Therefore, the coating surface quality can currently only be determined retrospectively.

Currently, the defects are assessed visually by a human being, e.g. an employee. This purely visual assessment is typically very coarse-grained, highly subjective and hardly reproducible. As a consequence, the identification of defects and the assessment of the quality of the coating surface may require a great deal of experience on the part of the employee but may nevertheless vary strongly from person to person which makes it difficult to compare the results. In addition, the manual evaluation of coating surfaces is time-consuming and hence expensive.

SUMMARY

The invention aims at providing an improved method and corresponding system for the characterization of surface defects in a coating surface and to the use of the resulting programs and information in the context of the manufacturing of coating compositions as specified in the independent claims. Embodiments are given in the dependent claims. Embodiments of the present invention may be freely combined with each other, provided they are not mutually exclusive.

In one aspect, the invention relates to a method for qualitative and/or quantitative characterization of a coating surface. The method comprises:
  processing a digital image of the coating surface by a defect-identification program, the defect-identification program being configured to recognize types of coating surface defects, e.g. by recognizing patterns, each pattern representing one of the coating surface defect types; and
  outputting a characterization of the coating surface, the characterization being computed as a function of coating surface defects recognized by the defect-identification program.

Embodiments of the invention may have the advantage that a characterization of coating surface is provided by means of a defect-identification program and hence in a reproducible, objective and fast manner.

For example, the output characterization may indicate that the coating surface is free of a defect type D1 but may comprise defects of defect type D2 and D3. The output may also indicate that the coating surface is free of any coating defect. According to other examples, the output may be more concrete and in addition indicate the amount or extent of the coating defect, e.g. by indicating that the surface comprises a minor defect of type D2 and a severe defect of type D3. In other examples, the characterization can comprise a numerical characterization of the extent of the defects and/or an indication of individual pixels in the digital image showing a particular type of defect or belonging to a particular instance of a particular defect type.

Embodiments of the invention may have the advantage that the occurrence and/or locations of defects in a coating surface are detected fully automatically and used for automatically computing a characterization of the coating surface in dependence on the type and/or extent of the one or more defects identified in the image analysis procedure. Hence, a large number of digital images can be evaluated and annotated with the computed characterization of the respectively depicted coating surface fully automatically. This may be particularly useful in the context of a high throughput facility for testing and/or manufacturing coating compositions. The automated determination of the coating surface characterization increases the transparency and reproducibility of the assessment of the quality and other properties of the coating surface.

Embodiments of the invention may have the further advantage that the automatically identified coating surface defects and the characterization of the coating surface derived therefrom can be used as databases for performing many different forms of data analysis. In particular, the computed characterizations can be used as a qualitative and/or quantitative indicator of the quality of a coating surface and of the quality of the coating composition, the quality or suitability of the coating composition manufacturing process and/or the quality or suitability of the coating application process (including a pre-treatment process of the surface, if any, the substrate type and/or the application equipment) used for manufacturing the coating composition and the coating surface.

The automated computation of qualitative and/or quantitative coating surface characterizations may enable an automated analysis of large amounts of data and may ensure comparability of the surface quality characterizations associated with different coating compositions, coating manufacturing process parameters, and/or coating application process parameters. This is particularly useful in the context of producing and testing many different varieties of a coating composition to identify the optimum coating composition for a substrate or use case scenario.

Embodiments of the invention may be advantageous in particular in the context of the production of paints, varnishes, printing inks, grinding resins, pigment concentrates and other coating materials, since a reproducible, objective characterization of surface properties of respective coating surfaces was previously not available. A prediction of the coating surface quality was not possible due to the subjectivity of manual descriptions of the coating surfaces and due to the large number of components and their interactions.

For example, foam is a phenomenon which frequently occurs during the manufacture and application of coatings and printing inks. The cause of foam is the introduction of gas into the liquid material. This can occur by:

mechanical introduction of air during manufacture by stirring and mixing
displacement of air during wetting of pigments and fillers
mechanical introduction of air during applications such as rolling, spraying, printing
displacement of air when coating porous substrates.

Dried foam leaves surface defects (e.g. bubble defects) in the paint film. The foam not only affects the visual appearance, it also reduces the protective function of the coating. Virtually all the components in the coating formulation can influence foaming behavior positively or negatively. The substrate and method of application also have an impact on foaming behavior. Therefore, a defoamer typically is a necessary component in the formulation of a coating composition.

Applicant has observed that the effectiveness of the defoamer of a coating composition depends on its partial incompatibility in the coating medium. This permits formation of defoamer droplets in the system, without causing film or surface defects due to excessive incompatibility. Thus, a key feature of all defoamers is their targeted and controlled incompatibility with the medium that is to be defoamed. A defoamer that is too compatible does not migrate into the foam lamella specifically, it is present in the entire coating film. The defoaming effect is then either low or non-existent. Too much incompatibility causes problematic coating defects such as turbidity or cratering. Choosing the correct defoamer is therefore a kind of "balancing act" between compatibility and incompatibility. Defoaming is thus always a compromise between efficiency and compatibility.

As a result of the multitude of different coating systems, there is no "one" defoamer that is optimally suited to all formulations. To ensure that a suitable product can be provided for any purpose, a range of defoamers is required. The defoaming effect can be finely adjusted by varying the dosage: In general, better defoaming is achieved the more defoamer is used. However, this may also increase the defects (e.g. cratering) or rather these may become more visible. Cratering defects are defects resulting from the incompatibility of components which may be caused e.g. by too much defoamer and/or the wrong defoamer. Reducing the dosage of the defoamer prevents film defects, though the defoaming effect may, in some circumstances, not be sufficient. Furthermore, applicant has observed that in some coating compositions, increasing the amount of the defoamer(s) above a certain amount may actually decrease the defoaming effect. Hence, identifying one or more defoamers which provide a coating surface with no or minimal defects is a highly complex task.

According to embodiments of the invention, the coating composition used for generating the coating surface comprises a combination of two or more different defoamers whose type and amount was chosen such that a compromise between defoaming efficiency and compatibility/mixability with other components of the composition is achieved.

Hence, the selection of the type and amount of the one or more defoamers in a coating composition is a highly complex task. The situation is further complicated by the fact that the type and amount of the selected defoamer(s) interrelates with the type and amounts of other components of the coating composition, with the coating manufacturing process parameters and/or the coating application process parameters. Minor changes in one of these parameters may have a strong effect on the type and extent of surface defects observed in a respective coating surface. A manual characterization of the quality of a coating surface has so far been a major obstacle in the identification of changes in respect to the coating composition and associated process parameters that provide for an improvement in the coating surface qualities.

Applicant has observed that the automated detection of coating defects of particular defect types such as bubble defects and cratering defects may allow training a further machine learning model (e.g. the models M2, M3 described below for some embodiments of the invention) on data comprising various coating composition specifications associated with respectively observed coating defects in order to automatically compute and output a specification of an improved version of a coating composition (M3) or to compute and output coating surface characterizations, e.g. coating defects, that are expected for a given (complete or incomplete) coating composition (M2): for example, the machine learning model may learn during a training phase that bubbles on the coating surface are indicative of ineffectiveness of a defoamer and that cratering defects in the coating surface are an indication of incompatibility of the defoamer and the coating medium. In the first case, the model may suggest replacing the currently used defoamer by a defoamer being more effective. In the latter case, the model may suggest replacing and/or supplementing the currently used defoamer by/with a defoamer predicted to be more compatible with the coating medium. In case the coating composition already comprises an "effective" defoamer DF1 and a "compatible" defoamer DF2 in a particular ratio r=DF1:DF2, the model in the first case may suggest increasing the ratio and in the latter case suggest decreasing the ratio.

Hence, according to embodiments of the invention, the composition-specification prediction model is used for predicting a ratio of at least two different defoamers, in particular the ratio of a first defoamer with high defoaming effectiveness and low coating medium compatibility and a second defoamer with low defoaming effectiveness and high coating medium compatibility, whereby the ratio is predicted to minimize both the occurrence of bubble defects and cratering defects.

Other defects may be caused by another component and/or manufacture process parameters.

According to some embodiments, the characterizations of the coating surfaces output by the defect-identification program comprises fine-granular quantitative characterizations, e.g. a numerical value within a continuous scale or within a set of at least 10 different predefined numerical values or value ranges. The defect-identification program can be configured to transform the fine-granular quantitative characterizations into coarse-granular quantitative characterizations to make the automatically computed characterizations comparable to an existing, coarse-grained data set. For example, the existing, coarse-grained data set may have been created manually. The coarse-granular quantitative characterization can be a numerical value within a set of less than 10 different predefined numerical values or value ranges. The automated transformation may increase the data basis for various data analysis or machine learning purposes by proving a mix of manually labeled and automatically labeled digital images of coating surfaces which are comparable to each other.

According to other embodiments, the output of the defect identification program can be coarse-grained from the beginning. For example, the output can be a mere image classification output comprising image class labels such as "defect-free coating surface", "coating surface with (minor) bubble defects" or "coating surface with (minor) bubble defects and (severe) cratering defects.

According to embodiments, the method comprises calculating, by the defect-identification program, a measure for the recognized defects for computing the qualitative and/or quantitative characterization of the coating surface; and outputting the qualitative and/or quantitative characterization of the coating surface.

For example, a coating surface may comprise two or more defects of one or more different defect types and of varying extents. The calculated qualitative and/or quantitative measures of each of the defects can be used, e.g. aggregated, for obtaining a qualitative and/or quantitative characterization of the coating surface which integrates the automatically obtained measures of the automatically identified defects in the coating surface.

The identification of individual defects and the automated determination of the measures of the individual defects may have the advantage that the number, the type, the size and further properties of each individual defect in a coating surface is objectivized. Embodiments of the invention are much less subjective than prior art approaches based on manual/visual assessment of individual defects and/or coating surface qualities by the staff. The visual evaluation was not quantitative and only allowed a very rough classification of the results according to coarse-grained quality classes or a coarse-grained grading system.

According to embodiments, the measure of the defect is or comprises a quantitative measure selected from a group comprising: the area of the defect (in absolute terms or relative to the size of the coating surface depicted in the image), the number of bubbles, depressions or other defect-associated patterns observed in the image, the maximum, minimum and/or average size of the bubbles or depressions or other patterns representing a defect observed in the image.

In addition, or alternatively, the measure of the defect is or comprises a quantitative measure. The quantitative measure can in particular be the type of the defect identified. For example, the defect type can be selected from a group comprising a cratering defect, an abrasion defect, an adhesion failure defect, an alligatoring defect, a bleeding defect, a blistering defect, a bloom defect, a bridging defect, a bubbling defect, a cathodic disbanding defect, a checking defect, a cissing defect, a cobwebbing defect, a cracking defect, a crazing defect, a crowsfooting defect, a delamination defect, a fading defect, a flaking defect, a grinning defect, a heat defect, an impact defect, an intercoat contamination defect, a mud cracking defect, an orange peeling defect, a peeling defect, a pinholes defect, a rippled coating defect, a runs defect, a rust rashing defect, a rust spotting defect, a rust staining defect, a sags defect, a settlement defect, a skinning defect, a solvent lifting defect, a solvent popping defect, a stress cracking defect, an undercutting defect, a wrinkling defect.

According to embodiments, the method further comprises:
  determining at least one coating surface defect type to be identified;
  automatically determining one or more illumination angles and/or one or more image acquisition angles allowing the acquisition of a digital image that enables the defect identification program to compute the characterization of the coating surface depicted in the image in respect to the at least one determined defect type;
  positioning one or more light sources at the determined illumination angle relative to the coating surface; and/or
  positioning one or more cameras (preferably one camera) at the determined one or more image acquisition angles relative to the coating surface; and
  after the positioning of the light source(s), the camera(s) and the coating surface relative to each other, using the camera(s) for acquiring the digital image(s) of the coating surface.

In addition to or instead of positioning the light sources automatically, the defects-identification-program can be configured to generate a feedback signal indicating that and/or how adjustment of the positioning of the one or more light sources and the coating surface relative to each other can be adapted such that the illumination angle lies within the identified predefined illumination angle range.

The illumination angle and/or image acquisition angle suitable for detecting a surface defect may vary depending on the type of defect and/or the type of substrate used.

For example, for the detection of bubble defects, preferably a tilted illumination angle, e.g. an angle between >0° to 70°, in particular about 45°, and between 110° to <180°, in particular about 135°, can be used as this provides bubble-induced shadow formations with sufficient contrast.

The preferred image acquisition angle for detecting bubble defects can be any one of >0°-360°, preferably 0-180°, more preferred 10°-170°.

To the contrary, cratering defects in coating surfaces can be identified and characterized using a basically orthogonal image acquisition angle and an orthogonal (background) illumination angle. For example, for the detection of cratering defects, preferably an image acquisition angle between 70° to 110° can be used. For transparent substrates (e.g. glass or transparent plastic), a preferred illumination angle is between 250° to 290° and the one or more light sources are backlights (transmitted-light illuminator(s)) positioned such that the light emitted by the light sources passes the transparent substrate and the coating surface basically orthogonally before it is captured by the one or more cameras. The basically orthogonal illumination angle reduces light reflections and allows to determine the thickness of the coating at the bottom and the sides of the craters and/or the depth of the craters. For opaque substrates, other illumination angles between >0° and <180° may be used, preferably orthogonal illumination angles, e.g. illumination angles between 70° to 110°.

Embodiments of the invention which control the relative position of the one or more cameras, the one or more light sources and the coating surface as well as the illumination angle(s) and image acquisition angle(s) may have the advantage that the digital images to be provided as input to the defect-identification program are ensured to be taken from a perspective and under illumination conditions which are comparable and which allow to identify and characterize the depicted defects. In case the defect-identification program was obtained based on a machine learning approach, embodiments of the invention controlling the relative positions and the illumination angle(s) and image acquisition angle(s) may ensure that the conditions used for acquiring the digital image are similar to the conditions used for obtaining the training images from which the defect-identification program was derived. By exerting a tight control of the image acquisition process, embodiments may ensure that the acquired digital images are comparable and can be processed by the defect-identification program reproducibility and accurately.

According to embodiments, the processing of the digital image further comprises:
- performing, by the defect-identification program, a classification of the digital image in respect to the type and/or amount of surface defects depicted therein and/or a semantic segmentation of the image based on one or more surface defect types depicted therein and/or object detection and/or instance segmentation of the image, thereby automatically assigning one or more labels to the whole digital image, to image regions and/or to individual pixels, each label being indicative of the type of defect identified in the digital image; and
- outputting the one or more assigned labels.

According to some embodiments, the defect identification program (which may be based on publicly available programs such as Mask R-CNN and may in addition comprise one or more additional program modules or functions e.g. for generating a GUI, for exchanging data with a network, a database and/or a HTE or for performing further predictive tasks), is configured to perform image classification in respect to the type and/or amount of surface defects depicted therein and/or to perform a semantic segmentation of the image based on one or more surface defect types depicted therein and/or to perform object detection and/or instance segmentation of the image.

Different approaches can be used for creating different types of labels for different types defects and/or use case scenarios. In some examples, combinations of two or more labels of different types can be assigned to an image, image region or pixel.

For example, image classification is the process of classifying the digital image in respect to the type(s) of coating defects depicted therein. A class label may look like "surface free of defects", "surface with bubble defects" or "surface with severe bubble defects". A class label does not identify the position and number of individual defect instances.

Semantic segmentation is the process of identifying coating defects of one or more different defect types at the pixel level, whereby no information regarding the outline of individual defect instances is obtained. This means that the semantic segmentation provides information on the type and location of different defect types at the pixel level, but in case several defect instances of the same type overlap, they cannot be recognized as separate defect instances. A coating defect semantic label may look like "bubble defect(s) identified at pixels {xy coordinates of all pixels in the digital image depicting a bubble defect}" or "cratering defect(s) identified at pixels {xy coordinates of all pixels in the digital image depicting a cratering defect}". A coating defect semantic label identifies the location of one or more defect types identified in the image at the pixel level and hence allows a rough quantification of the extent of the defect. A defect type semantic label may have the advantage of providing sufficiently detailed information for identifying the location and extent of one or more different defect types but may not allow identifying individual defect instances.

"Object detection" in this context is the process of identifying coating defect instances of one or more different defect types and their approximate location in the digital image. A coating defect object label may look like "bubble defect instance #234 at pixels {xy coordinates of a (typically rectangular) bounding box comprising this bubble defect instance #234}" or "bubble defect instance #554 at pixels {xy coordinates of a (typically rectangular) bounding box comprising this bubble defect instance #554}". A coating defect object label identifies individual instances of one or more defect types identified in the image and also identifies the rough positions of these defect instances in the image not at the pixel level, but at the level of bounding boxes. The coating defect instance labels can be graphically represented in the form of a digital image in which bounding boxes predicted to comprise an identified defect type instance are highlighted. Defect type object labels may have the advantage of providing a large amount of detailed information which allow a quantification of a given defect type and counting defect type instances. That the positional information is based on coarse grained bounding boxes may ease the storing and processing of those labels.

Defect instance segmentation is the process of identifying coating defect instances of one or more different defect types and their respective location in the image at the pixel level. A coating defect instance label may look like "bubble defect instance #234 at pixels {xy coordinates of a set of pixels in a blob depicting this bubble defect instance #234}" or "bubble defect instance #554 at pixels {xy coordinates of a set of pixels in a blob depicting this bubble defect instance #554}". A coating defect instance label identifies individual instances of one or more defect types identified in the image and in addition identifies the pixel positions of these defect instances in the image. The coating defect instance labels can be graphically represented in the form of a digital image in which image segments representing an identified defect type instances are highlighted. For example, different segments can be graphically represented as segments having a particular color which differ from the color of the intact coating surface. In some embodiments, different segments representing different instances of the same type of defect have different colors. In addition, or alternatively, different segments representing instances of different defect types can have different colors. Defect type instance labels may have the advantage of providing a large amount of detailed information, but the storing and processing of those label may require more resources.

Identifying the approximate (bounding boxes) or detailed (pixel-based) location of defect types and/or defect type instances may have the advantage that the positional information can be further-processed easily by the defect-identification program, e.g. for computing the fraction of pixels of an image covered by the defect, for computing and highlighting identified defects using e.g. elliptic, circular, spine-shaped lines, contours or segment edges and the like. On the other hand, providing a graphical representation of the pattern instances may have the advantage that the identified defects can be easily recognized by a human being. For example, the defect-identification program can generate a graphical user interface (GUI) configured to display image segments having been identified to represent a coating defect of a particular type by a respective color or hatching. For example, image segments identified to represent bubbles or depressions can be highlighted in a particular color, e.g. yellow. Alternatively, only the segment borders can be highlighted. Providing a combination of coordinate information and a graphical representation may have the advantage that the output of the defect-identification program can easily be processed and interpreted both by software and humans.

Applicant has observed that region proposal networks, e.g. the region proposal network provided by the Mask R-CNN program, can accurately identify and characterize a large variety of coating defect types. However, according to some embodiments, other image analysis methods, and in particular blob detection methods, are used instead of or in addition to the Mask R-CNN program for identifying coating defects and/or for characterizing coating surfaces comprising these defects.

For example, the YOLO neural network (J. Redmon and A. Farhadi: "Yolov3: An incremental improvement", arXiv, 2018) can be used for analyzing digital images for identifying coating defects.

According to further examples, one or more of the following blob detection image analysis methods have been observed by the applicant to be able to accurately identify and/or characterize one or more coating defect types, in particular bubble defects and/or cratering defects:

Simple thresholding: the method comprises setting a hard pixel color boundary for performing a binary image segmentation into defects and background. The "color" can be an intensity value of a monochrome image or an intensity value of a color channel of a multi-channel image.

Otsu thresholding: the method comprises automatically calculating a global threshold value from an intensity histogram of a bimodal image.

Adaptive or dynamic thresholding: the method comprises calculating a threshold value separately for small regions of the image, leading to different threshold values for different regions.

According to other embodiments, one or more of the following blob detection methods are used:

"Find contours": the method comprises detecting contours, which are all the points with a similar intensity in a given image.

Edge detection: the method comprises using detected edges, which can be described as discontinuous local features, to separate background and blobs.

Clustering: the method comprises separating an image into similar pixel segments with clustering techniques such as k-means.

Watershed transformation: the watershed transformation method comprises treating the image it operates upon like a topographic map, with the brightness of each point representing its height, and finds the lines that run along the tops of ridges.

According to embodiments, the digital image is pre-processed in order to increase the accuracy of the subsequent image processing steps. For example, the pre-processing of the image may comprise one or more of:

Flood fill: the method comprises adapting adjacent values in an image based on their similarity to an initial seed point in order to minimize noise and improve blob detection.

Morphological transformations: the method comprises performing the basic morphological operators Erosion and Dilation and decreasing or increasing the amount of pixels used by features on the image, such as edges.

Smoothing: the method comprises performing a pre-processing of the image to remove noise via e.g. Gaussian filters.

According to embodiments, the method further comprises installing and/or instantiating the defects-identification program on a data processing system comprising a graphical user interface (GUI). The data processing system can comprise or can be operatively coupled to a camera. The defect-identification program can be configured to generate a GUI which is displayed to a user via a screen of the data processing system. In response to a user action via the GUI, the defects-identification program acquires the image of the coating surface via the camera. The defects identification program uses the acquired image as the image that is processed by the defects-identification program for automatically identifying the defect pattern, for computing the measures of the defect pattern and for computing the qualitative and/or quantitative characterization of the coating surface. Then, the defects identification program performs the outputting of the computed characterization via the GUI or another output interface of the data processing system.

According to embodiments, the defects-identification program is operatively coupled to a camera and is configured for determining whether the camera is positioned within a predefined distance range and/or within a predefined image acquisition angle range relative to the coating surface; for example, the distance range and/or angle range can be adapted to enable acquisition of images from a similar relative position as used for acquiring training images for generating the predictive model of the defects-identification program; in addition, or alternatively, the predefined distance range can be adapted to enable acquisition of images having at least a predefined minimum resolution (pixels per depicted surface area); and in dependence on the result of the determination:
generating a feedback signal for the user and/or for the camera whether adjustment of the camera position is required; and/or
automatically adjusting the relative position of the camera and the coating surface; and/or
enabling the camera to acquire images selectively in case the camera is within the predefined distance and/or image acquisition angle range.

This may have the advantage that the acquisition and analysis of an image of a coating surface is prohibited from the beginning if the current setting of the image acquisition system does not allow the acquisition of digital images under conditions required by the defect-identification program in order to perform an accurate and reproducible defect identification and coating surface characterization process.

For example, the predefined distance range and/or the predefined image acquisition angle range can be a range which is explicitly or implicitly given before the digital image of the currently presented coating surface is acquired.

The resolution of a digital image is indicative of the number of pixels used in this image for depicting a coating surface area of a given size. For example, the resolution can be given as the number of pixels per $cm^2$ of the depicted coating surface, or the number of pixels per $inch^2$.

According to some examples, the predefined minimum resolution can be provided in the form of an absolute resolution value such as at least 5 px×5 px per 0.05 $mm^2$ of the depicted surface, wherein "px" is a pixel. More preferentially, the predefined minimum resolution is at least 10 px×10 px per 0.05 $mm^2$ of the depicted surface, or is at least 15 px×15 px per 0.05 $mm^2$ of the depicted surface.

According to other examples, the predefined minimum resolution is provided in the form of an absolute resolution value range. The lower limit of the range can be, for example, at least 5 px×5 px per 0.05 $mm^2$ of the depicted surface, or at least 10 px×10 px per 0.05 $mm^2$ of the depicted surface, or at least 15 px×15 px per 0.05 $mm^2$ of the depicted surface. The upper limit of the range can be, for example, 10,000×10,000 px per 0.05 $mm^2$ of the depicted surface.

For example, for the defect type "microbubbles", the minimum resolution can be 8 px×8 px per 0.05 $mm^2$ of the depicted surface. A "microbubble defect" as used herein is a bubble defect characterized in that the diameter of the bubbles is below 0.5 mm.

In addition, or alternatively, for the defect type "macrobubbles", the minimum resolution can be 5 px×5 px per 0.6 mm² of the depicted surface. A "macrobubble defect" as used herein is a bubble defect characterized in that the diameter of the bubbles is at least 0.5 mm.

In addition, or alternatively, for the defect type "craters", the minimum resolution can be 8 px>8 px per 0.05 mm² of the depicted surface.

According to some embodiments, the defects-identification program is configured to computationally reduce the resolution of the digital image in case the resolution exceeds the upper resolution range such that the reduced resolution of the digital image is within the predefined resolution range. This may have the advantage that the image with the reduced resolution range has a resolution which is identical or sufficiently similar to the resolution of the training images used for training the predictive model. This may ensure that the defects-identification program can accurately perform the prediction even in case the resolution of the at least one camera should be much higher than the resolution of the training images (which was observed to be an error source).

According to embodiments, the predefined minimum resolution and/or the predefined resolution ranges are defect type specific. For example, for each of one or more different defect types, a respective predefined minimum resolution or resolution range can be stored in association with a defect-type identifier of said defect type in a storage medium.

The applicant has observed that the size of the different coating defect types varies significantly. The applicant has further surprisingly observed that the use of training images whose resolution is adapted to the size of the coating defect type to be learned during the training may have a strong impact both on the computational resources required during the training and the accuracy of the generated predictive model: if the resolution is too high, the training will require large amounts of CPU capacity, memory and time and may in some cases lead to sub-optima results. If the resolution is too low, the accuracy of the trained model will be poor. However, due to the fact that different defect types have different sizes and/or may have different degrees of filigree, the minimum resolution and/or the optimum resolution range to be used both at training time and test time was observed to depend on the defect type.

According to embodiments, the defects-identification-program dynamically receives a selection of one or more defect types to be identified, dynamically determines, for each of the selected defect types, a distance between the at least one camera and the surface which ensures that the image to be acquired will have resolution which is at least the minimum resolution stored in association with an identifier of this defect type in a data storage medium. Alternatively, the defects-identification-program dynamically determines, for each of the selected defect types, a distance between the at least one camera and the surface which ensures that the image to be acquired will have a resolution which represents the optimum resolution range of this defects type and which is stored in association with an identifier of this defect type in a data storage medium. Then, the defects-identification-program triggers a relative movement of the at last one camera and/or the presented surface such that the camera is enabled to acquire the image in a resolution which is at least the minimum defect-type-specific resolution and/or which is within the optimum resolution range of this defect type. In case multiple defect-types are selected, the camera repeats the adaptation of the relative distance for each of the selected defect types. In addition, or alternatively, the defects-identification-program outputs a feedback signal enabling a user to manually or semi-automatically adjust the relative position.

The predefined image acquisition angle range may depend, for example, on the image acquisition angles of the at least one camera used for acquiring the training images and may be chosen such that the image acquisition angle of the at least one camera to be used for acquiring an image of the currently presented coating surface is sufficiently similar to the image acquisition angle(s) used for obtaining the training images. The term "similar" may mean e.g., having the same image acquisition angle +/−<5%, or having the same image acquisition angle +/−<10%, or having the same image acquisition angle +/−<15%, or having the same image acquisition angle +/−<20%, or having the same image acquisition angle +/−<40% as the image acquisition angle used for acquiring the training images.

According to some examples, the predefined distance range is a range of distances between the at least one camera (to be used for acquiring the digital image of the currently presented coating surface) and the presented coating surface which will result in the acquisition of a digital image having a resolution of at least the minimum resolution, whereby the minimum resolution is a defect-type specific minimum resolution associated with a particular defect, whereby the predictive model was trained to recognize this defect type based on training images having at least the said minimum resolution.

Dynamically adapting the camera-surface-distance may be beneficial as the type and/or the configuration of the at least one camera used for acquiring the digital image of the currently presented coating surface may differ from the type and/or configuration of the camera(s) used for acquiring the training images. Automatically determining whether the at least one camera has a distance to the surface area which allows to acquire a digital image having a resolution which is at least the predefined minimum resolution or which is within a predefined resolution range may allow ensuring that the camera is only enabled to acquire the digital image if the predictive model will likely be able to identify coating defects of one or more different types. Likewise, automatically determining whether the at least one camera has an image acquisition angle which allows to acquire a digital image from a similar angle as used for acquiring the training images may allow ensuring that the camera is only enabled to acquire the digital image if the acquisition angle is similar to the acquisition angle used for acquiring the training images.

According to embodiments, the predefined image acquisition angle ranges are defect type specific. For example, for each of one or more different defect type, a respective predefined image acquisition angle range can be stored in association with a defect-type identifier in a storage medium.

According to some embodiments, the training images used for training the predictive model(s) of the defect-identification program do not only depict a coating surface, but also depict a reference object of known size. For example, the reference object can be positioned on or next to the coating surface. The reference object can be, for example, a coin, a piece of paper, or any kind of object with a known size. The same type of reference object is placed on or next to the coating surface currently presented to the at least one camera. According to some embodiments, at training phase of the predictive model, the number of pixels used for depicting the reference object in each of the training images is determined for computing a resolution of each training image as a function of the known reference object size and the determined number of reference-object-pixels. The computed resolutions are stored, according to some examples, as part of the training data, e.g. on a per-training-image basis. In some examples, the minimum resolution used for obtaining the training images (used for obtaining all training images or used only the images of one or more specific defect types) is used as the lower limit of the predefined resolution range.

According to some embodiments, the defects-identification program can be configured to determine, before acquiring the image of the currently presented coating surface, the anticipated resolution of this image given the current distance of the at least one camera from the presented surface area and/or given the current configuration of the at least one camera. For example, the defects-identification program may be communicatively coupled to the at least one camera and may request the anticipated resolution given the current distance and/or configuration directly from the at least one camera. According to other embodiments, the anticipated resolution is read from or computed based on a configuration file or other data source comprising the current settings of the at least one camera.

According to other embodiments, the anticipated resolution is determined based on a reference object. A reference object of known size is positioned on or next to the coating surface currently presented to the at least one camera. The at least one camera captures a preview-image depicting at least the reference object and determines the number of pixels in the preview-image which depict the reference object. The determined number of pixels in the preview-image which depict the reference object is the anticipated resolution of the at least one camera in its present state. The anticipated resolution is compared with the predefined resolution range to determine if the current, anticipated resolution is within the predefined resolution range. For example, if the current distance between the at least one camera and the surface is determined to be below the predefined minimum resolution (and/or lie outside of a predefined distance range) this can be used as an indication that the anticipated resolution will not enable the defects-identification program to accurately identify the coating defects.

In case the anticipated resolution is identical to or above the minimum resolution, the user is enabled to capture the digital image via the at least one camera manually or the at least one camera is caused to capture the image automatically.

In case the anticipated resolution is below the predefined minimum resolution (and/or is outside of the predefined resolution range), the distance between the at least one camera and the currently presented coating surface is modified such that the modified distance is within the predefined distance range, thereby ensuring that the anticipated resolution of the camera at the modified position is identical to or above the minimum resolution (and/or is within the predefined resolution range).

According to embodiments the image acquisition angle is adapted analogously. For example, a configuration file, a camera interface and/or or the computational identification of the shape of a reference object (which occurs only if viewed from a particular angle range) depicted in a preview image is used for determining the anticipated image acquisition angle given the current distance, position and orientation of the at least one camera.

The feedback signal may assist the user in positioning the camera correctly and/or to modify the setting of the image acquisition system as to ensure appropriate image acquisition conditions. For example, the feedback signal may show the user in which direction or at which angle he has to move or rotate the camera in order to position it at a suitable position relative to the coating surface. In some examples, the feedback is output via a GUI. In addition, or alternatively, the feedback signal can comprise an acoustic alarm.

For example, a user or an application program or a configuration file may select or determine the type of defects to be identified, e.g., via a GUI or via a configuration file. The selection or determination of the defect types to be examined and identified in the image may hence determine which image acquisition angles and/or distances are considered allowable for identifying a particular type of defect. This may increase accuracy of the defect identification, because it was observed that different types of defects can be identified best at different illumination and/or image acquisition conditions.

According to other embodiments, a corresponding feedback signal is generated and provided to an image acquisition unit of a facility for automatically manufacturing and/or testing coating compositions. The feedback signal can comprise control commands causing the camera and/or the light source comprised in the image acquisition unit to automatically change their relative position to the coating surface, the illumination angle and/or the image acquisition angle such that the image acquisition unit is enabled to acquire digital images of a coating surface currently comprised in the unit under conditions required by the defect-identification program for proper image analysis.

For example, the feedback signal can be a signal for a human user for enabling the user to correct the position (distance and/or orientation) of the camera manually or semi-automatically. The feedback signal may in addition or alternatively comprise a machine-command for enabling a controller unit to correct the position of the camera automatically or semi-automatically.

The feedback signal can be, for example, an overlay-image superposed on a preview image of the coating surface acquired by the at least one camera, whereby the overlay-image comprises one or more GUI elements indicating whether or not the at least one camera is in a position suitable for acquiring an image which can be successfully processed by the defects-identification-program.

According to embodiments, the defects-identification program is selected from a group comprising:
an application program, wherein the data processing system is a stationary or portable data processing system, e.g. a general-purpose data processing device, in particular a portable telecommunication device, e.g. notebooks, smartphones, tablet computers or other general-purpose data processing devices can be used as portable data processing systems; the camera can be an inbuilt, device-internal camera or an external camera, e.g. a digital camera or camcorder; using general-purpose data processing systems may have the advantage that no additional, special-purpose hardware is required for enabling the staff of a company to conduct an accurate and reproducible quality control of coating compositions and/or coating surfaces manufactured by the company;
an application program, the data processing system being a portable or stationary device specially designed for quality control of coating surfaces; for example, the specially designed quality control device can comprise additional components such as a camera and/or an illumination source whose position relative to the coating surface can be controlled by the defect-identification program; embodiments of the invention may ensure that these devices are able to automatically identify and characterize coating surface defects and the quality of the examined coating surfaces in a reproducible and accurate manner;

an application program, the data processing system being a high-throughput (HT) facility (also referred to as "high throughput equipment—HTE) for the automated or semi-automated manufacturing of coatings; in particular, the high throughput facility can be a facility comprising an automated image acquisition unit as described herein for embodiments of the invention; using the defects identification program in the context of an HT-facility may be particularly advantageous, because HT-facilities are able to automatically manufacture and test many different coating compositions and coating surfaces, thereby creating large amounts of data which again can be used for training a machine learning model to identify and/or predict coating compositions having desired coating quality characterizations; automatically generating and storing qualitative and/or quantitative coating characterizations in the context of an HT-facility may allow to consider coating defects and coating quality characterizations in various big data applications, in particular machine learning based predictions; this was not possible based on manually created, subjective and inconsistent quality labels;

a web application downloaded and/or instantiated permanently or temporarily via a network; for example, a server can provide a Java application implementing the defect-identification program via the Internet; or a program executed within a browser, e.g. a JavaScript program.

a server program instantiated on a server computer, the server program being operatively coupled via a network connection to a client program instantiated on a client data processing system (e.g. a general purpose computer, a device specially designed for quality control, or a smartphone); for example, the client program can be a program configured to control one or more cameras for acquiring one or more digital images of coating surfaces; the acquired digital images are sent via the network to the server program used for processing the images and output the processing results including the characterization of the coating surface via the network to the client program. The client program can in addition be configured for displaying the results provided by the server program.

A "portable device" can be, for example, a hand-held device such as a smartphone, but according to some examples, a portable device can also be a larger device up to a weight that can be carried by a human being for at least a few meters without the aid of technical means. Typically, such devices weigh less than 50 kg, in particular less than 40 kg.

Combinations of the above-mentioned embodiments are possible. For example, it is possible that the defect-identification program is implemented as a client-server-system, wherein the client part is implemented as the web application or the browser-executed program, is instantiated on the data processing system and is responsible for acquiring a digital image in sufficient quality and in an appropriate context, and wherein the server part is instantiated on a remote server computer and is responsible for performing the image analysis for identifying the coating defects and for providing the coating surface characterization. According to another example, the client program and the client data processing system can be part of a facility for preparing and/or testing coating compositions, e.g. an HTE. The server program, for example, may also be a (remote) part of the said HTE, may be used as a server for multiple client programs belonging to multiple different HTEs and/or may not be part of an HTE. The server computer system can be a monolithic computer system or a distributed computer system, e.g. a cloud computer system.

According to embodiments, the defect-identification program comprises a predictive model having learned from training data in a training step performed by a machine learning program to recognize the predefined patterns. In particular, the machine learning program can be a neural network.

According to embodiments, the training data comprises multiple labeled training images of multiple coating surfaces. For example, the training images can comprise digital images depicting coating surfaces obtained by applying a coating composition on substrates of many different types (e.g. wood, plastic, metal, paper and the like), by applying a coating composition according to many different coating application protocols (e.g. once or multiple times, at different temperatures, using e.g. spraying, spreading, painting or immersion technique, after having performed different types of pre-treatment protocols of the substrate, etc.). In addition, or alternatively, the training images can comprise digital images depicting coating surfaces obtained by applying many different coating compositions, whereby the different coating compositions have been obtained by combining different types and/or amounts of components and/or by combining the components according to different manufacturing process parameters (e.g. mixing duration, mixing temperature, mixing speed, etc.) and/or different application process parameters. Hence, the training data may cover a huge, multidimensional data space covering a variety of different substrates, coating compositions, coating composition manufacturing parameters and coating application protocol parameters. The method further comprises storing the training data in a database. Initially, the labels of the training data will be manually annotated. In later training steps, the training data may be extended by additional digital images of coating surfaces which have been automatically labeled and which are preferably checked or corrected by a human annotator. The labels preferably comprise a pixel-based indication of the boundaries of coating defects, the type of coating defect, and one or more quantitative and/or qualitative characterizations of the coating surface which in some cases may be identical to a comprise measures of the one or more defects depicted in the respective training image.

According to embodiments, the machine learning program is a neural network or a set of neural networks comprising a region proposal network. The region proposal network is configured to create anchors in an input image for making a proposal whether the anchor likely contains an object (one of the defect patterns). The "anchors" can be understood as sub-regions of the input image having anchor sizes covering the sizes of the defect patterns to be detected.

For example, the average size of certain types of defects such as bubbles, foam-depressions and the like may already be known. The size ranges of these defects can be used as the expected size range of the defect patterns. The region proposal network is configured to create and use for the detection of defects (e.g. "bubbles" and "craters") anchors having sizes which cover the size ranges of the expected sizes of one or more defect types to be identified. According to some embodiments, multiple different anchors sizes are defined by a user during training, e.g. anchors from a set of anchors having the sizes 8×8 pixels, 16×16 pixels, 32×32 pixels, 64×64 pixels and 128×128 pixels can be used.

A "region proposal neural network" (RPN) as used herein is a neural network configured to operate on many different sub-regions of an input image referred to as "anchors" which are adapted to make "proposals" regarding the occurrence of an object in the sub-region.

According to preferred embodiments, the region proposal neural network is a region proposal network comprised in the "Mask R-CNN" model as described, for example, in "Mask R-CNN", Kaiming He and Georgia Gkioxari and Piotr Dollar and Ross Girshick, 2017, eprint 1703.06870, arXiv:1703.06870. The "Mask R-CNN" is a flexible neural network-based program configured for efficiently detecting objects in an image while simultaneously generating a high-quality segmentation mask for each instance. The Mask R-CNN program extends Faster R-CNN by adding a branch for predicting an object mask in parallel with the existing branch for bounding box prediction. Mask R-CNN has four main outputs: For each candidate object (candidate defect type instance), a class label, a score and a bounding-box is provided. In addition, an object mask can be provided. Mask R-CNN adds only a small overhead to Faster R-CNN. Applicant has observed that the Mask R-CNN is particularly suited for identifying coating surface defects of many different types as it is easy to generalize to many different tasks in the same framework. Mask R-CNN can be downloaded via https://github.com/matterport/Mask_RCNN. The use of the Mask RCNN for instance segmentation of other object types is described in the online article "Splash of Color: Instance Segmentation with Mask R-CNN and TensorFlow" written by Waleed Abdulla Mar. 20, 2018 and available online via the URL https://engineering.matterport.com/splash-of-color-instance-segmentation-with-mask-r-cnn-and-tensorflow-7c761e238b46. The Faster R-CNN approach is described by Shaoqing Ren and Kaiming He and Ross Girshick and Jian Sun in "Faster R-CNN: Towards Real-Time Object Detection with Region Proposal Networks", 2015, eprint 1506.01497 available via https://arxiv.org/abs/1506.01497.

According to one example, the neural network comprises a "backbone" network and an RPN. The "backbone" network can be a standard convolutional neural network (typically, ResNet50 or ResNet101) that is applied on the input image first and that serves as a feature extractor. The early layers of the "backbone network" detect low level features (edges and corners), and later layers successively detect higher level image features. The RPN is preferably trained to produce region proposals based on feature vectors derived from the input image provided by the backbone neural network.

The operation of Mask R-CNN may roughly be summarized as follows:
  the image is run through the "backbone network" to generate the feature maps.
  The RPN generates multiple Regions of Interest (RoIs) using a lightweight binary classifier. It does this using anchors boxes over the image. The "anchors" or "anchor boxes" can be understood as a set of bounding boxes covering a certain size range to capture the scale and aspect ratio of specific defects types to be detected. According to embodiments, the multiple different anchors are processed in parallel on a CPU (central processing unit) or GPU (graphical processing unit). This will greatly increase processing speed for the detection of defect instances of one or more different defect types. Anchor boxes also help to detect multiple objects, objects of different scales, and overlapping objects without the need to scan an image with a sliding window that computes a separate prediction at every potential position. This makes real time object detection possible. For each of the anchors the region proposal network predicts whether the anchor contains an object (foreground class) or not (background class). For all foreground anchors in addition a bounding box refinement is performed to better fit the object (coating defect). These regions are also called regions of interest (RoI).

For each RoI, a proposal is predicted. Each proposal is a combination of a score of the RoI's probability of depicting a particular type of object (e.g. 93% for a bubble defect) and also the class/label of the object (e.g. "bubble defect", "cratering defect" or "background").

The regions of interest are further refined by performing an additional bounding box refinement step.

Additionally, segmentation masks are predicted for the positive anchors (regions of interest containing an object), being indicative of an identified defect instance on the pixel level. For example, a Mask R-CNN has been observed to be able to identify and characterize foam defects highly accurately.

The above-mentioned steps describe how the already existing and/or trained defect-identification program can be applied on new (test) images which do not comprise a label indicating the occurrence, type or extent of coating defects. In the following, embodiments of a method for generating and training the predictive model of the defect identification program are described. The test phase and the training phase can be performed on the same or on different data processing systems. For example, it is possible to train the model M1 on a first data processing system, integrate the trained model M1 in a defect-identification program which may comprise some additional functions or modules, e.g. for interacting with a user and/or with a facility for manufacturing or testing coatings, and transfer the defect-identification program to a second data processing system.

Training Phase of the Model (M1) of the Defect-Identification Program

According to embodiments, the method comprises performing the training step on the training data, the training data comprising a set of labeled digital training images of coating surfaces, the labels identifying the location/positions and/or type of defects in the training images. The predictive model is trained for recognizing the pattern by means of the labeled training images using back propagation.

For example, the training images may respectively have assigned labels indicating whether the image depicts one or more defect types which do not indicate the location and/or extent of the coating defects. Preferably, the training images comprise images of various coating surfaces being free of any defect, training images comprising defects of a single defect type of varying extent, and/or training images comprising a mixture of defects of two or more different types.

The labels of the training data can comprise image class labels which indicate the defect types(s) depicted in the image, if any, but are free of positional information of the defects. In addition, or alternatively, the labels can comprise semantic defect type labels, object identification labels and/ or defect type instance labels which provide information on the location of the defect types or defect type instances on the pixel level or at the level of bounding boxes.

In addition, or alternatively, the training images according to embodiments of the invention have assigned a quantitative measure of one or more defects depicted in the training images, e.g. the size and/or severity of the defect or the number of bubbles, etc. These parameters and respectively assigned labels and quantitative measures are processed in the training step for enabling the predictive model to correlate the parameters with the defect patterns and with the measures of the coating defects of the coating surface.

According to embodiments, the defect identification program can comprise multiple predictive models M1.1, M1.2, M1.3 respectively having learned to correlate some defect-related image annotations with intensity or color patterns in a digital image. For example, the predictive model M1.1 may be the region proposal network of the Mask-RCNN program having learned to correlate annotated defects and pixel patterns, and the model M1.2 may be another neural network having learned to correlate defect measures and other parameters stored in association with the respective digital images with the annotated defects. The defect identification program comprises the multiple predictive models M1.1, M1.2, M1.3 and integrates and/or aggregates these models and their results for performing the prediction.

Providing the defect-identification program in a machine learning process may have the advantage that the generated predictive model M1 will have learned a plurality of highly complex interrelations between image patterns and various defect types. Applicant has observed that it is very difficult and, in some cases, even impossible to integrate these complex and largely hidden interrelations into a predictive model by means of one or more rules explicitly specified by a human.

According to embodiments, at least some of the training images have in addition assigned parameters related to the coating compositions used for creating the coating surfaces depicted in the training images.

These additional, optional parameters assigned to the training images used for training the predictive model M1 (or one of multiple other predictive models M1.2 to be used by the defect identification program) can comprise one or more of:

- an indication of one or more components of the coating composition used for generating the coating surface depicting in the training image;
- an indication of an absolute or relative amount of one or more of the components of the coating composition; for example, the parameters may comprise a specification of the type and/or amount of one or more defoamers comprised in the coating composition used for generating the depicted surface; and/or
- one or more manufacturing-process parameters, the manufacturing-process parameters characterizing a process of generating a coating composition, the process parameters for example comprising mixing speed, the mixing temperature, and/or the mixing duration of the coating composition; and/or
- one or more application-process parameters, the application-process parameters characterizing a process of applying a coating composition on a substrate, the application-process parameters in particular comprising the amount of coating composition applied per area of the coating surface, the type of substrate and/or or the type of application equipment (e.g. machines or devices); the application process parameters may also comprise parameters being indicative of a method of pre-processing the substrate onto which the coating composition is applied, e.g. drying, heating, cleansing or otherwise preparing the substrate; and/or
- system parameters of an imaging system used for acquiring the training images, the system parameters being selected from a group comprising type of light source(s) used for illuminating the coating surface, brightness of the light source(s), illumination angle, wavelength of the light source(s), type(s) of one or more camera(s) used for acquiring the digital image of the coating surface, image acquisition angle(s), position of the one or more camera(s).

Training the predictive model to be integrated in the defect-identification program on the above-mentioned context data may be advantageous, because applicant has observed that the above-mentioned context parameters may all have an impact on the number and type of defects to be observed in the coating surface and hence have an impact on the coating surface quality. Annotating the training images with the above-mentioned context data and/or the quantitative measure of the defects ensure that the trained predictive model M1 is able to take into account any factor that may have an impact on the type and extent of coating defects and on the quality characterizations of the coating surface.

Further Embodiments

In a further aspect, the invention relates to a computer-implemented method for providing a coating-composition-related prediction program, e.g. a composition-quality-prediction program and/or a coating-composition-specification-prediction program. The method comprises:

- providing a database comprising associations of qualitative and/or quantitative characterizations of coating surfaces in association with one or more parameters selected from the group comprising one or more of the components of the coating composition used for producing the respective coating surface, relative and/or absolute amounts of one or more of the said components, manufacturing-process parameters of the coating composition and/or application-process parameters used for creating the coating surfaces;
- training a machine learning model on the associations of the coating surface characterizations with the one or more parameters in the database for providing a predictive model (e.g. predictive models referred herein as model "M2" or "M3") having learned to correlate qualitative and/or quantitative characterizations of one or more coating surfaces with one or more of the parameters stored in association with the respective coating surface characterizations; and
- providing a composition-quality-prediction program which comprises the predictive model (M2), the composition-quality-prediction program being configured for using the predictive model (M2) for predicting the properties of a coating surface to be produced from one or more input parameters selected from the group comprising one or more components of a coating composition to be used for producing a coating surface, relative and/or absolute amounts of one or more of the said components, manufacturing-process parameters to be used for preparing the coating composition and/or application-process parameters to be used for creating the coating surface; and/or
- providing a composition-specification-prediction program which comprises the predictive model (M3), the composition-specification-prediction program being configured for using the predictive model (M3) for predicting, based on an input specifying at least a desired coating surface characterization and outputting one or more parameters related to a coating composition predicted to generate a coating surface having the input surface characterizations, the one or more output parameters being selected from the group comprising one or more components of the said coating composition, relative and/or absolute amounts of one or more of the said components, manufacturing-process parameters to be used for preparing the coating composition and/or application-process parameters for creating the coating surface; optionally, the composition-specification-prediction program is configured for receiving an incomplete coating composition specification and for using the specification for limiting the solution space of the predicted output parameters.

Embodiments of the invention may have the advantage that a composition-quality prediction program is provided which is able to automatically predict quality characterizations of a particular coating composition as a function of the type and/or amount of the components of the composition and optionally as a function of further parameters. This may tremendously accelerate the process of testing and identifying a coating composition which is able to provide a coating surface having the desired quality characterizations. Contrary to prior art approaches which are based on human experience and a typical large number of coating compositions manufactured and tested at the workbench, embodiments of the invention may allow accurately predicting, whether or not a particular coating composition will have the desired coating surface characterizations or not. This may tremendously accelerate the process of identifying a suitable coating composition and reduce the costs associated with reagents, machines and consumables required to perform this identification process.

While the predictive model M1 of the defect-identification program is preferably obtained by performing a machine learning step on manually annotated training images and has learned to correlate pixel patterns with defect-type characterization measures and coating surface characterizations, the predictive model M2 of the composition-quality prediction program can be trained on training data which may comprise but preferably do not comprise digital images. The purpose of the predictive model M2 is to predict coating surface characterizations, in particular quality-related characterizations, as a function of the one or more components and optionally also context parameters of a coating composition.

According to embodiments, the method comprises providing a plurality of images respectively depicting a coating surface. The depicted coating surfaces are made by applying multiple different coating compositions on respective surface samples. At least some of the depicted coating surfaces respectively have one or more coating defects of one or more different defect types. The method comprises applying a defect-identification program on the images for recognizing patterns in the images, for obtaining the measures of the coating defects represented by the identified patterns and for computing a qualitative and/or quantitative characterization of the coating surfaces depicted in the images. The method further comprises storing the qualitative and/or quantitative characterizations of the coating surfaces in association with one or more parameters related to the coating composition used for creating the coating surface comprising these defects in the database for providing the training data for the predictive model (M2, M3). For example, these parameters can be selected from the group comprising one or more components of the said coating composition, relative and/or absolute amounts of one or more of the said components, manufacturing-process parameters to be used for preparing the coating composition and/or application-process parameters for creating the coating surface.

This may be advantageous as the automated defect identification and coating surface characterization may allow to annotate a huge number of images automatically in a reproducible and comparable manner. Providing a large, unbiased training data set may ensure that the model M2 having been trained on this training data set is able to predict the coating composition properties, in particular the quality of a coating surface obtained by applying the composition on a substrate, accurately.

According to embodiments, the defect-identification program is the defect-identification program specified in any one of the embodiments or examples described herein.

According to embodiments, the qualitative and/or quantitative measures have assigned parameters considered in the machine learning step for generating the predictive model (M2, M3) to be used by the composition-quality-prediction program or by the composition-specification-prediction program. The parameters comprise:
  an indication of one or more of the components of the coating composition; for example, an indication of a component can specify a particular chemical compound, e.g. a particular pigment or a particular defoamer, or a substance class, e.g. "solvent-based coating medium";
  an indication of the absolute or relative amount of one or more of the components of the coating composition; for example, the indication may specify the relative amount of two defoamers;
  one or more manufacturing-process parameters, the manufacturing-process parameters characterizing a process of generating a coating composition, the process parameters for example comprising mixing speed and/or mixing duration of the coating composition; and/or
  one or more application-process parameters, the application-process parameters characterizing a process of applying a coating composition on a substrate, the application-process parameters in particular comprising the amount of coating composition applied per area of the substrate, the type of substrate and/or or the type of application equipment.

A data file or data record comprising the above-mentioned parameters is also referred to as "specification" of a coating composition. A specification is complete if it specifies the nature and amount of each component and specifies all further information needed in the respective application context in order to prepare a coating composition and a corresponding coating surface. Typically, the specification is incomplete: for example, the nature and/or amount of at least some of the components may not be specified or some coating-composition-manufacturing process parameters and/or coating-composition-application-parameters may not be specified.

According to embodiments, the method comprises using the composition-quality-prediction program for predicting the properties of a coating composition. The coating composition can be a paint, a varnish, a printing ink, a grinding resin, a pigment concentrate or other substance mixture for coating a substrate.

According to embodiments, the method comprises using the composition-specification-prediction program for predicting one or more of the above-mentioned parameters (nature and/or amount of coating compositions, manufacturing-process parameters, application-process parameters) based on a characterization of a desired coating surface provided as input. These parameters can be used for completing and/or optimizing a specification of a coating composition.

According to preferred embodiments, a combination of both models M2, M3 is used for supplementing and/or optimizing a coating composition specification. For example, the composition-quality-prediction program using predictive model M2 may receive as input a specification of a coating composition which in addition comprises some manufacturing and/or application process parameters. Based on the received specification, the composition-quality-prediction program may predict that the coating surface may comprise many bubble defects. Then, the user may input into the composition-specification-prediction program using the model M3 that a coating composition specification shall be predicted which minimizes bubble defects, whereby the coating composition specification can be provided to the composition-specification-prediction program as additional input and constraint for the prediction. The model M3 will determine that a modification of the ratio of the two defoamers will result in a reduction of bubble defects and may output a modified version of the input specification, the modified specification comprising a modified ratio of the two defoamers.

Coating compositions are complex mixtures of raw materials. Common compositions or recipes or formulations for coating compositions contain about 20 raw materials, hereinafter also referred to as "components". These compositions consist, for example, of raw materials selected from among solids, such as pigments and/or fillers, further binders, solvents, resins, hardeners and various additives, such as thickeners, dispersing agents, wetting agents, adhesion promoters, defoamers, surface modifiers, levelling agents, catalytically active additives such as dryers and catalysts and specially effective additives such as biocides, photoinitiators and corrosion inhibitors.

Up to now, new compositions, formulations and reformulations with certain desired properties have been specified on the basis of empirical values and then prepared and tested. The composition of a new composition that fulfils certain expectations in terms of its chemical, physical, optical, haptic and other measurable properties and in particular in terms of the quality/defectiveness of a coating surface obtained by coating a substrate with the composition is hardly predictable even for an expert due to the complexity of the interactions and due to a lack of high quality data suitable for use in a machine-learning training step. Due to the diversity of the interactions of the raw materials and process parameters among each other and the associated large number of failed experiments, this procedure is both time-consuming and costly.

Thus, there are currently very narrow limits to both human-made and computer-aided assessment and prognosis regarding the components of a composition with desired properties. This is particularly true for complex compositions with many relevant properties and many components, as is the case with paints, varnishes, printing inks, grinding resins, pigment concentrates or other coating materials, since the components interact with each other in a complex way and determine the properties of the corresponding coating composition. The identification of one or more defoamers being alone or in combination able to minimize the bubble defect generation has been observed to be particularly challenging.

At present, new coating surfaces must first be produced in a real laboratory environment and their properties must then be measured in order to assess whether a new coating composition has certain required properties. Although there are already approaches for the automatic prediction of properties of chemical substances, the creation of a training data set of sufficient size and quality is often even more complex than directly producing and testing the composition in question. The development of new compositions in the field of paints, varnishes, printing inks, grinding resins, pigment concentrates or other coating materials is particularly complex and requires a lot of time.

According to embodiments, the using of the composition-quality-prediction program comprises:
  providing each of the specifications of a plurality of different candidate coating compositions as input to the composition-quality-prediction program;
  predicting, by the composition-quality-prediction program, for each of the candidate coating compositions the quality of a coating surface generated by applying the candidate coating composition on a substrate, the prediction being performed as a function of the specification of the candidate coating composition;
  selecting a candidate coating composition specification in dependence on the respectively predicted measures; for example, the selection can be performed manually such that the one of the candidate coating composition specification is selected whose predicted coating surface characteristics best meets a quality requirement; according to other embodiments, one or more parameters being indicative of one or more desired surface characterizations used as quality criteria are provided as input to the composition-quality-prediction program, thereby enabling the composition-quality-prediction program to perform this selection step automatically in dependence on the input quality criteria, and
  outputting the selected specification as a recommended coating composition predicted to have the highest quality; and/or
  inputting the selected candidate coating composition specification to a processor which controls a facility for producing and/or testing compositions for coating compositions, wherein the processor drives the facility to produce the input coating composition.

For example, the prediction is generated by a computer system connected to the facility for producing and/or testing compositions for coating compositions. The facility can be a HT-facility.

According to embodiments, the method further comprises:
  receiving an incomplete specification of a coating composition;
  manually or automatically generating a set of specifications of candidate coating compositions; the set of candidate compositions are different versions of the received incomplete coating composition; the creation of the specifications of the candidate coating compositions comprises:
    a) supplementing the specification of the incomplete coating composition with one or more further components; and/or
    b) supplementing the specification of the incomplete coating composition with different absolute or relative amounts of the one or more further components and/or with different absolute or relative amounts of the already specified components; and/or c) supplementing the specification of the incomplete coating composition with one or more manufacturing-process-parameters characterizing the process of manufacturing the candidate coating composition; and/or d) supplementing the specification of the incomplete coating composition with one or more application-process-parameters characterizing the process of applying the candidate coating composition on a substrate.

For example, the received incomplete specification may specify that the (desired) coating composition to be produced should comprise/be based on an organic solvent but the incomplete specification does not specify which one of a plurality of available solvents should be used. The candidate compositions could be created such that different organic solvents (but not a water-based solvent) are used as the "solvent"-component.

According to another example, the received incomplete specification may specify that the (desired) coating composition should comprise two particular defoamers (e.g. TEGO Foamex 810 and TEGO Wet 285, Co. Evonik) but does not specify their absolute or relative amounts. The candidate compositions could be created such that different amount ratios of the two defoamers are used.

According to another example, the incomplete specification may specify that a particular pigment or pigment combination should be used but is silent about the amount of the pigment or only provides an amount range of the pigment(s). The candidate compositions could be coating compositions differing from each other in respect to the amount of the pigment(s).

According to another example, the incomplete specification may specify all or at least most of the components of the coating composition and their respective amounts but is silent about context parameters, in particular manufacturing process parameters such as mixing time, mixing duration, mixing temperature etc. and/or coating application process parameters (spreading, spraying, painting, immersing, pretreating the substrate, temperature, ventilation, etc.). The candidate compositions could be coating compositions differing from each other in respect to the parameter values of one or more of the above-mentioned context parameters.

According to embodiments, the further data used for supplementing the candidate coating composition specifications in the respective cases a), b), c) and/or d) is used as input by the coating composition-quality-prediction program for performing the prediction.

Embodiments of the invention may be beneficial for manufacturers of coating additives as well as manufacturers of coating compositions for multiple reasons: manufacturers of coating compositions may predict properties of a plurality of various candidate compositions in combination with various context parameter values without actually manufacturing and testing these coating compositions.

However, embodiments of the invention may also be useful for the manufacturers of individual coating composition components such as solvents, binders, pigments, foaming agents, defoamers, rheological additives, flame retardants, dispersing agents, and the like. For example, the manufacturer of a defoamer may receive an order for a defoamer to be used in a coating composition for wooden materials from a manufacturer of a coating composition. The received specification may indicate that the coating is to be applied on wooden materials and is based on water as a solvent, but detailed specification of the coating composition is not disclosed for confidentiality reasons. Nevertheless, the manufacturer of the defoamer would like to identify the type and amount of one or more defoamers, ideally a defoamer mixture, and the amount of the solvent which in combination are best suited to provide a coating for wooden materials with a high coating surface quality. In order to achieve this, the employees of the additive manufacturer or a software program generates a plurality of candidate coating composition specifications which differ from each other in respect to the type, mixture thereof and/or amount of the defoamer and/or in respect to the ratios of the defoamers used. Each candidate coating composition specification comprises an indication that the coating is to be used to coat wooden materials. Then, the composition-quality-prediction program uses each of the candidate coating composition specifications as input for predicting a characterization of the respective candidate coating composition, in particular a characterization being indicative of the quality of a coating surface generated by applying the candidate coating composition on a wooden substrate. As the composition-quality-prediction program has learned to correlate a plurality of types and/or amounts of components and optionally also context parameters with coating surface characterizations, the composition-quality-prediction program is able to identify a suitable combination of defoamers. The manufacturer of the defoamer can provide the defoamer mixture to the manufacturer of the coating composition together with a recommendation regarding the relative or absolute amounts of the defoamer and the solvent and/or together with a recommendation for process parameters relating to the creation, storing and/or application of the coating composition.

Embodiments wherein the composition-quality-prediction programs is configured to generate a specification of a recommended coating composition which in addition specifies one or more of the above-mentioned parameter types a)-d) may be advantageous as applicant has observed that not only the composition but also process parameters have a tremendous impact on the properties and quality of a coating surface. However, due to the huge number of combinatorically possible combinations of components and process parameters, it was hitherto not possible to evaluate all combinations which might correspond to a high-quality coating surface.

The above described embodiments are based on providing a plurality of (hypothetical) candidate coating composition specifications, predicting the respective coating surface quality and selecting the one of the candidate coating compositions whose predicted surface properties appear to be most desirable. However, alternative approaches may use the learned correlations between the coating surface characteristics and the coating composition related parameters which have been incorporated in the predictive model M3 more directly for identifying promising coating compositions:

According to embodiments, the using of the coating composition-specification-prediction program comprises:
providing at least a specification of a desired coating surface characterization as input to the composition-specification-prediction program; and
predicting, by the composition-specification-prediction program, a specification of a coating composition adapted to provide a coating surface having the desired surface characteristics, wherein the specification comprises parameters selected from a group comprising: one or more coating composition components, absolute or relative amounts of one or more of the coating composition components, manufacturing process parameters and/or application process parameters.

According to preferred embodiments, the method further comprises outputting the predicted specification of the coating composition to a human and/or inputting the specification of the selected candidate coating composition to a processor which controls a facility for producing and/or testing compositions for coating compositions, wherein the processor drives the facility to produce the input coating composition.

In addition to the desired surface characterizations, additional constraints may be provided as input. The constraints may consist of an incomplete, rough coating composition specification being indicative of some components or component substance classes and some absolute or relative amounts. The constraint may be that any alternative component suggested must belong to the same substance class or any alternative amount must not deviate from the amount provided in the constraint by more than a maximum threshold value. Manufacturing process parameters and/or application process parameters may also be provided as constraints.

According to embodiments, the method is performed on a computer system operatively coupled to an automated surface coating and image acquisition unit (ACAIA unit). The ACAIA unit comprises one or more cameras and optionally one or more light sources. The ACAIA unit is a component of a facility for producing and/or testing coating compositions or is operatively coupled to the facility by automated transport means, e.g. for automatically transporting a coated substrate sample to and from the ACAIA unit. The method further comprises sending one or more control commands to the facility. The control commands cause the facility to:
  transport the produced coating composition to the ACAIA unit and apply the transported coating composition on a substrate; alternatively, the coating process is performed in a separate coating unit of the facility and the facility is configured to transport the already coated substrate sample to the ACAIA unit;
  positioning the coated surface and the camera relative to each other within a predefined distance and/or predefined angle range; for example, the predefined distance and/or angle range can be distances and/or angles specific for one or more types of surface defect types to be detected in the digital images to be acquired; the indication of the defect types of interest may be provided with the control commands or may be specified in a configuration of the ACAIA unit; and
  after the positioning, causing the camera of the ACAIA unit for acquiring a digital image of the coating surface; and
  returning the acquired image to the computer system.

This may be advantageous as a fully automated system for predicting, manufacturing, and testing a coating composition in the context of an automated manufacturing facility, in particular a HT-facility, is provided. The data obtained in the image-analysis based testing step may be used for extending the training data of the composition-quality-prediction-program and/or of the composition-specification-prediction program, and for re-training the model (M2, M3) of the composition-quality-prediction-program or of the composition-specification-prediction program on the extended training data for obtaining an improved version of the model M2+, M3+.

According to embodiments, the method comprises:
  applying a defect-identification program on the returned image for identifying measures of one or more defects in the coating surface depicted in the returned image and for computing a qualitative and/or quantitative characterization of the said coating surface; for example, the defect-identification program may initially be obtained by training a machine-learning model on manually annotated images of coating surfaces;
  storing the qualitative and/or quantitative characterizations in the database for providing an extended database; and
  re-training the predictive model (M2, M3) on the associations of the characterizations and the coating composition associated parameters (components, absolute and/or relative component amounts, manufacturing process parameters and/or application process parameters) in the extended database for providing an improved version of the predictive model; and
  replacing the predictive model (M2) of the composition-quality-prediction program and/or the predictive model (M3) of the composition-specification-prediction program with the improved version of the predictive model.

Hence, in the context of an automated facility for manufacturing and testing a coating composition, the composition-quality-prediction-program may be used for predicting many promising candidate compositions, the facility may be used for manufacturing and testing the real properties of these candidate compositions, including the coating surface quality, and the obtained test data may be used for improving the predictive model M2 of the composition-quality-prediction program and/or the predictive model M3 of the composition-specification-prediction program. Hence, in the course of time, the integrated system comprising the facility and the composition-quality-prediction-program (and/or composition-specification-prediction) have the potential of mutual enhancement and improvement.

According to embodiments, the training process involves an active learning module. The method further comprises:
  a. performing the training of the predictive model on the associations of the measures and the coating components in the database for providing the trained predictive model (M2, M3), where a loss function is minimized for the training,
  b. testing to determine whether the value of the loss function obtained for the predictive model meets a specified criterion,
    whereby selectively, in the event that the criterion is not met, the following steps are carried out:
      i. selection of a candidate coating composition specification from a plurality of candidate coating composition specifications by the active learning module, the selected candidate composition specification specifying the one of the candidate compositions determined to provide the highest learning effect of the predictive model (M2, M3) regarding the correlation of qualitative and/or quantitative coating surface characterizations and one or more parameters selected from a group comprising coating components, component amounts, manufacturing process parameters and/or application process parameters of the coating composition;
      ii. driving the facility by the computer system for automatically producing the candidate coating composition in accordance with the selected specification, for automatically applying the produced candidate composition on a substrate and for automatically acquiring an image of the surface with the applied coating composition;
  iii. applying the defects-identification program on the image acquired in step ii for computing and storing a qualitative and/or quantitative characterization of the coating surface depicted in said image in the database, thereby extending the database;
  iv. re-training of the predictive model (M2, M3) on the extended database for providing an improved version of the predictive model,
  v. repeated execution of step b using the improved version of the predictive model,
c. replacing the predictive model (M2) of the composition-quality-prediction program with the improved version of the predictive model and/or replacing the predictive model (M3) of the composition-specification-prediction program with the improved version of the predictive model.

The use of an active learning module may have the advantage that the learning effect during the training or re-training of the model M2 is improved and accelerated: the active learning module is adapted to identify the ones of the candidate coating composition the testing and storing of whose properties would allow improving the quality of the predictive model M2 the most.

Using of the adaptive learning module may be beneficial in the context of a situation in which obtaining manufacturing and empirically testing a coating composition is expensive. In such a scenario, the active learning module can actively identify the most promising candidate compositions and can actively query for manufacturing and testing these identified candidate compositions. Since the active learner chooses the most promising candidate composition, the number of compositions to be manufactured and tested to learn a concept can hence be much lower than the number required in normal supervised learning.

According to embodiments, active learning is used during the training of the predictive model M1 to be used for identifying coating defects in digital images of coating surfaces. In this case, the active learner identifies a subset of one or more of a plurality of unlabeled test images of coating surfaces whose manual annotation would provide the highest learning effect. The active learning module prompts a user to manually annotate (assign labels) to each image of the subset, whereby the label indicates type and location of the coating defect depicted therein. These one or more additionally labeled images are added to the training images, thereby extending the training data. The predictive model M1 is re-trained on the extended training data, thereby providing an improved, more accurate version of the predictive model M1. Then, the outdated predictive model in the defect-identification program is replaced by the improved version of the model.

In a further aspect, the invention relates to a system comprising:
  a facility for producing and testing compositions for paints, varnishes, printing inks, grinding resins, pigment concentrates or other coating materials, where the facility comprises at least two workstations, where the at least two workstations are connected to one another via a transport system on which self-propelled transport vehicles are able to run for transporting the components of the composition and/or of the composition produced between the workstations, and a computer system configured to perform the method of any one of the embodiments described herein.

In a further aspect, the invention relates to a computer program configured to perform the method of any one of the embodiments described herein.

In a further aspect, the invention relates to a defect-identification program provided by performing a method of providing and using the defect-identification program as described herein for embodiments of the invention.

In a further aspect, the invention relates to a distributed data processing system comprising a monolithic or distributed data processing system and a camera. The distributed or monolithic data processing system comprises a defect-identification program as described herein for embodiments of the invention adapted to identify coating defects in digital images of coating surfaces acquired by the camera. For example, the data processing system can be a monolithic data processing system, e.g. a general-purpose data processing system such as a computer or a smartphone or can be a surface-quality-control-related-special-purpose device. Alternatively, the data processing system can be a distributed data processing system, e.g. a cloud system or a client-server system comprising a server computer and one or more client data processing systems.

In a further aspect, the invention relates to a composition-quality prediction program provided by performing a method of providing and using the composition-quality prediction program as described herein for embodiments of the invention.

In a further aspect, the invention relates to a composition-specification-prediction program provided by performing a method of providing and using the composition-specification-prediction program as described herein for embodiments of the invention.

In a further aspect, the invention relates to a coating-composition manufactured in accordance with a specification of a composition provided by performing a method of any one of the embodiments for providing a specification of a coating composition described herein. In particular, the specification can be computed according to embodiments of the invention by the coating-composition-specification-prediction program based on a desired coating surface characterization provided as input using a trained model (M3).

In a further aspect, the invention relates to a specification of a composition provided by performing a method of any one of the embodiments for providing a specification of a coating composition described herein.

In a further aspect, the invention relates to a volatile or non-volatile data storage medium comprising computer-interpretable instructions implementing the defects-identification program, the composition-quality-prediction program and/or the composition-specification-prediction program.

In a further aspect, the invention relates to a volatile or non-volatile data storage medium comprising the above-mentioned specification, the data storage medium being operatively coupled via an interface to a facility, the facility being configured for producing coating compositions in accordance with one or more specifications stored in the data storage medium.

A "coating surface" as used herein is a surface of a substrate having been coated one or multiple times with a coating composition. For example, the coating composition can be applied by spreading or spraying or painting the coating composition onto the substrate, by immersing at least one surface of the substrate in the coating composition, or by other coating approaches.

A "coating defect" or "coating surface defect" as used herein is any optically detectable deviation of a coating surface from a typical or desired appearance of the coating surface. An image defect resulting e.g. from dust on an optic lens of the camera is not a coating defect.

A "program" as used herein is a piece of software, e.g. an application program or a module or function of an application program, or a script, or any other kind of software code that is executable by one or more processors, e.g. CPUs or GPUs. A program can be, for example, an application program. Application programs, in particular programs designed for execution on portable devices, can be implemented in the form of an "app".

A "defect-identification program" as used herein is a software program or software module configured to analyze digital images for automatically identifying one or more coating defects and for computing a coating surface characterization as a function of the identified coating defects in the surface depicted in the image.

A "composition-quality prediction program" as used herein is a software program or software module configured to receive a (complete or incomplete) specification of a coating composition and is configured to predict one or more properties of the coating composition as a function of the data specified in the specification. The properties of the coating composition can comprise an indication of the quality of the coating composition, e.g. an indication of the quality of a coating surface obtained by applying the coating composition on a substrate. The quality indication may be, for example, the likelihood of generating certain types of coating defects.

A "composition-specification prediction program" as used herein is a software program or software module configured to receive a desired coating surface characterization as input parameter(s). Optionally, the composition-specification prediction program can be configured to receive one or more further input parameters such as an incomplete specification of a coating composition for limiting the solution space of the prediction. The composition-specification prediction program is configured to predict one or more of the following output parameters as a function of the received input data: one or more components, one or more absolute or relative component amounts, one or more manufacturing process parameters and/or one or more application process parameters.

A "measure" of a defect as used herein is any qualitative or quantitative parameter value or set of parameter values being descriptive of a property of a coating defect. Examples for a qualitative defect measure is a defect type label such as "bubble defect", "delamination defect", "foam defect" and the like. Examples for a quantitative measure of a coating defect are "% of coating surface covered by the defect", "number of bubbles in an image", "numbers of bubbles per area for the defect", "average size of bubbles", and the like. A measure of a defect can be a single parameter value or a set of parameter values, e.g. property of an individual defect instance or a property derived from multiple defect type instances, e.g. an average bubble defect instance diameter or a histogram being indicative of the size distribution of multiple defect instances, e.g. bubbles. A measure of a defect can be obtained e.g. by analyzing the dimensions or other properties of the identified defects (e.g. based on surrounding bounding boxes and/or based on individual pixels). A measure of a defect can be a parameter value, or a set of parameter values obtained by applying arithmetic operations, e.g. for obtaining an average diameter, or by complex statistical calculations, e.g. a mathematical formula characterizing a distribution of the size and positional distance of bubbles in a coating surface, a histogram, or the like.

A "characterization of a coating surface" as used herein is any qualitative or quantitative parameter value or set of parameter values being descriptive of the quality of a coating of a surface. The coating surface quality depends on the measures of one or more defects comprised in the coating surface. For example, a characterization of a coating surface can be identical to qualitative and/or quantitative measures of one or more defects comprised in the coating surface. According to other examples, the characterization of the coating surface is obtained by aggregating the measures of multiple defects in the coating surface. For example, in case the coating surface comprises three bubble defects BD1, BD2, BD3, the aggregated coating surface characterization can be the fraction of the depicted surface covered by the totality of the identified bubble defects, e.g. "5% bubble defect area". The aggregation function can be, for example, an arithmetic or geometric mean (e.g. for computing average bubble diameters), a sum, a product, or more complex arithmetic and/or statistic aggregation functions. A characterization of a coating surface can comprise a combination of two or more qualitative and/or quantitative characterizations. For example, the characterization can be a combination of an indication of the defect type with an extent of the defect, e.g. "coating surface with a severe bubble defects", or "coating surface with medium-grade bubble defects" or "coating surface with minor bubble defects". The extent may be provided in the form of a numerical value, e.g. % of the area covered by the defects, or an indication of a value range, a histogram, or the like. A characterization of a coating surface can comprise a combination of qualitative and/or quantitative characterizations obtained for each of two or more different types of defects respectively.

The term "composition" or "coating composition" as used herein is a composition which comprises two or more raw materials ('components') from which the composition is formed and which is to be applied on a substrate to provide a coating surface. When in the context of this application reference is made to the production or testing of a composition by an automated facility, this is to be understood that the coating composition is produced according to information on the nature and/or amount of the components.

The term "candidate composition" or "candidate coating composition" as used herein is a coating composition which has not yet been prepared and/or tested and whose properties are therefore at least partially unknown at the moment when the candidate coating composition is specified. For example, a candidate composition may be a composition that has been manually or automatically specified but which has not yet been prepared and tested. Accordingly, the properties of this composition are not known.

A "specification of a composition" as used herein is a data set comprising parameters related to a coating composition. For example, the parameters can indicate the identity and/or substance class of some or all components to be combined for manufacturing a coating composition. Optionally, the specification may comprise additional parameters, e.g. the relative or absolute amounts or amount ranges of the respective components, coating composition manufacturing process parameters, coating application process parameters, and the like. These parameters may specify how the components have to be processed and/or mixed for obtaining the composition and/or how the composition is to be applied on a substrate to obtain a particular coating surface. The specification of a composition may be complete or incomplete. For example, some specifications may only indicate the type of a component (e.g. organic-solvent based solvating agent) but not the exact identity and/or amount of the component. The "specification" of a composition may be provided in various forms, e.g. as printout, as file, e.g. an XML file, an object of an object-oriented programming language, as JSON file or the like.

A "coating composition manufacturing process parameter" or "manufacturing process parameter" as used herein is a parameter being indicative of properties of a process of processing and/or combining the components to form a coating composition. Examples are mixing duration, mixing speed, mixing temperature, sequence of mixing components, equipment used for mixing or otherwise preparing the coating composition or the like.

A "coating composition application process parameter" or "application process parameter" as used herein is a parameter being indicative of properties of a process of applying a coating composition on a substrate. Examples are indications of the application technique (spraying, spreading, painting, immersing, etc.), the duration of the application (e.g. immersion time), number of repeated applications, pre-treatment steps of the substrate (drying, priming, cleaning, heating, etc.), the equipment used for applying the coating composition and/or the nature of the substrate (wood, plastic, metal, cardboard, etc.).

A "known composition" as used herein is a composition whose properties (e.g. coating surface characterizations, rheological properties, elasticity, shelf-life etc.) are known at the time of training of a neural network to the person conducting the training. For example, the known composition may have been produced for a customer several months or years ago and the properties of that product have been measured empirically. The measurement does not necessarily have to have been carried out by the operator of the laboratory which now determines the predictive composition, but may also have been carried out and published by other laboratories, so that in this case the properties are taken from the specialist literature. Since a composition according to the above definition also contains formulations as a subset, the "known compositions" according to the embodiments of the invention may also contain "known formulations" or be "known formulations".

The term "defoaming" is frequently used to describe the removal of gas bubbles from the composition or the coating. However, in certain cases the terms "defoaming" and "air release" should be differentiated. First, the gas bubbles need to reach the surface. Removing the foam bubbles that are at the surface is called defoaming (in the strict sense). Defoamers (in the strict sense) are only effective at the surface where they eliminate the air bubbles located there. In comparison, air release agents take effect throughout the coating film. In the present case, the term "defoamers" is used broadly and covers both the defoamers in the strict sense and the air release agents.

A "database" as used herein is any volatile or non-volatile data storage medium in which data, in particular structured data, is stored. The database can be one or more text files, spreadsheet files, a directory in a directory tree, or a database of a relational database management system (DBMS) such as MySQL or PostgreSQL.

A "loss function" of a prediction problem as used herein is a function that is used in the training of a predictive model (e.g. a model of a neural network) by a machine learning program for training and improving the model. The loss function outputs a value whose magnitude gives an indication of the quality of the predictive model, whereby the loss function is minimized in the course of the training, since the magnitude of this value indicates the inaccuracy of the predictions of the predictive model.

A "facility" for the production and testing of compositions as used herein is an apparatus or system comprising several laboratory devices and a transport unit, which is capable of jointly controlling the laboratory devices and the transport unit in an orchestrated manner in order to carry out a workflow automatically or semi-automatically. The workflow can be, for example, a coating composition preparation workflow (e.g. a combine-and-mix workflow), or an analysis workflow or a combination of two or more of these workflows. The workflow can comprise automatically preparing a coating composition and/or automatically applying the composition on one or more substrates and/or automatically obtaining and processing digital images of the coating surface of the substrate(s). The facility can be, for example, a high-throughput facility (HT-facility), also referred to as "high-throughput equipment" (HTE).

The "testing" or "analysis" of a coating composition by an automated manufacturing and/or testing facility is the process of analyzing chemical, physical, mechanical, optical or other empirically measurable properties of the composition by means of one or more analysis modules. For example, the testing may comprise applying a composition on a substrate, acquiring and analyzing a digital image of the coating surface, and computing a quality measure of the coating as a function of one or more defects detected in the digital image of the coating surface. The analysis may further comprise measuring further object properties, e.g. opaqueness, elasticity, rheological properties, color, etc.

An "active learning module" as used herein is a software program or a module of a software program which is designed to select a (comparatively small) subset of candidate compositions from a set of candidate compositions in such a way that a particularly strong learning effect occurs after the preparation and empirical measurement of the properties of this selected candidate composition as a consequence of the consideration of these data in training the predictive model.

A "model" or "predictive model" as used herein is a data structure or executable software program or program module configured to generate a prediction based on input data. For example, the model can be a model obtained in a machine-learning process by training the model on manually and/or automatically annotated training data. A predictive model as used herein may also comprise a collection of two or more functionally integrated models, e.g. a set of models used and/or comprised in an application program. The predictive model can be, for example, a neural network model, a support vector model, a random forest, a decision tree, or the like. According to embodiments of the invention a predictive model adapted to compute a characterization of a coating surface in respect to the presence, location and/or extent of one or more coating defects based on digital image data is also referred to as "M1" model. A predictive model adapted to predict a property of a coating composition, in particular a characterization of a coating surface generated based on this composition, based on one or more input parameters related to e.g. the components, component amounts, manufacturing process parameters and/or application process parameters of this composition is also referred to as "M2" model. A predictive model adapted to predict on one or more parameters related to e.g. the components, component amounts, manufacturing process parameters and/or application process parameters of a coating composition based on input data specifying a desired property of a coating composition, in particular a desired characterization of a coating surface generated based on this composition, is also referred to as "M3" model. According to embodiments, the model M3 is configured to take into account an incomplete coating composition specification as additional input data, whereby the incomplete coating composition may be used to limit the solution space of the prediction to be provided by the model M3.

BRIEF DESCRIPTION OF THE DRAWINGS

In the following, only exemplary forms of the invention are explained in more detail, whereby reference is made to the drawings in which they are contained. They show:

FIG. 8A a plurality of coating compositions;

FIG. 8B a "draw down" coating application unit;

FIG. 8C a "spraying" coating application unit;

FIG. 8D an automated conveyor belt for transporting coating samples in a HTE;

DETAILED DESCRIPTION

Figure 1:
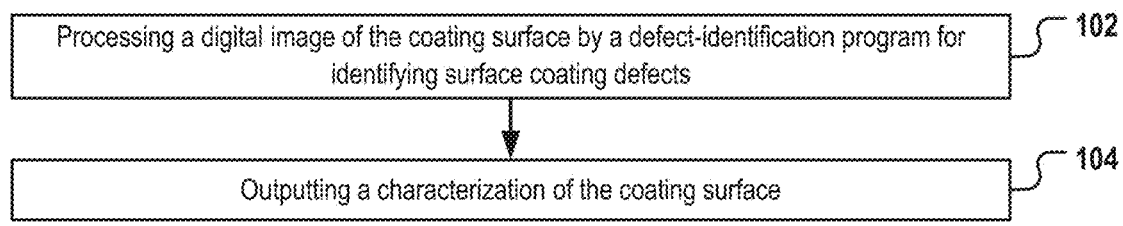
FIG. 1 a flowchart of a method for automated characterization of a coating surface.

FIG. 1 shows a flow chart of a method for automated characterization of a coating surface. In a first step 102, a defect-identification program processes a digital image depicting a coating surface. The defect-identification program identifies one or more coating defects and provides a characterization of the recognized effects in step 102. For example, the program may determine that the coating surface comprises a first bubble defect region comprising about 100 bubbles and a second bubble defect region comprising about 400 bubbles. The characterization of the recognized effect may comprise the type, location and extent of the identified defects. The data obtained in step 104 may be output to a user and/or may be used internally by the defect-identification program for computing derivative data values, e.g. aggregated coating surface characterizations.

Figure 2:
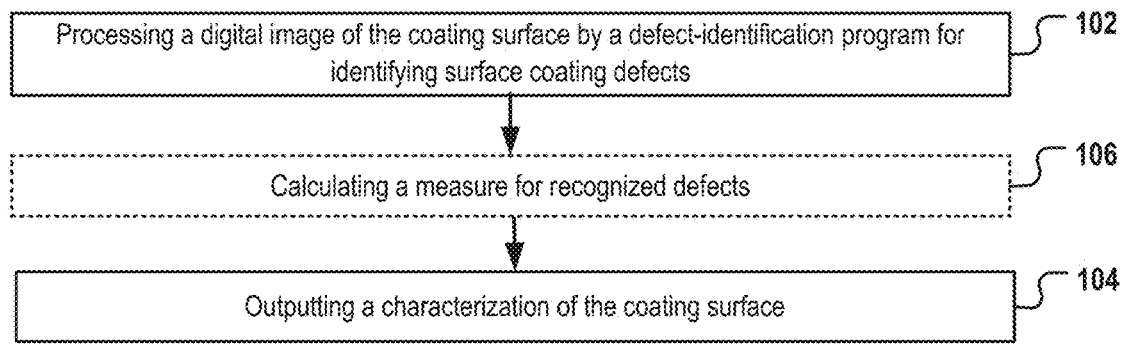
FIG. 2 a flowchart of a method for automated characterization of a coating surface in greater detail.

FIG. 2 shows a flowchart of a method for automated characterization of a coating surface in greater detail. After steps 102 and 104, the defect-identification program in step 106 computes measures of the individual defects, e.g. size, shape, spatial distribution, size distribution or the like. The defect-identification program uses these measures in step 108 to compute and provide a qualitative and/or quantitative characterization of the coating surface.

Figure 3:
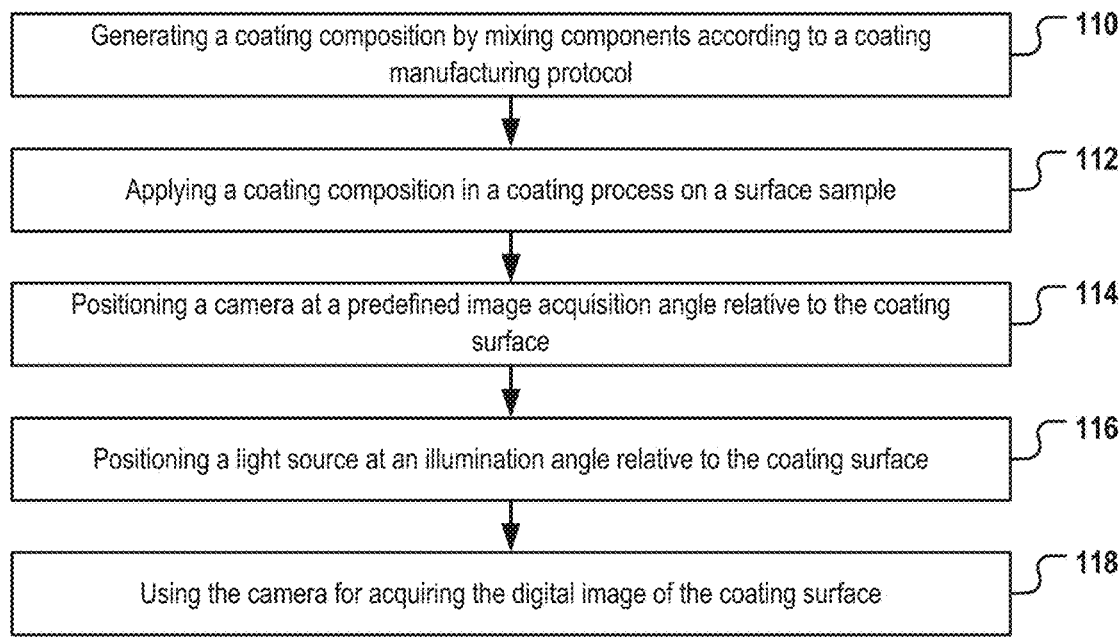
FIG. 3 a flowchart of a method for coating a surface and for obtaining an image of a coated surface.

FIG. 3 shows a flowchart of a method for coating a substrate and for obtaining an image of the substrate's coated surface. In step 110, a plurality of coating compositions is generated by mixing multiple components with each other according to a mixing and manufacturing protocol. In step 112, a coating composition is applied in accordance with a coating application protocol on one or more substrate samples. The samples are transported automatically or manually to an image acquisition unit. In steps 114 and 118, a camera, an optional light source and the coated sample are positioned relative to each other in a defined manner as to enable an image analysis software 124 to correctly analyze the images. Then, one or more images depicting the coated sample surface are taken in step 118.

Figure 4:
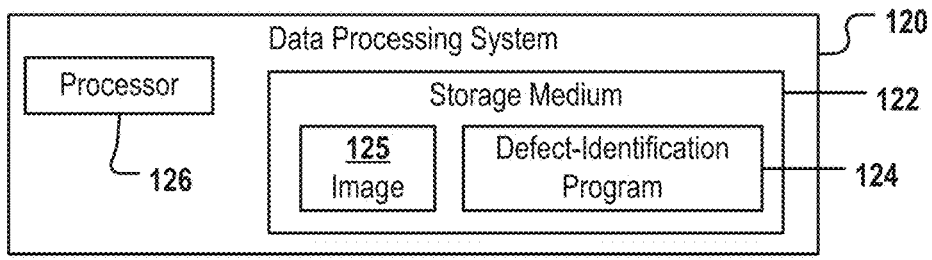
FIG. 4 a block diagram of a data processing system for automated coating surface characterization.

FIG. 4 shows a block diagram of a data processing system 120 for automated coating surface characterization. The data processing system comprises one or more processors 126 and a volatile or nonvolatile storage medium 122. The storage medium can comprise images 125, e.g. training images for training the model M1 of the defect-identification program 124 or test images to be input to the already trained predictive model M1. In addition, or alternatively, the storage medium can comprise training data for training the model M2 of the composition-quality prediction program and/or can comprise the composition-quality prediction program comprising an already trained predictive model M2.

In addition, or alternatively, the storage medium can comprise an untrained version of the model M3 of the composition-specification prediction program and/or can comprise the composition-specification prediction program comprising an already trained predictive model M3.

The data processing system 120 can be implemented in many different ways. For example, the data processing system can be a monolithic computer system, e.g. a desktop computer system, a portable telecommunication device, a smart phone, a special purpose coating surface-quality control device or a computer system being operatively coupled to or being an integral part of a facility for automatically manufacturing and/or testing coating compositions. Alternatively, the data processing system 120 can be a distributed computer system, e.g. a client/server computer system optionally coupled to one or more facilities for automated manufacturing and/or testing of coating compositions. The components of the distributed computer system can be communicatively linked with each other via a network connection, e.g. the Internet or an intranet of an organization. FIGS. 5A-5D illustrate some implementation examples of the data processing system 120.

Figure 5A:
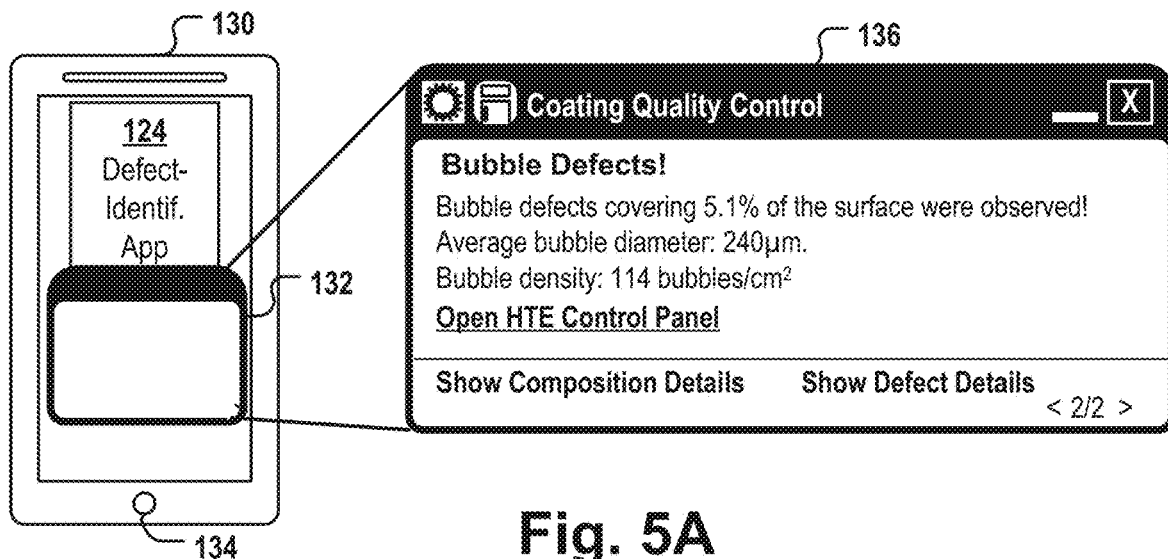
FIG. 5A a data processing system in the form of a smart phone comprising a locally installed app.

FIG. 5A shows a data processing system in the form of a smart phone 130. The smart phone comprises the defect-identification program in the form of a locally installed application program, also referred to as "app" 124.

For example, the app may comprise a graphical user interface 132 which allows a user to control the camera 134 of the smart phone as to take an image of a coated sample surface at an appropriate distance and position relative to the coated surface. The successful acquisition of the digital image may automatically trigger the defect identification app 124 to analyze the image and to identify one or more coating defects depicted in the image. Preferably, the app 124 is configured to generate the further GUI 136 informing a user on the result of the processing. For example, GUI 136 may indicate the type of identified defects (bubble defects) and one or more quantitative measures of the defects (e.g. average bubble diameter, bubble density, etc.) In addition, the GUI 136 comprises a characterization of the coating surface computed as a function of the properties of the one or more identified coating defects. For example, the defect-identification program can be configured to compute, based on the sizes and number of the identified bubbles, the total size of the area of the surface covered with bubbles.

Using a smart phone app for acquiring images of coating surfaces and for automatically identifying coating defects may have the advantage that it is not necessary to equip the employees of a company with extensive special-purpose devices in order to obtain an objective, reproducible quality measure for coating surfaces. It is sufficient to download and install an app.

Figure 5B:
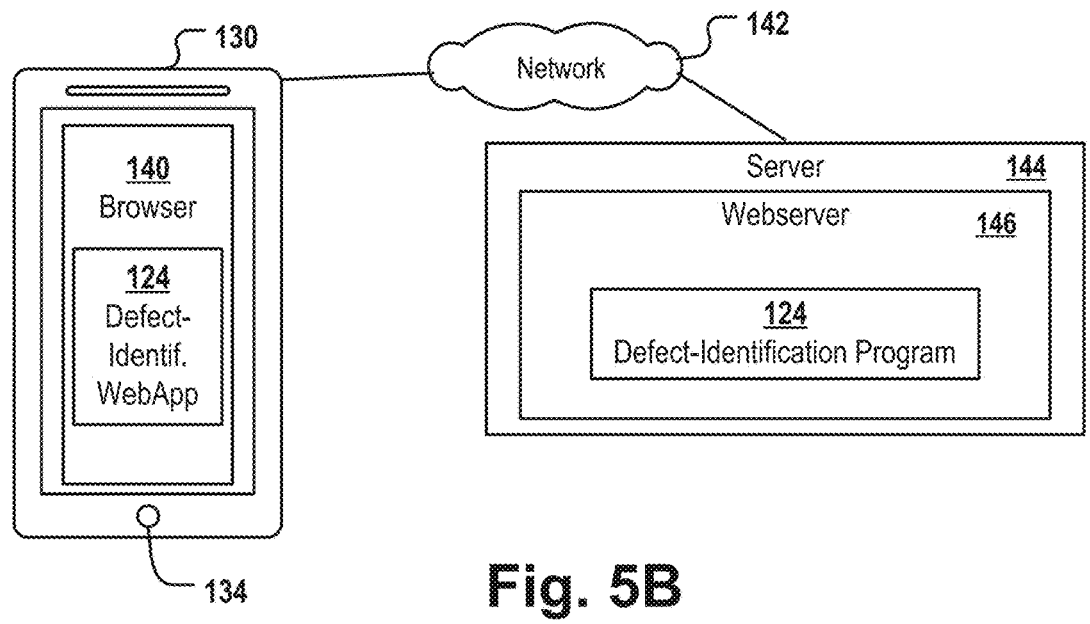
FIG. 5B a data processing system in the form of a smart phone comprising a web-application.

FIG. 5B shows a data processing system in the form of a smart phone 130 comprising the defect-identification program 124 in the form of a web-application.

According to one example, the defect-identification program is implemented as a script that runs in the browser of the smartphone and that is downloaded by a user visiting a particular website, e.g. a web portal of a company generated by a server 144 and offered via the Internet or intranet. For example, the program 124 can be implemented as JavaScript program.

According to another embodiment, the defect-identification program is implemented as a program running outside of a browser, e.g. a Java program.

The defect-identification program can be implemented as a two-component program comprising a client portion and a server portion which are interoperable and are configured to exchange data via a network connection 142. For example, the program portion installed on the portable telecommunication device 130 ("client application") can be configured to controlling the image acquisition process and for outputting the defect identification results to a user. The program portion installed on the server ("server application") can be configured to receive the digital image from the client portion via the network, to analyze the digital images for detecting coating defects, for determining measures of the identified defects and for computing a qualitative and/or quantitative characterization of the depicted coating surface. The server portion returns the characterization and preferably also the measures and an indication of the type and extent of the identified defects to the client portion.

Figure 5C:
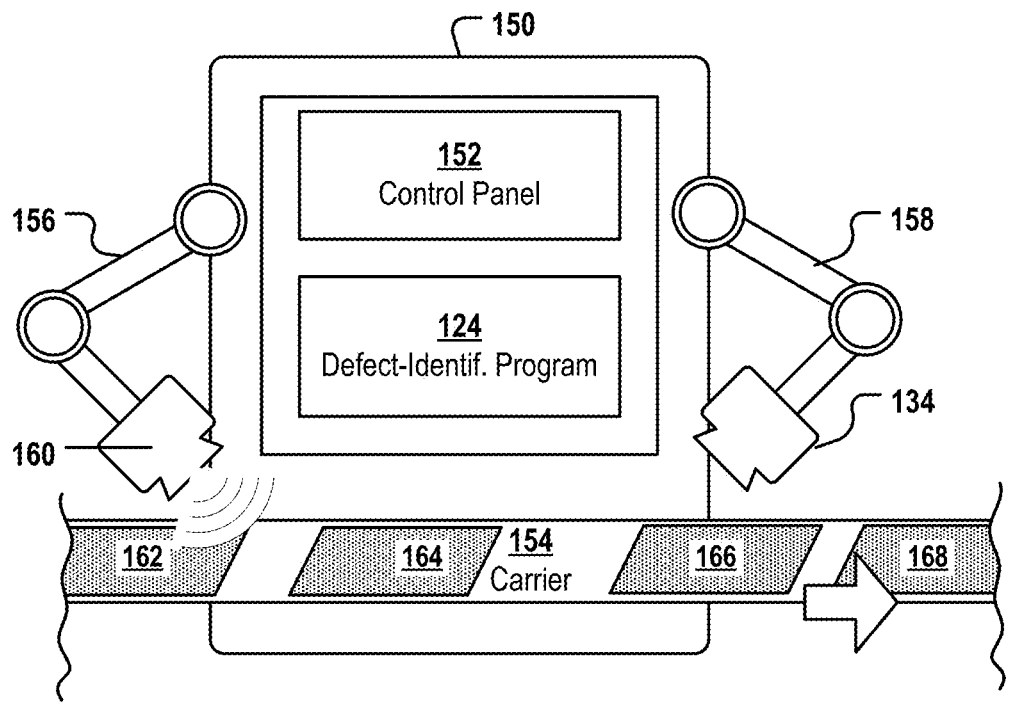
FIG. 5C a data processing system in the form of a customized coating surface quality control device.

FIG. 5C shows a data processing system 150 in the form of a customized coating surface quality control device, i.e., a dedicated hardware designed for controlling and objectivizing the quality of coating surfaces and, implicitly, the quality of the coating composition and/or the coating process. The device comprises a storage medium with the defect-identification program 124, an interface 152 allowing a user to control a testing process and output the test result, and preferably several hardware components used for the purpose of testing the surface properties of coated samples. For example, the device can comprise a camera 134 coupled to the device via a robotic arm 158 or via other connecting elements which allow to modify the relative position of camera and coated sample. The device can comprise one or more light sources 160 which are preferably also coupled to the device via movable and/or rotatable connecting elements, e.g. a robotic arm 156.

The quality control device 150 can be implemented as portable device or as stationary device. For example, the device can be implemented as an integral part of a facility for automatically manufacturing and/or testing coating compositions. The facility comprises a conveyor belt 154 for transporting a plurality of coated samples 162, 164, 166, 168 to the control device 150, thereby enabling a fully automated, fast and reproducible quality control of many coating surfaces.

Figure 5D:
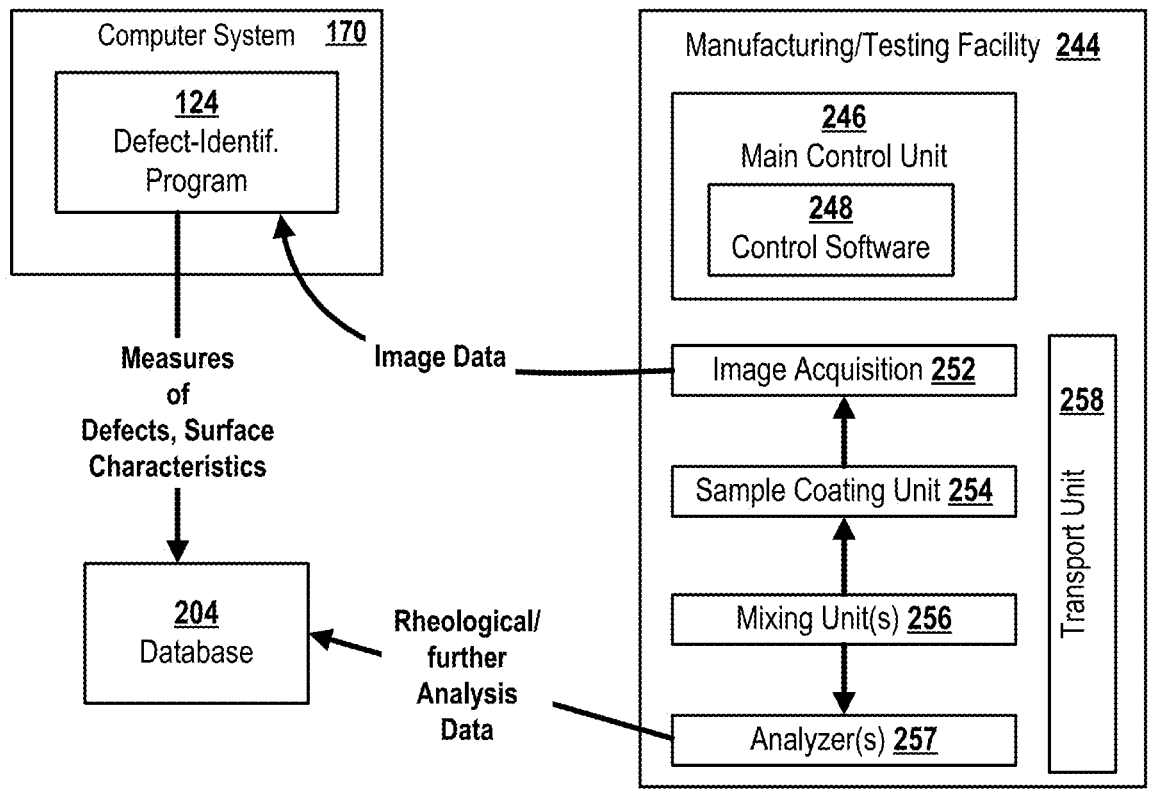
FIG. 5D a data processing system in the form of a computer coupled to a facility for manufacturing coating compositions.

FIG. 5D shows a data processing system in the form of a computer 170 coupled to a facility 244 for manufacturing coating compositions.

The facility 244 comprises a main control computer 246 for controlling, monitoring and/or orchestrating various tasks related to the manufacturing of coating compositions, related to the application of coating compositions on various surfaces and/or related to the testing of the coated surfaces or of the coating compositions (e.g. for determining rheological, chemical, physical or other parameters of the coating composition). The respective tasks are performed by several different units comprised by the facility 244. For example, the facility can comprise one or more analyzers 257 for performing chemical, physical, mechanical, optical or other forms of tests and analysis on coating compositions or on substrate surfaces having been coated with a coating composition. The facility can comprise one or more mixing units 256 configured for manufacturing various coating compositions, e.g. by mixing the components of a composition based on a specific manufacturing and mixing protocol. The facility can comprise one or more sample coating units 254 configured for automatically coating surface samples. For example, the coating units 254 can comprise a "spraying" coating application unit or a draw down" coating application unit as depicted, for example, in FIGS. 8C and 8B. According to some example implementations, the facility further comprises an image acquisition unit 252 comprising a camera and a light source and means for positioning the sample and the camera and/or light source relative to each other such that the acquired digital images can be used as input by the defect-identification program 124. One or more transport units 258, e.g. conveyor belts, connect the different units and carry components, mixtures, coating compositions and coated samples from one unit to the other.

The control computer 246 comprises a control unit 248 configured for sending the digital images of coated samples acquired in the image acquisition unit 252 to the defect-identification program 124 of the computer system 170. According to some embodiments, additional parameters are provided together with the image data to the defect-identification program. The parameters may indicate the identity, relative and/or absolute amounts of one or more components of the coating composition used for coating a sample, and optionally also manufacturing process parameters and/or application process parameters. The parameters can be provided in the form of a complete or incomplete specification of the coating composition and/or the respective manufacturing or application process parameters.

The defect-identification program is configured to use the received image, and optionally also the parameters, as input for automatically identifying coating defects depicted in the image, for computing defect measures and for computing coating surface characterizations the function of the defect measures. The results computed by the defect-identification program can be output to a user via a GUI and/or can be stored in the database 204.

Preferably, parts of the data obtained by the other units such as the analyzers 257 or the mixing units 256 or the coating units 254 can be stored directly in the database in association with an identifier of a particular coating composition and/or with an identifier of coated samples or can be sent to the computer system 170 to have the computer system 170 store the data in the database.

Using the defect-identification program in the context of the facility 244 can be particularly advantageous, because after the images of the coating surfaces have been taken, they can be automatically analyzed for the defects to be examined. The result obtained can be linked to the formulation data and/or analysis data and thus be used to optimize the composition.

Figure 6:
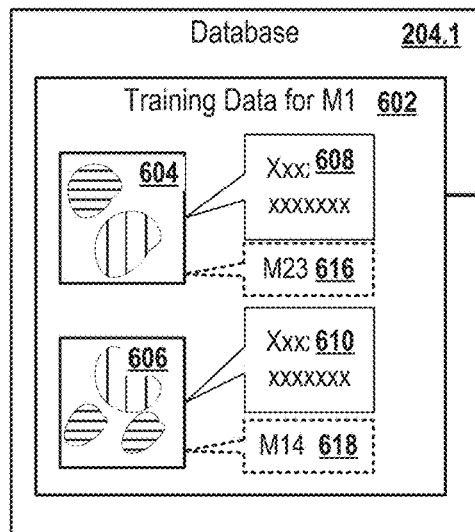
FIG. 6 an illustration of the training and test phase for generating and using the defect-identification program.
Figure 6:
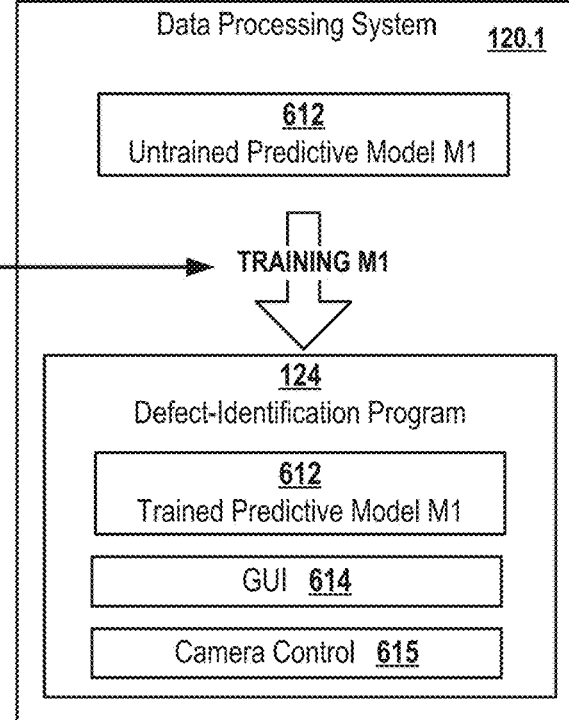
Figure 6:
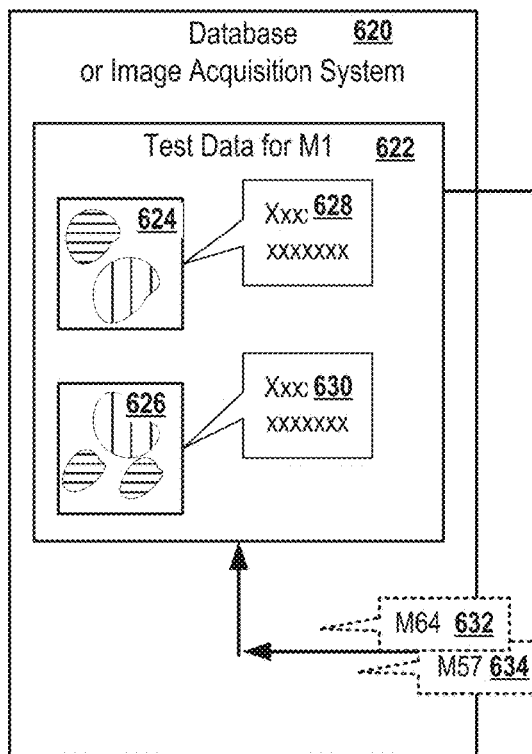
Figure 6:
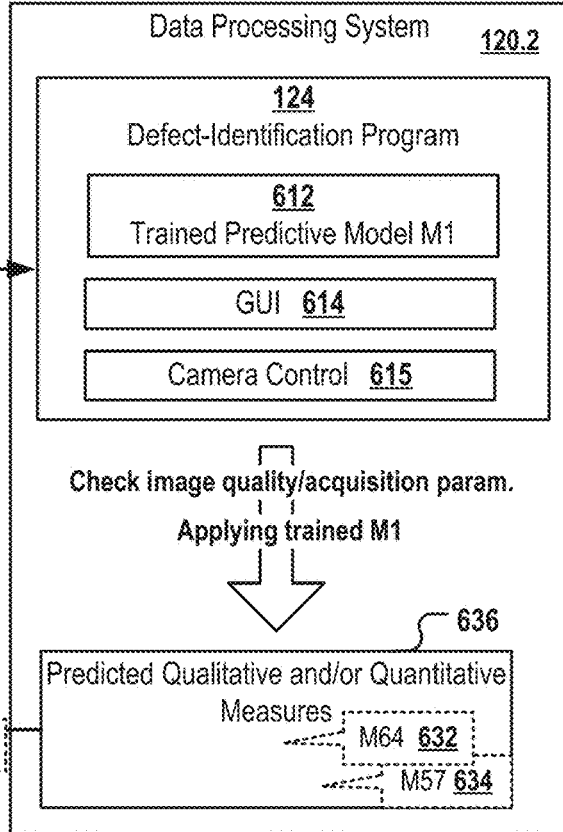

FIG. 6 shows an illustration of the training and test phase for generating and using the defect-identification program.

In a first step, a training data set 602 is generated. For this purpose, a plurality of different coating compositions is prepared. The different coating compositions vary in respect to the nature of their components, the amounts of the respective components, and/or in respect to manufacturing process parameters. The multiple coating compositions are then applied on substrates in order to generate a plurality of coating surfaces. The number of coated samples can be much larger than the number of coating compositions, because the same coating composition can be applied on many different types of material (wood, plastic, cardboard, metal etc.), via many different types of coating techniques (spraying, painting, immersing, spreading, etc.). Then, one or more digital images 604, 606 are acquired for each of the coated samples. For example, for a particular coating sample, digital images can be obtained by varying illumination strengths, the relative position of the light sources, the light wavelength, and the like.

Depending on the coating composition, the material of the sample, the coating process parameters and many other factors, the coating surfaces depicted in the images may comprise one or more coating defects of different predefined defect types.

In the next step, the defects depicted in the acquired digital images are labeled manually. For example, the labeling process can be performed as described with reference to FIG. 9B.

The digital image 604 can be annotated with labels 616 being indicative of the location, type and preferably also the extent of each coating defect depicted in the image 604. The labeled 616 also comprises a qualitative and/or quantitative characterization of the image 604, e.g. "overall quality level 7 comprising bubble defects of grade 2 and wrinkling defects of grade 8". Preferably, the image 604 is stored in association with additional data 608. The additional data 608 can comprise a complete or incomplete specification of the components of the coating composition used for generating the depicted coating surface, whereby the specification may in addition comprise component names and/or amounts, manufacturing process parameters and/or composition application process parameters. For example, a specification of a composition and the above-mentioned parameters can be stored in a database in association with an identifier of the coating composition used for generating the depicted coating surface. The image 604 can have an image ID stored in association with an identifier of the coated sample depicted in the image, whereby the identifier of the coated sample stored in association with an identifier of the coating composition used for coating the sample.

The digital image 606 can be annotated with labels 618 and stored in association with additional data 610 analogously.

A computer system 120.1 is provided comprising an untrained version of a predictive model 612 that is to be trained. The computer system has access to the database 204 comprising the training data. The training data 602 is used as input during the training process. In the training process, the predictive model M1 learns correlations between pixel patterns in the annotated images 604, 606 and coating defects/coating surface characterizations.

According to embodiments, the training data comprises additional data 608, 610 in the form of parameters. The predictive model M1 (or further predictive models M1.2 comprised in the defect-identification program) will also learn correlations between pixel patterns, coating defects/coating surface characterizations and the additional data such as the components and/or amounts of the composition components, manufacturing process parameters and/or application process parameters.

The untrained model can be implemented in the form of a neural network. The neural network preferably comprises a region proposal network, e.g. a region proposal network provided by the Mask R-CNN program.

As a result of the training, a predictive model M1 (which may comprise one or more further predictive models M1.2) 612 is provided having learned the above-mentioned correlations. The trained model can be integrated in a defect-identification program 124 and used for automatically identifying coating defects depicted in digital images. The program 124 may comprise additional functionalities, e.g. a GUI 614 for assisting a user in acquiring images during training and/or test phase and/or for displaying the prediction result to a user, e.g. in the form of numerical values and/or segmented images.

The lower part of FIG. 6 shows the test phase of the already trained model M1. During the test phase, a plurality of digital images of coating surfaces referred to as "test images" are provided. For example, the test images 624, 626 can be stored in the same database 620 or in a different database used for storing the training images. The test images do not comprise any label at first. Optionally, the test images can be stored in association with additional data 628, 630, in particular a complete or incomplete specification of the nature and/or amounts of the components of the coating compositions, various manufacturing protocol parameters, coating composition application process parameters and/or image acquisition system parameters.

In addition, a computer system 120.2 is provided on which a copy of the defect-identification program 124 is installed and/or instantiated. The computer system 120.1 used for training the model can be the same computer system 120.2 used for applying the trained model on test images or can be a different computer system to which a copy of the defect-identification program was provided.

The defect-identification program 124 comprising the trained predictive model M1 612 receives one or more test images 624, 626 which are used as input for predicting a qualitative and/or quantitative characterization 632, 634 of the coating surface depicted in the respective test image. For example, the defect-identification program can perform a pixelwise image analysis for identifying the location, type and extent of coating defects depicted in the image. Then, the program can analyze the obtained data for computing measures of each coating defect identified in an image. For example, the fraction of pixels representing bubble defects and the fraction of pixels of the same image representing a delamination defect can be determined. In a further step, these measures are used for computing an aggregate characterization of the coating surface, e.g. a label such as "bubble defect grade 3" as a function of the defect measures.

Optionally, the additional data 628, 630 assigned to the respective test image is received and used by the defect-identification program as additional input for performing the prediction.

Preferably, the automatically predicted measures and characterizations 632, 634 are stored in association with the respective test images 628, 613 in the database.

Thereby, data is provided comprising labels which are indicative of coating surface characterizations and hence, the coating quality of a particular coating composition or protocol. The data can be used for increasing the training data for model M1 602 and for retraining the predictive model based on the extended database to improve accuracy. In addition, or alternatively, the data can also be used for training another predictive model M2 with a different scope of prediction as explained with reference to FIG. 7.

Figure 7:
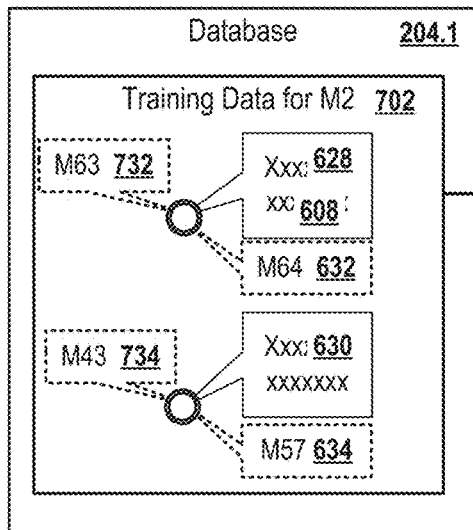
FIG. 7 an illustration of the training and test phase for generating and using the composition-quality prediction program.
Figure 7:
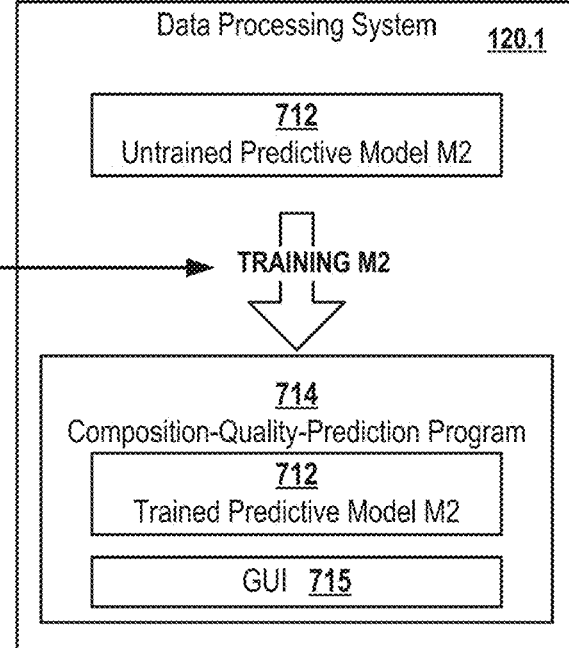
Figure 7:
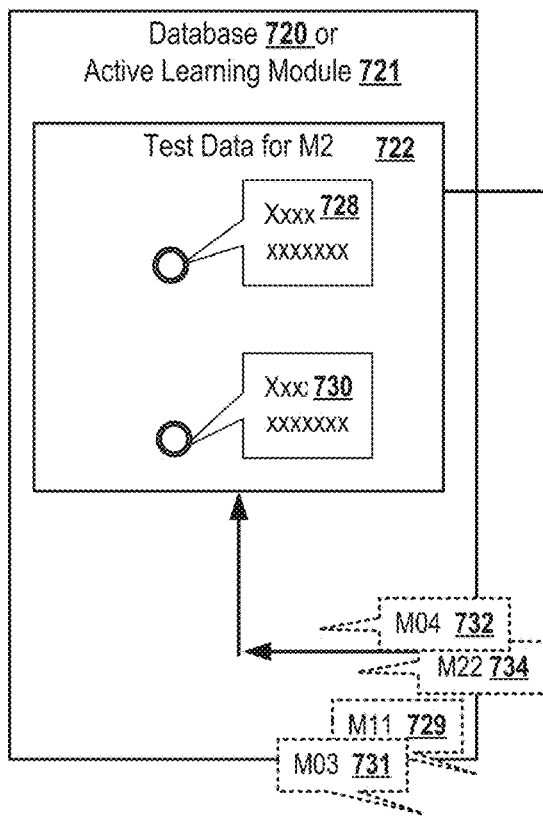
Figure 7:
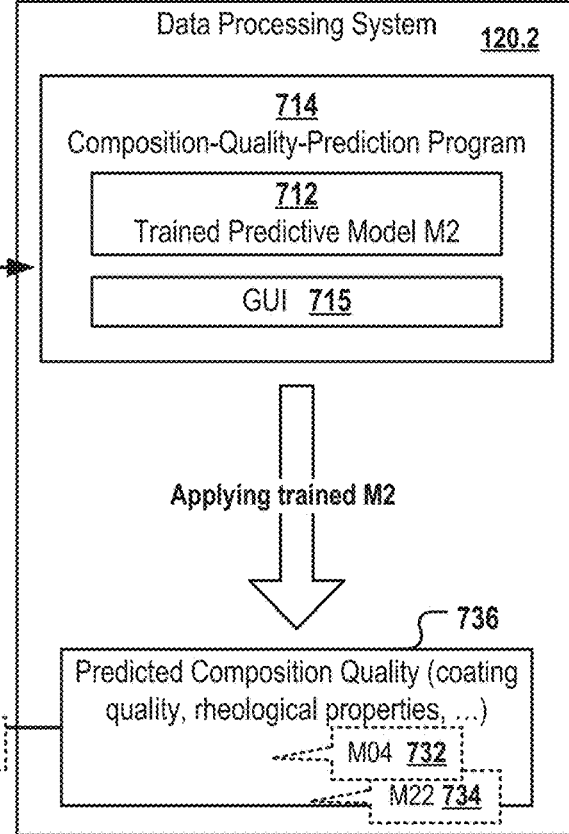

FIG. 7 shows an illustration of the training and test phase for generating and using a composition-quality prediction program 714. Contrary to the defect-identification program, the composition-quality prediction program 714 does not require a digital image as input. Rather, the predictive model M2 712 used by the composition-quality prediction program uses a plurality of parameters as input. These input parameters are selected from a group comprising components, component amounts, manufacturing process parameters and/or application process parameters. The quality related characterizations of a coating surface and optionally further coating composition quality indicators are computed and output by the coating composition quality prediction program.

The combined use of a defect-identification program and a composition-quality prediction program may be beneficial, because for the first time, the defect-identification program provides quality characterizations of a coating surface in sufficient amount, quality and objectivity as to allow the use of this data for training a different machine learning programs 712 to solve a different task, e.g. quality prediction of a coating composition, whereby the quality of a coating surface is also taken into account.

During the training phase of the model M2, training data 702 is provided. The training data 702 comprises a plurality of data records (here: two data records represented as circles), whereby each data record represents a coating composition. Each data record can comprise a complete or incomplete specification 628, 630 of the nature and/or amount of the components of the composition, a specification of manufacturing process parameters and/or of coating composition application process parameters. In addition, each data record comprises characterizations 632, 634 of a coating surface generated by a) coating a sample with the respective coating composition, b) acquiring an image of the coated surface, and c) analyzing the image by the defect-identification program for computing the coating surface characterization 632, 634. In addition, each data record can comprise one or more further properties 732, 734, in particular rheological properties, shelf life, density, etc.

During the training phase, the machine learning model 712 learns to correlate the coating surface characterizations 632, 634, the data comprised in the specifications 628, 630, and the additional properties 732, 734, if any.

As a result of the training, the trained predictive model M2 is able to predict the quality of the coating composition 732, 734 as a function of its components and associated process parameters 728, 730, if any. For example, the quality of the coating composition can be predicted and provided in the form of quality characterizations 732, 734 of a coating surfaces as output by the defect-identification program. In other embodiments, the quality of the coating composition can be predicted and provided in the form of a combination of the quality characterization of the coating surface and other property values 729, 731, e.g. an indication of the shelf life, viscosity and the like.

The training of the predictive model M3 to be used by a coating-specification-prediction program can be performed analogously as described for model M2, whereby the same correlations are learned but the input data of M2 is learned as the output data of M3 and the output data of M2 is learned to be used as input data of M3. Optionally M3 uses additional data like an incomplete coating specification provided to limit the solution space that has to be evaluated by model M3.

FIG. 8A shows a plurality of coating compositions having been manufactured automatically in an HTE based on a respective coating composition specification.

FIG. 8B shows a "draw down" coating application unit. In a first step, a certain amount of the coating composition is applied to the surface of the sample. A roller is then moved over the surface at a defined distance from the surface, whereby the amount is spread evenly over the surface and form the coating.

FIG. 8C shows a "spraying"-coating application unit.

FIG. 8D shows an automated conveyor belt of a high-throughput facility for manufacturing and/or testing coating compositions. The conveyor belt is adapted to automatically transport the coated samples to an image acquisition unit of the facility. The samples are loaded into the image acquisition unit and the camera, light source and/or the sample are moved and positioned relative to each other such that the images acquired from the surface of the sample are suited for automated processing by the defect-identification program.

Figure 9A:
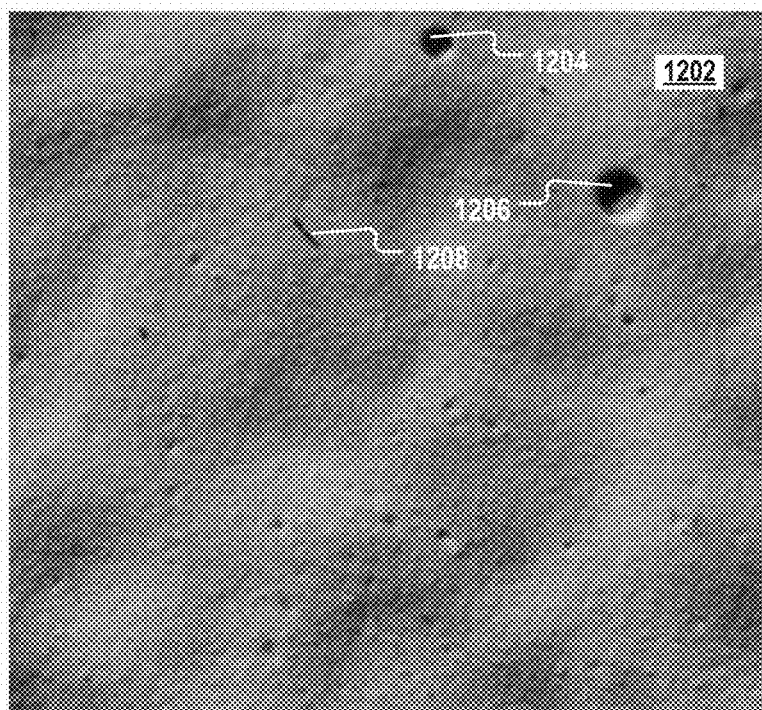
FIG. 9A a digital image of a coating surface before manual annotation of the defects.

FIG. 9A shows a sub-area of a digital image 1202 of a coating surface before manual annotation (label assignment) of the defects. For example, the image may have been acquired by a camera in an image acquisition unit of a facility for automatically manufacturing and/or testing coating compositions. Alternatively, the image may have been obtained by a camera of a data processing system described for example with reference to FIGS. 4 to 5.

The image acquisition conditions (lighting, camera settings, image acquisition angle, illumination angle, etc.) are selected so that the defect to be examined is shown as well as possible on the images. According to embodiments, different image acquisition conditions are set and used for different types of defects. For example, defects associated with elevations or depressions of the surface may be analyzed based on images obtained using a shallow illumination angle (i.e., a shallow light incidence angle) in order to ensure that the defects cause shadows of sufficient size and contrast. Other defects, e.g. color defects, may be analyzed based on digital images obtained using a steep illumination angle (of about 80-100°).

The digital image 1202 shows a coating surface containing foam defects. The coating surface comprises two major defects (holes) 1204, 1206, and several smaller defects (small holes). As the substrate was illuminated from the side, the defects are clearly recognizable due to the shadow formation. The shadow formation allows the identification and differentiation of elevations and depressions of the coating on the substrate. In addition, the shadow formation can be used to judge whether, for example, in the case of a depression, there is a sharp edge, or the coating thickness is slowly decreasing. This may allow discerning bubble defects from cratering defects.

In addition to the defects, the digital image comprises an artifact 1208 which is not a coating defect. For example, the artifact can be caused by a dust speckle on one of the lenses of the image acquisition system or on the substrate.

In order to generate a training data set of sufficient size, digital images of many different coating surfaces comprising many different types of coating defects are acquired. For the foam defects, a shallow light incidence angle is chosen. For other types of defects, other image acquisition settings and conditions may be chosen. Preferably, the surface of each coated sample is illuminated under many different conditions and a respective digital image is acquired in order to be able to generate a defect-identification program that is able to identify many different types of defects which may overlay each other.

Preferably, a large number of digital images showing several thousand defects of different defect types and different types of coated substrates is acquired which are manually annotated (labelled).

Figure 9B:
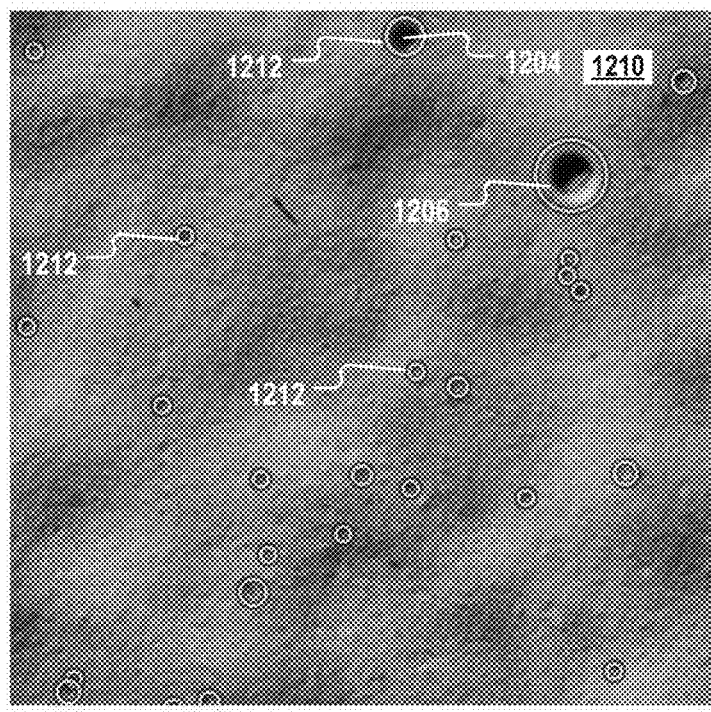
FIG. 9B the digital image of FIG. 9A comprising manually labeled (annotated) defects.

FIG. 9B shows the digital image 1202 of FIG. 9A comprising manually labeled (annotated) defects. Annotating a digital image may comprise storing the digital image in association with information being indicative of the position and type of the coating defects depicted in the image. Optionally, the labels may comprise additional data such as image resolution which may allow determining quantitative defect measures such as diameter, circumference, or the like.

Annotating many images manually consumes a considerable amount of time and effort. In order to ease matters, images where cut into smaller sections. For some of these sections, the foam defects were marked with the software VIA-VGG Image Annotator (Abhishek Dutta and Andrew Zisserman, 2019, "The VIA annotation software for images, audio and video", Proceedings of the 27th ACM International Conference on Multimedia (MM '19), Oct. 21-25, 2019, Nice, France. ACM, New York, NY, USA, 4 pages. https://doi.org/10.1145/3343031.3350535.).

The defects 1206 and 1208 have been manually marked by manually drawn circles 1212 around each defect using the VIA software. The VIA software was then used to export the marking information in a structured format in association with the image or an image identifier. The structured format can be, for example, an XML file, a JSON file, a comma separated file, data records in a relational database or the like.

According to some embodiments, additional data is stored in association with the image or the image identifier. The additional data can comprise a complete or incomplete specification of the coating composition used for creating the coating surface, whereby the specification may comprise an indication of the identity and/or amounts of the components, manufacturing process parameters being indicative of aspects of the process of manufacturing the composition, application process parameters specifying aspects of the process of applying the composition on the substrate and/or image acquisition system parameters. This may allow the predictive model M1 (or additional predictive modes M1.2 used by the coating quality prediction program) to learn correlations between defect types and coating surface characterizations on the one hand and one or more of the above-mentioned parameters.

The generation of the predictive model M1 to be used by the defect-identification program can be performed, for example, as described with reference to FIG. 6.

The trained model M1 can then be used to detect foam defects (and other types of defects covered by the training data) in new, unlabeled images which have not been used in the training step (and which are referred to as "test images").

Figure 10:
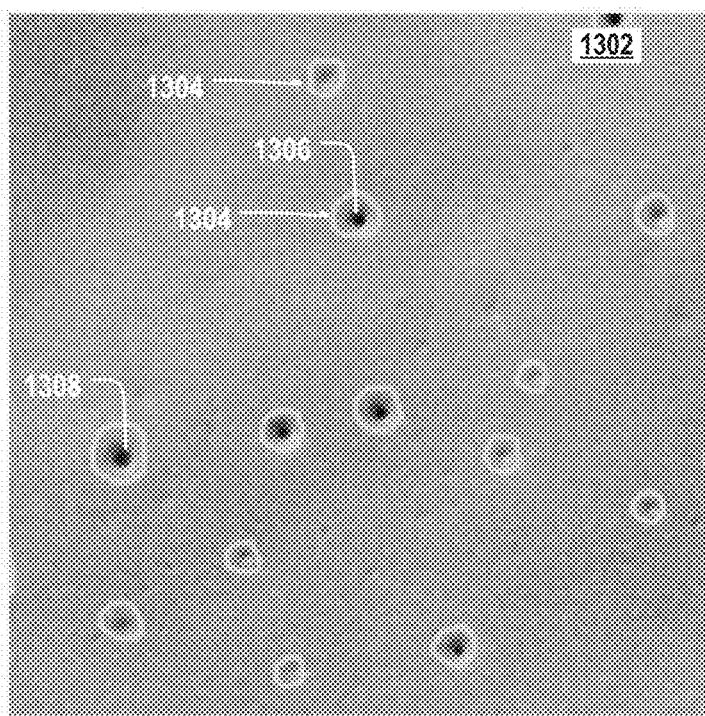
FIG. 10 a digital image of a coating surface with automatically identified and labeled defects.

FIG. 10 shows a digital image 1302 of a coating surface. The image comprises labels 1304 which have been automatically created by a defect-identification program 124 according to an embodiment of the invention. The labels identify defects 1306, 1308 having been automatically detected by the defect-identification program.

In addition to the visual representation of the detected defects (e.g. via image segments overlaying identified defects or, as in this case, via edges and circles surrounding the identified defects), the defect-identification program is configured to temporarily or permanently store the types and locations of the identified defect also in a structured form. For example, the location can be stored in the form of pixel coordinates of pixels representing a defect. Storing the identity and location of the defects in structured form allows the defect-identification program to process the structured data to compute aggregated characterizations of the coated surface.

For example, the aggregated characterization of the whole surface may be a quantitative characterization of the coating surface, e.g. a scale value referring to a quality scale with more than 5, e.g. more than 10 possible scale values, whereby the scale may represent the integrated coating surface quality. The quality score of a surface negatively correlates with the size and number of defects identified in the coating surface.

Figure 11:
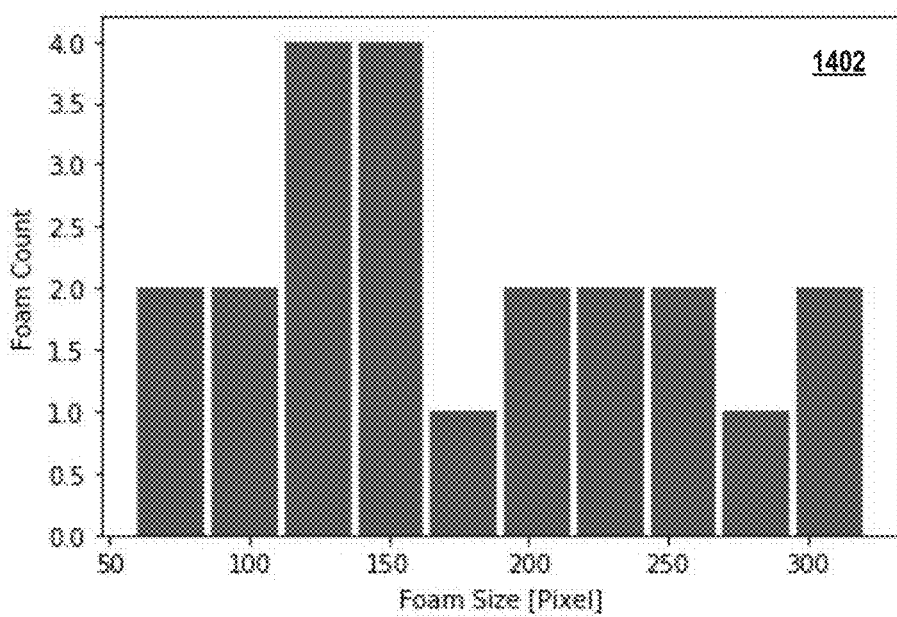
FIG. 11 measures of a defect of a surface area in the form of a histogram and an area percentage value.

Another example for a quantitative defect measure and/or for a quantitative characterization of a coating surface would be a histogram of defects of different sizes as depicted in FIG. 11.

FIG. 11 shows measures of a defect of a surface area in the form of a histogram 1402 and an area percentage value. The histogram and/or the percentage value may be used as a quantitative characterization of the coating surface or may be used to computationally derive such a characterization.

The histogram 1402 depicts the distribution of foam bubbles of different sizes, wherein a bubble size is specified as the area of a bubble measured in pixels. The bubble sizes are grouped into 10 different bins and the number of bubbles having a size falling in the size range of a bin are plotted. Hence, the histogram provides a rough estimate of the size distribution of the bubbles which may allow identifying problems in the coating composition or the coating process.

In addition, the fraction of the surface covered by bubble defects is counted (5.88% in this case). This value can be used as quality characterization of the coating surface depicted in the processed digital image. By evaluating the number and size of the defects, it is possible to classify a coating surface into predefined quality classes or grades in an objective, reproducible manner.

Figure 12:
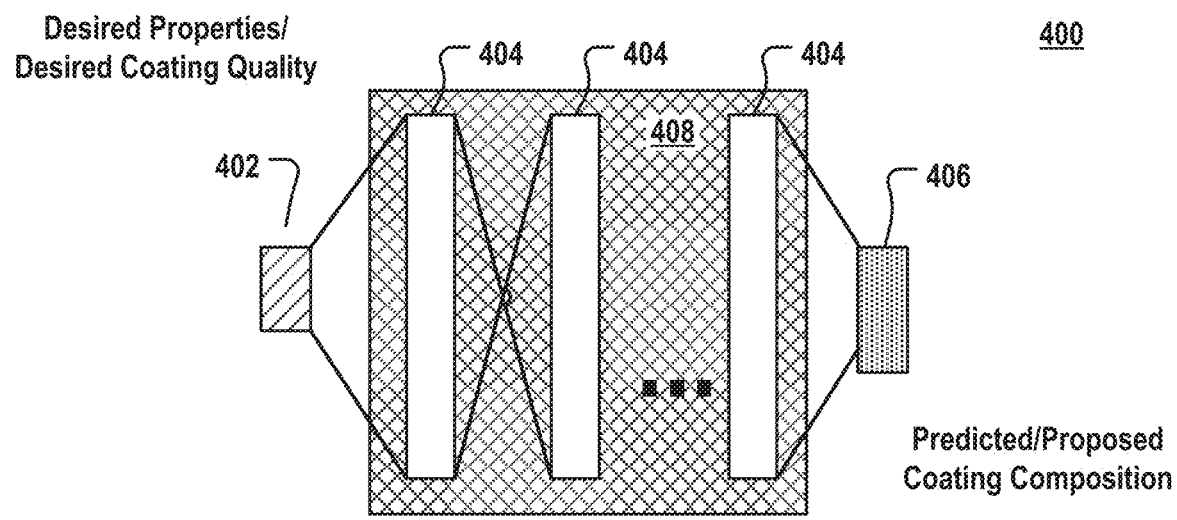
FIG. 12 an architecture of a neural network used for predicting the quality of a coating composition.

FIG. 12 shows an architecture of a neural network 400 encoding a predictive model M2 and being used for predicting the quality of a coating composition.

The network 400 is configured and trained to receive an input vector 402 and to calculate and output an output vector 406 as a function of the input vector.

For example, the input vector can encode a complete or incomplete specification of the components (and optionally also the concentrations or quantities of the respective components) of a coating composition. Optionally, the input vector may further comprise process parameter values of a coating composition manufacturing process and/or of a coating application process.

The output vector 406 specifies one or more properties of the composition or of a surface generated by coating a substrate with the composition. The properties preferably include one or more properties representing the quality of the coating composition and/or the quality of a coating surface formed by the coating composition.

The network includes several layers 404 of neurons, which are linked with the neurons of other layers by means of weighted mathematical functions in such a way that the network can calculate, i.e. predict, the properties and quality characterizations of the corresponding compositions and of coating surfaces generated from the said compositions on the basis of the information encoded in the input vector and can output the predicted properties and quality characterizations in the form of an output vector 406.

Before training, the neurons of the neural network are first initialized with predetermined or random weights. During training, the network receives a specification of a coating composition (which may comprise the type and optionally also the amounts of the components and optionally manufacturing process parameters or application process parameters) together with empirically measured properties of this composition, including defect measures and coating surface characterizations computed and output by a defect-identification program 124. The network calculates the output vector with predicted properties and quality measures of this composition and is penalized by the loss function for deviations of the predicted properties and quality measures from the known, empirically determined properties and coating surface characterizations. The determined prediction error is distributed back to the respective neurons that caused it via a process called backpropagation and causes the weights of certain neurons to change in such a way that the prediction error (and thus the value of the loss function) is reduced. Mathematically, this can be done by determining the slope of the loss function, so that the neuron weights can be directionally modified to minimize the value output by the loss function. Once the prediction error or loss function value is below a predefined threshold, the trained neural network is considered sufficiently precise so that further training is not necessary.

After the training is successfully completed, the trained predictive model M2 can be used to predict the properties, in particular quality characterizations of a coating surface of a new, unknown coating composition. In case the exact composition and/or the optimum manufacturing process parameters and/or coating process parameters are not known, a human user or an accessory software program generate several candidate coating composition specifications which represent and specify variants of the new coating composition of interest. The trained neural network is used to automatically predict the properties of each of the new (candidate) coating compositions. In case the prediction was performed for multiple candidate coating compositions, the one or more of the candidate coating compositions having the best properties or quality characterizations for the respective application scenario are selected and/or are actually produced and tested in the facility.

The predicted properties of each candidate coating composition are output as output vector 406 of the neural network to a user for manual evaluation and/or are stored in a database, e.g. for further evaluation and comparison with empirically obtained property values of the composition which may be obtained later. The input vector can contain, for example, 20 components of a coating composition, some manufacturing process parameters and some application process parameters. The output vector 406 may comprise various properties whose nature depends on the training data used for training the predictive model M2 encoded in the network. For example, the output vector can comprise an indication of the type and extent of coating defects which will likely occur if the coating is applied on a substrate.

Figure 13:
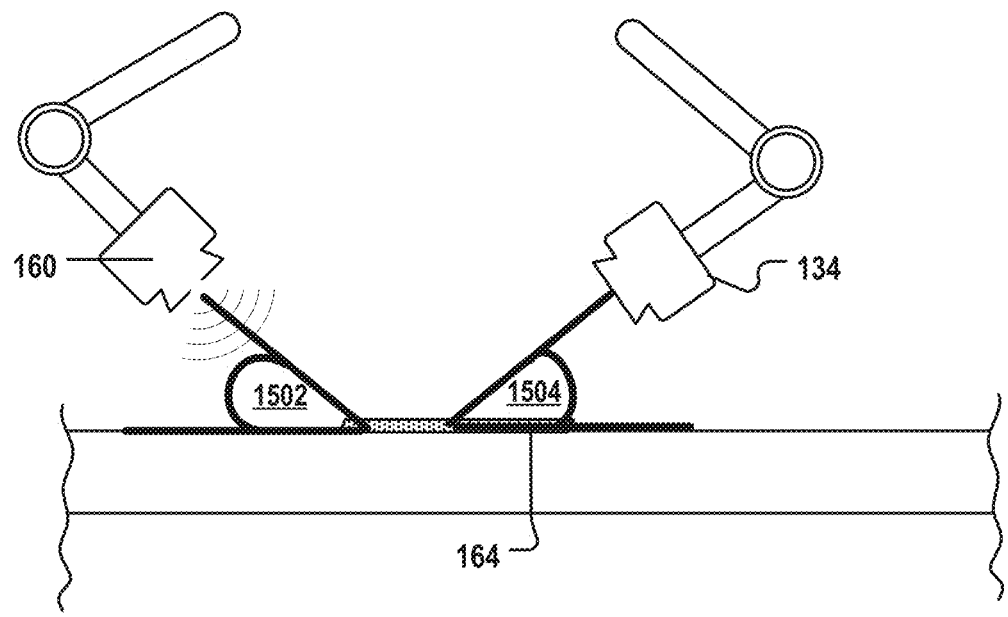
FIG. 13 an illustration of the relative positioning of a camera, a light source and the coated surface for acquiring a digital image.

FIG. 13 shows an illustration of the relative positioning of a camera 134, a light source 160 and the coated surface 164 for acquiring a digital image. For example, the relative positioning can be performed manually, e.g. in case the camera is a smartphone camera. In other embodiments, the relative positioning can be performed automatically, e.g. within an image acquisition unit of a facility 244 for manufacturing and/or testing coating compositions. By performing the relative positioning, it is ensured that the image acquisition angle 1504 and the illumination angle 1502 are chosen such that the digital image of the coting surface will allow an automated identification of the coating defects by the defect-identification program 124. For example, the angles 1502, 1504 should typically be identical or similar to the angles used for obtaining the digital images used for training the predictive model M1 of the defect-identification program. For example, an angle "similar" to angle X can be an angle in the range of X up to plus or minus 40% of X, in particular X up to plus or minus 20% of X. according to embodiments, multiple digital images are obtained for each coated sample, whereby the image acquisition angle 1504 and/or the illumination angle 1502 differ from each other. This may ensure that for many different types of defects, the set of acquired images comprises one or more images which allow accurate identification and characterization of a defect.

Figure 14:
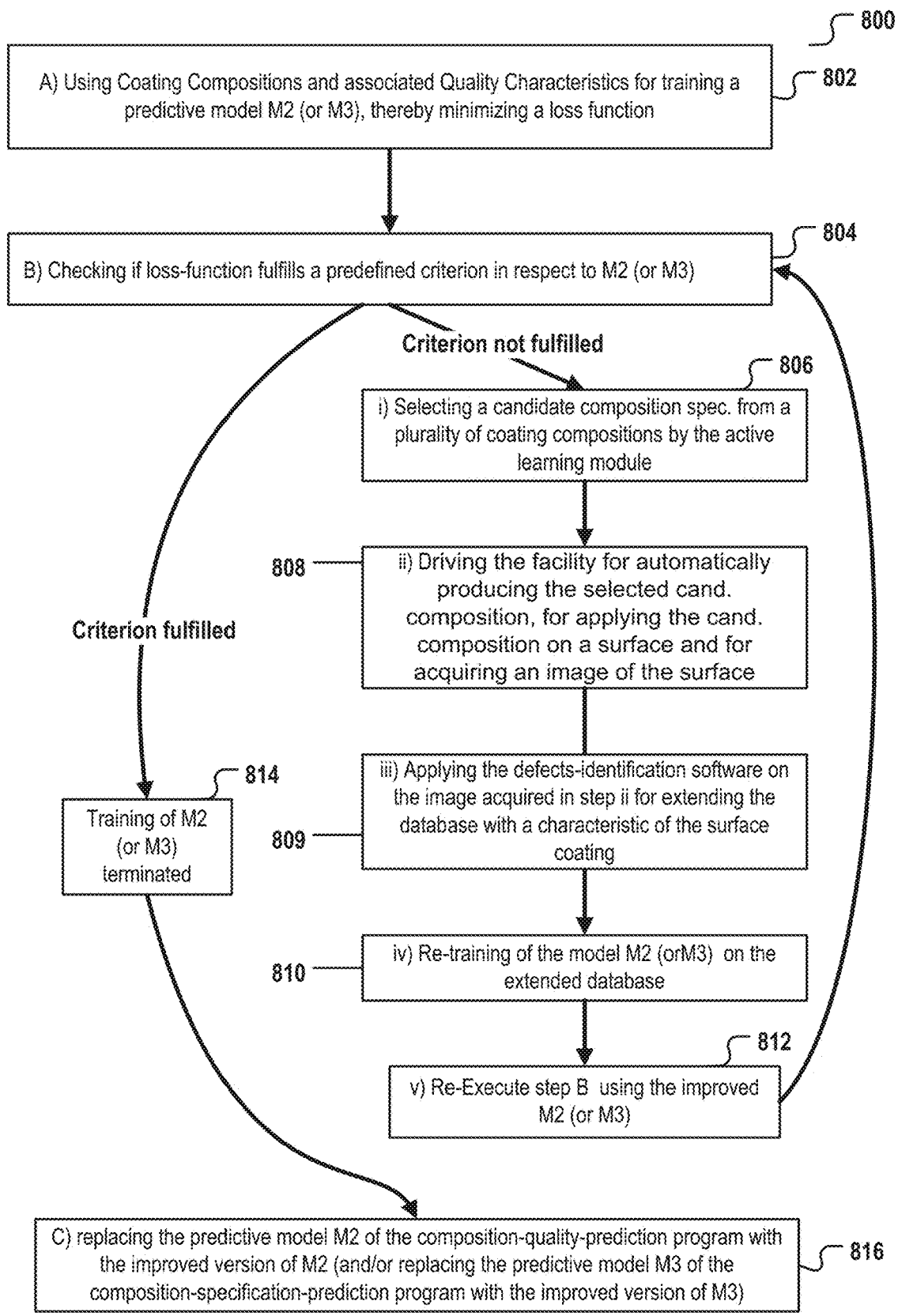
FIG. 14 a flow-chart of a method for identifying candidate coating composition best suited to improve the quality of a predictive model of the composition-quality-prediction program.

FIG. 14 shows a flow-chart of a method for identifying a coating composition best suited to improve the quality of a predictive model M2 (or M3) of the composition-quality-prediction program.

The process can, for example, be carried out by a computer system 120.2 as shown in FIG. 7 or computer system 170 depicted in FIG. 5D.

In a first step 802a), already known compositions and their properties and quality characterizations, including characterizations of the coating surface generated by the composition, are used as an "initial training data set" to train a model M2 (or M3), e.g. a neural network, a support vector machine, a decision tree, a random forest or the like. The trained model M2/M3 can be integrated in a composition-quality prediction program configured to predict properties of a coating composition, e.g. the quality of a coating surface created by the coating composition, or into a composition-specification prediction program In the next step 804(b), a check is performed to determine whether the value of a loss function meets a predefined criterion. A fulfillment of the criterion expresses that the prediction accuracy of the trained neural network is considered sufficient. Selectively for the case that the criterion is not fulfilled, the steps 806-812 described below are performed. Otherwise the training is terminated (step 814) and the trained neural network is returned.

In step 806, the Active Learning module automatically selects a specification of a candidate coating composition from a plurality of manually provided or automatically computed candidate coating composition specifications. There exist several different Active Learning approaches that can be used according to embodiments of the invention.

According to one embodiment, the Active Learning module follows the "expected model change" approach and selects a specification of the candidate coating composition that (when the network is re-trained taking into account this candidate coating composition and its real measured properties) would change the current predictive model the most.

According to another implementation variant, the Active Learning Module follows the "expected error reduction" approach and selects the candidate composition that would most strongly reduce an error of the current predictive model of the trained neural network.

According to another implementation variant, the Active Learning Module follows the "Minimum Marginal Hyperplane" approach and selects the experimental composition that is closest to a dividing line or plane that is spanned in a multidimensional data space by the current predictive model of the trained model. The dividing line or dividing plane are interfaces within the multidimensional data space in which the predictive model makes a classification decision, i.e. assigns data points on one side of the dividing line or dividing plane to a different class or category than the data points on the other side of the dividing line. This proximity of the data points to the parting plane is interpreted in such a way that the predictive model is uncertain about a classification decision and would benefit to a particularly high degree if real measured data sets (consisting of a combination of components and optionally their concentrations and the measured properties of the coating composition produced according to this composition of the components) from the vicinity of this parting plane were additionally measured in order to further train the model.

After retrieving the specification of the selected candidate coating compositions from the database, in step 808 the computer system controls a composition production and testing facility 244 so that a product is automatically produced and tested according to the retrieved specification. This testing is understood to be a metrological recording of one or more properties of the product, e.g. the measurement of pH value, color value, viscosity, the computation 809 of a characterization of a coating surface created by coating a sample with the composition, taking an image and having the image analyzed by a defect-identification program, or the like.

The real measured properties obtained in step 108 and the computed values derived from image data obtained in step 809 are used to supplement the selected candidate coating composition, so that a complete further data point consisting of a known composition and known properties is obtained, which serves to extend the training data set used in a) of the current or previous iterations.

In step 810, the model M2/M3 is retrained on the extended training data set. Depending on the implementation variant, this can be done in such a way that the training is carried out again completely on the basis of the extended training data set, or the training in step 810 is incremental, so that what has been learned so far is retained and only modified by taking the new training data point into account.

In step 812, a repeated check of the prediction quality of the trained model M2/M3 is initiated and steps 804-812 are repeated until the model has sufficient prediction quality, which is indicated by the fact that the loss function fulfils the criterion, e.g. the "error value" calculated by the loss function is below a predefined maximum value.

The fully trained model can now be used to predict the properties of a coating composition, including quality characterizations of a coating surface obtained from this coating composition, very quickly and reliably. To do this, the re-trained model M2 is integrated in a quality prediction program, whereby an older, less accurate version of the model may be replaced.

Since the model has learned the statistical correlations between various parameters related to coating compositions (in particular their components, absolute or relative amounts, manufacturing process parameters and/or application process parameters) and the properties of the resulting product (including characterizations of a coating surface created from the composition), the trained model M2 can now predict the properties and also the quality of a corresponding coating surface given a specification of a coating composition even for compositions for which no empirical data is available. Likewise, a trained model M3 can predict one or more of the above-mentioned parameters related to a coating composition given a desired coating surface characterization and optionally an incomplete coating composition. Both the model M2 and the model M3 rely on learned associations of empirically measurable or derivable coating composition properties such as a coating surface characterization on the one hand and the above-mentioned various parameters related to the coating composition. The models M2 and M3 differ only in respect which of the said two aspects is expected as input and which is provided as output.

A "loss function" (also called "objective function") for a prediction problem, can, for example, in the simplest case, only count the correctly recognized predictions from a set of predictions. The higher the proportion of correct predictions, the higher is the quality of the predictive model (e.g. a model implemented in a neural network) used in a machine learning process. For example, the question whether a rheological property such as viscosity and/or a quality property such as the type and extent of coating defects in a coating surface is within a predefined acceptable range can be understood as a classification problem.

However, many alternative loss functions and corresponding criteria for assessing the prediction accuracy of the trained model are also possible.

Figure 15:
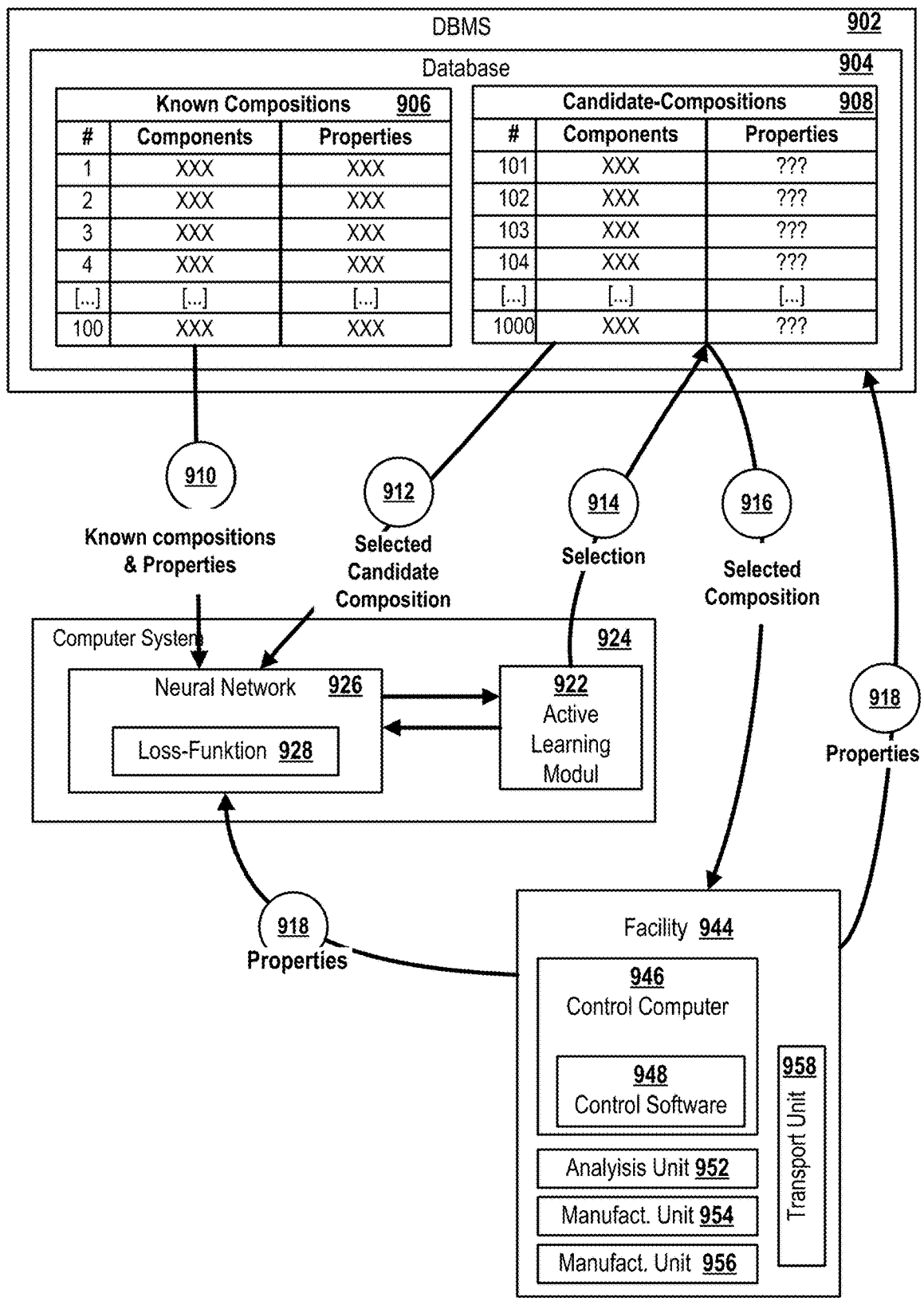
FIG. 15 a block diagram of a distributed data processing and coating manufacturing system used for improving the predictive model of the composition-quality-prediction program.

FIG. 15 shows a block diagram of a distributed data processing and coating manufacturing system 900 used for improving the predictive model of the composition-quality-prediction program;

The system includes a database 904 with known coating compositions 906 and candidate compositions 908. The known compositions 906 may, for example, be a set of data records each containing a complete or incomplete specification of the type and/or the amount of components, of manufacturing process parameters and/or coating composition application process parameters. In addition, each data record of the known coating compositions comprises empirically determined physical, chemical, haptic, optical and/or other metrologically ascertainable properties of the coating composition and/or a coating surface generated therefrom, whereby "empirically determined" includes measures and characterizations computed as a function of empirical data, e.g. quality characterization computed as a function of image data.

The candidate compositions 908, on the other hand, are compositions whose physical, chemical, haptic, optical and/or other metrologically ascertainable properties are not known.

For example, the known compositions 206 can comprise coating composition specifications having already been produced and tested by an HTE facility.

The coating compositions specifications 908 can comprise coating composition specifications provided by a buyer of a coating component or can be provided in a computational step of automatically creating variant coating composition specifications based on a single provided complete or incomplete coating specification.

For example, the specifications of the coating composition variants can be created by increasing and/or decreasing the amount of one or more components of this composition by 10%. If only one single component is varied at a time, using a quantity of this component increased by 10% and a quantity reduced by 10%, two variants are formed per component. With 20 components, 40 candidate compositions are created with this procedure. The number of automatically generated candidate compositions is preferably further increased by simultaneously increasing or decreasing the concentration of two or more components compared to their concentration in the known composition and 10% and by modifying process parameters.

Typically, the number of automatically computed candidate compositions is considerably larger than the number of coating compositions that a laboratory can actually physically prepare and test in terms of cost and profitability.

The distributed system 900 includes a computer system 924, which comprises a neural network or another type of machine-learning model and an active learning module 922. The Active Learning Module 922 has at least a read access to read one or more selected candidate compositions and a specification of respectively assigned parameters, e.g. their components, from the database 904. According to some embodiments, the Active Learning Module and/or a facility 944 which prepares and analyzes a coating composition and optionally also a coating surface created therefrom according to the selected candidate composition specification, also has write access to the database 904 in order to store the empirically obtained properties of the selected candidate coating composition or of the respective coating surface in the database 904. For example, obtaining and storing coating surface characterizations and/or measures of coating defects of a selected and newly prepared candidate composition may result in this candidate composition becoming a known composition and accordingly being stored in a different location and/or provided with different metadata ("flag") in the 904 database.

Figure 16:
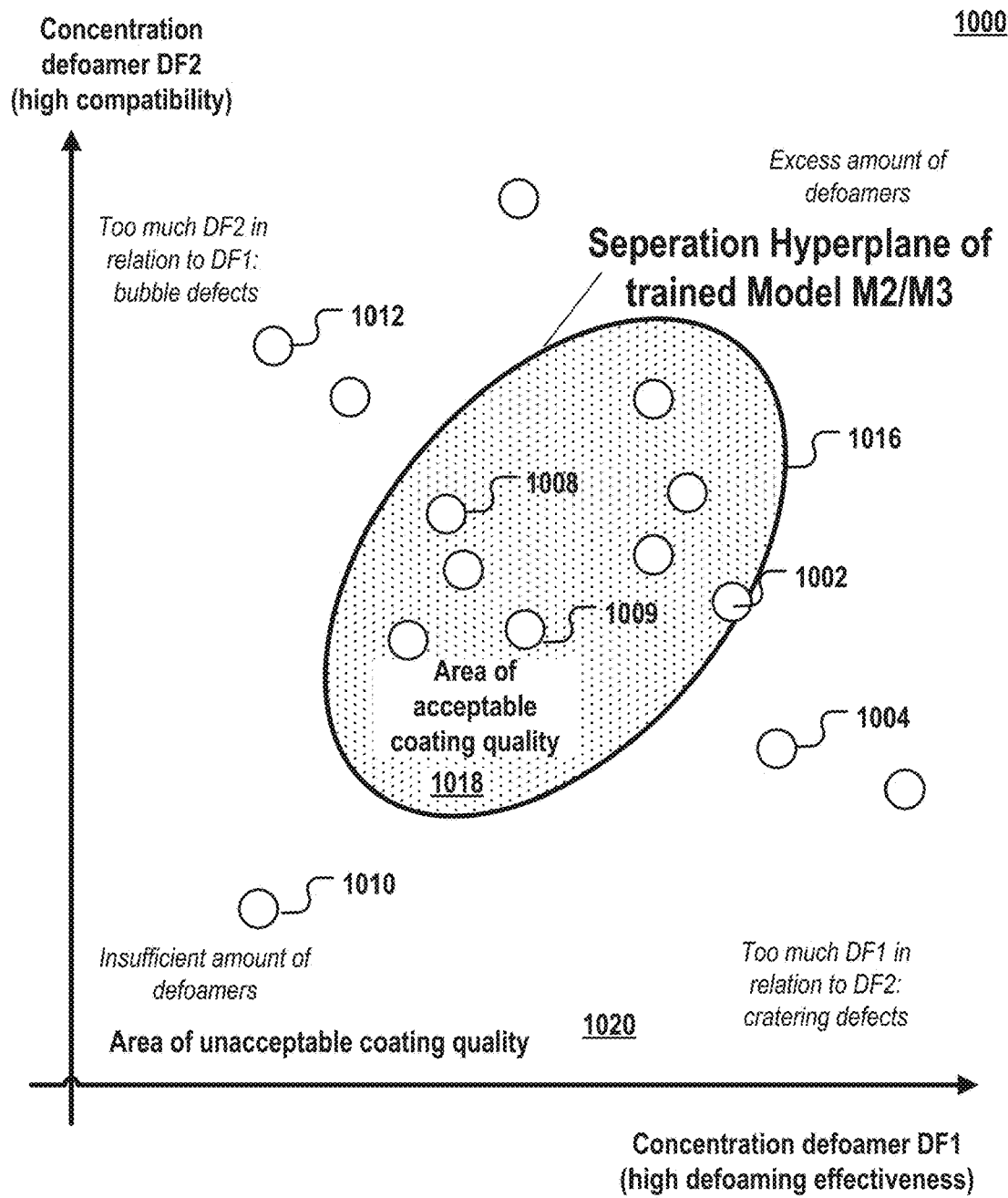
FIG. 16 a 2D section of a multidimensional data room for various combinations of a defoamer DF1 with optimum anti-foam property and defoamer DF2 with optimum compatibility in specific coating composition, from which the "Active Learning Module" selects specific data points.

FIG. 16 shows a 2D section 1000 of a multidimensional data room for various combinations of a defoamer DF1 with optimum anti-foam property and a defoamer DF2 with optimum compatibility in a specific coating composition, from which the "Active Learning Module" selects specific data points 1008 in order to extend the training data set and to improve the accuracy of the predictive model M3 used by the composition-specification prediction program. The model improvement is described in the following for model M3, but can likewise be used for improving the model M2 used by the coating composition quality prediction program.

In the course of the training of the predictive model M3, which can be implemented as a neural network or other type of machine learning model, the predictive model learns to calculate an output vector, which may include one or more of the following: type of the components, absolute and/or relative amounts of the components, coating composition manufacturing parameters, and/or coating composition application process parameters. The input data is preferably provided as input vector and comprises one or more desired surface characterizations, e.g. quality characterizations provided as input. Optionally, the input may comprise an incomplete specification of one or more components, absolute or relative component amounts, manufacturing process parameters and/or application process parameters or respective amount or parameter validity ranges. The incomplete specification can be used by the model to limit the solution space to predicted coating compositions. For example, if the incomplete specification indicates a water-based coating medium, the predicted composition proposed by the model will not be based on an organic coating medium. If the incomplete specification indicates that two defoamers DF1 and DF2 should be used, only the relative amounts of these defoamers may be predicted by the model. If only one defoamer DF1 is provided as input, the model M3 may only suggest a further defoamer DF2 which is predicted to be compatible with defoamer DF1.

The input vector of the model M3 may include in particular one or more of the following properties: coating surface quality measures, coating defect types (in particular bubble defects and cratering defects), coating defect measures, storage stability, pH value, rheological parameters, in particular viscosity, density, relative mass, coloristics, in particular color strength, and/or cost reduction during production. The cost reduction during production can, for example, be automatically recorded by an automated production facility 244 during the preparation of a composition and can, for example, relate to a given reference value. However, it is also possible for a human to manually record the costs. Likewise, the coating defects and surface quality measures can be automatically determined by the facility 244.

In the depicted example, the input received by the model may indicate that both the occurrence of bubble defects and the occurrence of cratering effects should be minimized. The input may further specify one or more components of the coating composition, and in particular may specify that a defoamer DF1 with optimum anti-foam property and a defoamer DF2 with optimum coating medium compatibility in the (incompletely) specified coating composition should be used as components, but no absolute or relative amounts of the defoamers is provided. For example, the DF1 can be Evonik's Tego Foamex 810 and DF2 can be Evonik's Tego Wet 285.

Based on the available data, the M3 model has learned that a mixture of the DF1 and DF2 defoamers produces a foam volume that lies between the two foam volumes produced by the two defoamers individually. The foam volume-defoamer-ratio relationship almost represents a straight line, whereby the foam volume and the associated bubble defects decrease with an increasing ratio DF1:DF2, and thus the surface quality with respect to the bubble defects increases. Furthermore, the model has learned that the compatibility of the mixture of the two defoamers with the coating medium decreases with an increasing ratio DF1:DF2, i.e. the surface quality with regard to the cratering defects decreases.

After some initial training steps, the model M3 of the neural network has already "learned" certain relationships between components or process parameters of the coating compositions and some properties of the resulting coating composition or coating surface. Based on the knowledge stored in the model M3, the model can predict that if the DF1:DF2 ratio in the incompletely specified composition provided as input is too high, many cratering effects will occur, and that if the DF1:DF2 ratio is too low, many bubble defects will occur.

These learned relationships are illustrated in FIG. 16 by the dividing outline 1016, which divides the data room with respect to the property "coating quality" into a data room 118 with acceptable coating surface quality properties on the one hand and a data room 1020 with unacceptable coating surface quality properties on the other hand. The plot illustrates that both the absolute and the relative amounts of the defoamers may be of relevance: if the total amounts of both defoamers is too low, bubble defects may occur. If the ratio DF1:DF2 is too high, cratering defects will occur. If the ratio is too low, bubble defects will occur. If the total amount of both defoamers is too high, other surface defects may occur or the production costs (not shown) may be predicted to be unacceptably high.

FIG. 16 can only represent a partial aspect of the data room as a plot can only represent two dimensions ("Concentration DF1" and "Concentration DF2") but other coating components and their absolute and/or relative amounts also have an impact on the coating surface quality. A coating composition has often more than 10, typically about 20 components, and as manufacturing process parameters and coating application process parameters may also represent a respective dimension, the data space 1000 comprises much more dimensions than shown in FIG. 16. Each of the many sub-spaces formed by these 20 dimensions contains its own separating lines and areas of acceptable or unacceptable coating surface quality. The totality of separating lines 1016 in the multi-dimensional space learned by the model M3 during the training is also referred to as separating plane ("hyperplane").

The data points shown as circles in FIG. 16 each represent a candidate coating composition for which the respective properties have not yet been determined empirically. The model M3 may be quite sure that the coating compositions represented by e.g. data points 1008, 1009 lie within an area of acceptable coating quality and that the coating compositions represented by data points 1004, 1012, 1010 have unacceptable coating quality. However, the model may not be sure about the surface quality of a coating composition represented by the data point 1002. So it can be assumed that preparing a coating composition represented by data point 1002, empirically determining various properties of the coating composition (including coating surface defects), and using the obtained empirical data for extending the training data set and retraining the model M3 on the extended training data set may provide the highest learning effect for the model.

For example, the data point 1002 to be used for extending the training data with further empirical can be selected e.g. according to the so-called "Minimum Marginal Hyperplane" approach. For example, the Active Learning Module can be designed as a support vector machine or as another algorithm capable of dividing a data space spanned by the totality of data points into subspaces with respect to one or more properties based on the knowledge the predictive model has already learned from a sub-set of the data points. Hence, the current "knowledge" already acquired during an initial training of the model M3 is represented by the dividing line or dividing plane 1016. The "Minimum Marginal Hyperplane" method assumes that the data points 1002 with the smallest distance to the dividing line 1016 are those for which the already learned predictive model, represented by this dividing line 1016, is most uncertain and therefore the experimental composition belonging to this data point should be selected, prepared and analyzed in order to empirically determine the actual properties, e.g. the coating surface characterization and/or the viscosity. In the example presented here, the active learning module would thus select the candidate coating composition represented by data point 1002, taking into account only the property "coating surface quality", and cause the plant 244 to prepare and analyze this composition in order to extend the training data with the specification of the components of composition 1002 and empirically measured properties of the coating composition and a corresponding coating surface. The model M3 would then be re-trained on the extended training data set.

As an example, the empirical measurement of the composition represented by data point 1002 may show that its predicted coating surface quality is in the unacceptable coating quality area 1020. The consequence of re-training on the extended training data set would therefore be that the predictive model of the neural network, here graphically visualized by the dividing line 1016, would adapt in such a way that for a composition represented by data point 1002, the prediction in the future would be that its coating surface quality lies in the area 1020. Thus, by re-training on the extended training data set, the line/plane 1016 would be modified in such a way that the line or plane receives a "bulge" such so that the improved model would now recognize and predict that the composition represented by point 1002 is in the unacceptable coating quality range 1020. In practice, when selecting the data point or the corresponding experimental composition, the distance of the corresponding data points to the separation lines of several properties is preferably taken into account, e.g. by selecting the data point with the minimum average distance to all separation lines/ separation planes of the complete multidimensional data space.

The improvement of a model M2 to be used for predicting a coating composition quality based on a complete or incomplete specification of the coating composition and/or associated process parameters can be performed analogously with the only difference that the information respectively used as input or output of the model is interchanged.

In a further aspect, disclosed herein is a computer-implemented method and corresponding system for qualitative and/or quantitative characterization of a coating surface. The method and system comprise steps and features as described in the clauses below.

1. Clauses: A method for qualitative and/or quantitative characterization of a coating surface, the method comprising:
    processing (102) a digital image (604, 606, 1202) of the coating surface (162-168) by a defect-identification program (124), the defect-identification program being configured to recognize patterns, each pattern representing a type of coating surface defect (1204, 1206, 1306, 1308); and
    outputting (104) a characterization of the coating surface by the defect-identification program, the characterization being computed as a function of coating surface defects recognized by the defect-identification program during the processing.
2. The method of clause 1, comprising:
    calculating (106), by the defect-identification program, a measure (632, 634, 1402) for the recognized defects;

wherein the characterization of the coating surface is computed as a function of the qualitative and/or quantitative characterization of the measure.
3. The method of clause 2,
   the measure being a quantitative measure selected from a group comprising: the area of the defect, the number of bubbles or depressions observed in the digital image (604, 606, 1202), the maximum, minimum and/or average size of the bubbles or depressions in the digital image (604, 606, 1202); and/or
   the measure being a qualitative measure, the qualitative measure being in particular the type of the defect selected from a group comprising a cratering defect, an abrasion defect, an adhesion failure defect, an alligatoring defect, a bleeding defect, a blistering defect, a bloom defect, a bridging defect, a bubbling defect, a cathodic disbanding defect, a checking defect, a cissing defect, a cobwebbing defect, a cracking defect, a crazing defect, a crowsfooting defect, a delamination defect, a fading defect, a flaking defect, a grinning defect, a heat defect, an impact defect, an intercoat contamination defect, a mud cracking defect, an orange peeling defect, a peeling defect, a pinholes defect, a rippled coating defect, a runs defect, a rust rashing defect, a rust spotting defect, a rust staining defect, a sags defect, a settlement defect, a skinning defect, a solvent lifting defect, a solvent popping defect, a stress cracking defect, an undercutting defect, a wrinkling defect.
4. The method of any one of the previous clauses, further comprising:
   determining at least one coating surface defect type to be identified;
   automatically determining one or more illumination angles and/or one or more image acquisition angles allowing the acquisition of a digital image that enables the defect identification program to compute the characterization of the coating surface depicted in the image in respect to the at least one determined defect type;
   positioning one or more light sources (160) at the determined one or more illumination angles (1502) relative to the coating surface; and/or
   positioning one or more cameras, preferably one camera (134), at the determined one or more image acquisition angles (1504) relative to the coating surface; and
   after the positioning of the light source(s), the camera(s) and/or the coating surface relative to each other, using the camera(s) for acquiring the digital image of the coating surface.
5. The method of any one of the previous clauses, the processing of the digital image further comprising:
   performing, by the defect-identification program, a classification of the digital image in respect to the type and/or amount of surface defects depicted therein and/or a semantic segmentation of the image based on one or more surface defect types depicted therein and/or an object detection of defect instances in the image and/or an instance segmentation of the image, thereby automatically assigning one or more labels to the whole digital image, to image regions and/or to individual pixels, each label being indicative of the type of defect identified in the digital image; and
   outputting the one or more assigned labels.
6. The method of any one of the previous clauses,
   the defects-identification program being operatively coupled to a camera and being configured for
      determining whether the camera is positioned within a predefined distance range and/or within a predefined image acquisition angle range relative to the coating surface adapted to enable acquisition of images from a similar relative position as used for acquiring training images for generating the predictive model of the defects-identification program;
   in dependence on the result of the determination,
      generating a feedback signal for the user and/or the camera whether adjustment of the camera position is required; and/or
      automatically adjusting the relative position of the camera and the coating surface; and/or
      enabling the camera to acquire images selectively in case the camera is within the predefined distance and/or image acquisition angle range.
7. The method of any one of the previous clauses, the defects-identification program being selected from a group comprising:
   an app installed on a portable data processing system (130), in particular a portable telecommunication device, e.g. a smartphone;
   an application program installed on a portable or stationary device (150) specially designed for quality control of coating surfaces;
   an application program installed on a high-throughput facility (244) for the automated or semi-automated manufacturing and/or testing of coatings;
   a web application downloaded and instantiated via a network;
   a program executed within a browser, e.g. a JavaScript program;
   a server program instantiated on a server computer, the server program being operatively coupled via a network connection to a client program instantiated on a client data processing system, the client program in particular being configured for acquiring the digital images and providing the images via the network to the server program and/or for displaying the results provided by the server program.
8. The method of any one of the previous clauses, the defect-identification program comprising a predictive model (M1) having learned from training data (602) in a training step performed by a machine learning program to recognize the predefined patterns, the machine learning program being in particular a neural network.
9. The method of clause 8, the machine learning program being a neural network or a set of neural networks comprising a region proposal network, the region proposal network being configured to scan over anchors of an input image for making a proposal whether the anchor likely contains one of the defect patterns, the anchors being sub-regions of the input image having anchor sizes matching expected sizes of the defect patterns.
10. The method of any one of clauses 8-9, comprising:
   performing the training step on the training data (602), the training data comprising a set of labeled digital training images (604, 606) of coating surfaces, the labels (616, 618) identifying the location/positions and/or type of defects in the training images, the predictive model being trained for recognizing the pattern by means of the labeled training images using back propagation.

11. The method of clause 10, wherein each of the training images has assigned additional data (608, 610) being processed in the training step for enabling the predictive model (M1) to correlate the additional data with the defect patterns, the additional data comprising:
a quantitative measure of one or more defects depicted in the training image, e.g., the size and/or severity of the defect or the number of bubbles;
optionally also parameters selected from a group comprising:
an indication of one or more components of the coating used for generating the coating surface depicting in the training image;
an indication of an absolute or relative amount of one or more of the components of the coating composition; and/or
one or more manufacturing-process parameters, the manufacturing-process parameters characterizing a process of generating a coating composition, the process parameters for example comprising mixing speed and/or mixing duration of the coating composition; and/or
one or more application-process parameters, the application-process parameters characterizing a process of applying a coating composition on a substrate, the application-process parameters in particular comprising the amount of coating composition applied per area of the coating surface, the type of substrate and/or or the type of application devices; and/or
system parameters of an imaging system used for acquiring the training images, the system parameters being selected from a group comprising type of light source(s) used for illuminating the coating surface, brightness of the light source(s), illumination angle, wavelength of the light source(s), type of one or more cameras used for acquiring the digital image of the coating surface, image acquisition angle(s), position(s) of the one or more camera(s).

In a further aspect, disclosed herein is a computer-implemented method and corresponding system for providing a coating composition-related prediction program. The method and system comprise steps and features as described in the clauses below.

Clauses:

12. A computer-implemented method for providing a coating composition-related prediction program, the method comprising:
providing a database (204, 904) comprising associations of qualitative and/or quantitative characterizations of coating surfaces in association with one or more parameters selected from the group comprising one or more of the components of the coating composition used for producing the respective coating surface, relative and/or absolute amounts of one or more of the said components, manufacturing-process parameters of the coating composition and/or application-process parameters used for creating the coating surfaces;
training a machine learning model on the associations of the coating surface characterizations with the one or more parameters in the database for providing a predictive model (M2, M3) having learned to correlate qualitative and/or quantitative characterizations of one or more coating surfaces with one or more of the parameters stored in association with the respective coating surface characterizations; and
providing a composition-quality-prediction program which comprises the predictive model (M2), the composition-quality-prediction program being configured for using the predictive model (M2) for predicting the properties of a coating surface to be produced from one or more input parameters selected from the group comprising one or more components of a coating composition to be used for producing a coating surface, relative and/or absolute amounts of one or more of the said components, manufacturing-process parameters to be used for preparing the coating composition and/or application-process parameters to be used for creating the coating surface; and/or
providing a composition-specification-prediction program which comprises the predictive model (M3), the composition-specification-prediction program being configured for using the predictive model (M3) for predicting, based on an input specifying at least a desired coating surface characterization and outputting one or more parameters related to a coating composition predicted to generate a coating surface having the input surface characterizations, the one or more output parameters being selected from the group comprising one or more components of the said coating composition, relative and/or absolute amounts of one or more of the said components, manufacturing-process parameters to be used for preparing the coating composition and/or application-process parameters for creating the coating surface, wherein optionally the composition-specification-prediction program is configured for receiving an incomplete coating composition specification and for using the specification for limiting the solution space of the predicted output parameters.

13. The method of clause 12, the method comprising:
providing a plurality of images depicting coating surfaces made from multiple different coating compositions, wherein at least some of the coating surfaces respectively have one or more coating defects of one or more different defect types;
applying a defect-identification program on the images for recognizing patterns in the images, for obtaining the measures of the coating defects represented by the identified patterns in the images and for computing a qualitative and/or quantitative characterization of the coating surfaces depicted in the images, wherein the defect-identification program preferably is the defect-identification program specified in any one of clauses 1-11;
storing the qualitative and/or quantitative characterizations of the coating surfaces in association with one or more parameters related to the coating composition used for creating the coating surface comprising these defects in the database.

14. The method of any one of the previous clauses 12-13, further comprising using of the composition-specification-prediction program for predicting a coating composition specification meeting a desired coating surface characterization provided as input, the using comprising:

providing at least a specification of a desired coating surface characterization as input to the composition-specification-prediction program;

predicting, by the composition-specification-prediction program, a specification of a coating composition adapted to provide a coating surface having the desired surface characteristics, wherein the specification comprises one or more parameters selected from a group comprising: one or more coating composition components, absolute or relative amounts of one or more of the coating composition components, manufacturing process parameters and/or application process parameters;

preferably further comprising outputting the predicted specification of the coating composition to a human and/or inputting the specification of the selected candidate coating composition to a processor which controls a facility (244) for producing and/or testing compositions for coating compositions, wherein the processor drives the facility to produce the input coating composition.

15. The method of any one of the previous clauses 12-14, wherein the training process involves an active learning module, the method further comprising:
   a. performing the training of the machine learning model, preferably a neural network, on the associations of the measures and the coating components in the database for providing the predictive model (M2, M3), where a loss function is minimized for the training,
   b. testing to determine whether the value of the loss function obtained for the predictive model meets a specified criterion,
      whereby selectively in the event that (meaning only in case of that) the criterion is not met, the following steps i-v are carried out:
      i. selection of a candidate coating composition specification (1002) from a plurality of candidate coating composition specifications by the active learning module, the selected candidate composition specification specifying the one of the candidate compositions determined to provide the highest learning effect of the predictive model (M2, M3) regarding the correlation of qualitative and/or quantitative coating surface characterizations and one or more parameters selected from a group comprising coating components, component amounts, manufacturing process parameters and/or application process parameters of the coating composition;
      ii. driving the facility by the computer system for automatically producing the candidate coating composition in accordance with the selected specification, for automatically applying the produced candidate composition on a substrate and for automatically acquiring an image of the surface with the applied coating composition;
      iii. applying the defects-identification program on the image acquired in step ii for computing and storing a qualitative or quantitative characterization of the coating surface depicted in said image in the database, thereby extending the database;
      iv. re-training of the predictive model (M2, M3) on the extended database for providing an improved version of the predictive model,
      v. repeated execution of step b using the improved version of the predictive model,
   c. replacing the predictive model (M2) of the composition-quality-prediction program with the improved version of the predictive model and/or replacing the predictive model (M3) of the composition-specification-prediction program with the improved version of the predictive model.

16. The method of any one of the previous clauses 12-14, wherein the training process involves an active learning module, the method further comprising
   using the active learning module to interactively query the predictive model M2) of the composition-quality-prediction program to perform multiple predictions of the quality of a surface coating to be generated by a coating composition, each prediction being based on a specification of a candidate composition comprising one or more components of a coating composition, relative and/or absolute amounts of one or more of the said components, and/or manufacturing-process parameters to be used for preparing the candidate coating composition and/or application-process parameters to be used for creating the candidate coating surface;
   determining, by the active learning module, a degree of uncertainty of each of the prediction (e.g. by means of a minimum marginal hyperplane method, a loss function, etc.);
   identifying the one or more candidate composition specifications which yielded a prediction result whose degree of uncertainty exceeds a predefined uncertainty threshold;
   producing candidate coating compositions selectively in accordance with the identified candidate coating specifications (but not the other candidate coating composition whose prediction had a sufficient degree of certainty, i.e., an uncertainty level below the threshold), thereby automatically generating new coating compositions,
   applying the new coating compositions to obtain new coating surfaces,
   acquire images of the new coating surfaces;
   performing an image analysis of the acquired images of identifying and/or characterizing surface defects of the new coating surfaces; and
   re-training the composition-quality-prediction program, thereby taking into account also the identified candidate coating specifications and their respectively obtained surface coating defect characteristics for improving the accuracy of the composition-quality-prediction program.

For example, the generation of the new coating compositions and optionally also the generation of the coating surfaces, and optionally also the image acquisition and analysis can be obtained by driving the facility (244) by the computer system to cause the facility to automatically produce the candidate coating compositions accordance with the identified candidate coating specifications (but not the other candidate coating composition whose prediction had a sufficient degree of certainty, i.e., an uncertainty level below the threshold). The facility automatically applies the produced candidate coating composition(s) on a respective substrate. The facility may comprise or be operatively coupled to an image acquisition system. The image acquisition system is used for acquiring an image of the surface with the applied coating composition. The image acquisition system may apply the defects-identification program on the acquired images of the surface coatings of the generated and applied identified candidate coating composition as described herein for embodiments of the invention. Thereby, a qualitative or quantitative characteristics of the new candidate coating surfaces depicted in each image is obtained. These characteristics can be used for re-training and improving the predictive model (M2). A prediction result with a very high degree of uncertainty is interpreted by the active learning module as an indication that the candidate coating composition specification represents a coating composition which is highly unfamiliar to the predictive model, so the predictive model could achieve a high learning effect based on real, empirical and hence reliable data obtained for such a candidate coating composition. The predictive model (M3) of the composition-specification-prediction program can be improved using the active learning module analogously. The only difference is that the input of the predictive model (M3) of the composition-specification-prediction program corresponds to the output of the predictive model (M2) of the composition-quality-prediction program and vice versa, so the two models are challenged based on different candidate input data. In the case of the model (M3), the candidate input data is a specification of desired physical or chemical property of the coating composition, in particular a qualitative and/or quantitative characteristic of a surface coating generated from this coating composition. The other steps and aspects are identical.

17. A system comprising
    a facility (244) for producing and testing compositions for paints, varnishes, printing inks, grinding resins, pigment concentrates or other coating materials, where the facility comprises at least two workstations, where the at least two workstations are connected to one another via a transport system on which self-propelled transport vehicles are able to run for transporting the components of the composition and/or of the composition produced between the workstations, and
    a computer system (224) configured to perform the method of any one of clauses 1-16.

The features of the methods and systems described herein for the above-mentioned clauses can freely be combined with embodiments and examples of the invention as long as they are not mutually exclusive.

LIST OF REFERENCE NUMERALS 102-118 steps
120 data processing system
122 data storage medium
124 defect-identification program
125 digital image
126 processor(s)
130 portable telecommunication device
132 GUI of defect-identification program
134 camera
136 GUI of defect-identification program
140 browser
142 network
144 server computer
146 webserver
150 coating quality control device
152 control panel
154 carrier/transportation belt
156 robotic arm
158 robotic arm
160 light source
162-168 coated samples
170 computer system
204 database
244 facility for manufacturing and/or testing coating compositions
246 main control computer
248 control unit
252 image acquisition unit
254 sample coating unit
246 mixing units
257 analyzers
258 transport unit
400 structure of neural network
402 input data (e.g. vector)
404 layers of neural network
406 output of predictive model
602 training data for predictive model M1
604 Training image for predictive model M1
606 Training image for predictive model M1
608 label with context parameters
610 label with context parameters
612 predictive model M1
614 GUI of defect-identification program
615 camera control module
616 manual label with defects measures and quality characterizations
618 manual label with defects measures and quality characterizations
620 database or image acquisition system
622 test data for predictive model M1
624 test image for predictive model M1
626 test image for predictive model M1
628 label with context parameters
630 label with context parameters
632 computed label with defects measures and quality characterizations
634 computed label with defects measures and quality characterizations
711 untrained predictive model M2
712 trained predictive model M2
714 composition-quality-prediction-program
715 GUI of composition-quality-prediction-program
720 database
721 active learning module
722 test data for M2
728 context parameters
729 computed rheological properties
730 context parameters
731 computed rheological properties
732 computed coating quality/properties
734 computed coating quality/properties
736 output of composition-quality-prediction program
802-816 steps
900 system
902 DBMS
904 database
906 known compositions
908 candidate compositions
910 known composition and properties
912 selected candidate composition
914 selection
916 selected composition
918 properties
944 facility
946 control computer
948 control software
952 analysis unit 954 preparation unit
956 preparation unit
958 transport unit
1000 plot of hyperplane
1002-1009 data points
1016 separation line
1018 area of acceptable coating quality
1020 area of inacceptable coating quality
1202 digital image of coating surface
1204 bubble
1206 bubble
1208 dirt
1210 manually labelled image 1202
1212 manually added labels
1302 digital image of coating surface
1306 foam cavity
1308 foam cavity
1304 automatically generated labels/segment borders of computationally identified cavity defects
1402 quantitative measure of a bubble defect: histogram
1502 illumination angles
1504 image capturing angles

The invention claimed is:

1. A method for one or more of qualitative and quantitative characterization of a coating surface, the method comprising:

providing a defects-identification program configured to recognize coating surface defect types, the defects-identification program comprising a predictive model having been trained on training images acquired within one or more of a predefined distance range and a predefined image acquisition angle range relative to coating surfaces depicted in the training images, providing a data storage medium wherein each of multiple coating surface defect types is stored in association with at least one of a predefined distance range of distances of at least one camera and coating surface and one or more predefined image acquisition angle ranges, the predefined image acquisition angle ranges and distance ranges stored in association with a particular defect type being one or more of angles ranges and distances ranges allowing the acquisition of a digital image of a coating surface that enables the defect identification program to identify said defect type in a digital image of a coating surface;

determining at least one coating surface defect type to be identified;

for each of the at least one determined coating surface defect types to be identified:

automatically identifying at least one of the one of the predefined distance ranges and the one of the one or more predefined image acquisition angle ranges which is stored in association with the determined defect type;

determining, by the defects-identification program, whether at least one camera operatively coupled to the defects-identification program is positioned within one or more of the predefined distance range and the predefined image acquisition angle range relative to a currently presented coating surface, whereby the defects-identification program uses at least one of the identified predefined distance range and the identified predefined image acquisition angle range for the determination whether the camera is positioned within the predefined distance range or image acquisition angle range;

in dependence on the result of the determination, one or more of:

generating a feedback signal indicative of whether adjustment of a position of the at least one camera is required such that the at least one camera is within one or more of the predefined distance range and the predefined image acquisition angle range;

automatically adjusting a relative distance of the at least one camera and the currently presented coating surface such that the position of the at least one camera is within the predefined distance range from the currently presented coating surface; and automatically adjusting an angle of the at least one camera such that the position of the at least one camera is within the predefined image acquisition angle range;

enabling the at least one camera to acquire a digital image of the currently presented coating surface only when the at least one camera is within one or more of the predefined distance range and the predefined image acquisition angle range;

processing the digital image of the currently presented coating surface by the defect-identification program for recognizing coating surface defects; and outputting a characterization of the currently presented coating surface by the defect-identification program, the characterization being computed as a function of recognized coating surface defects.

2. The method of claim 1, comprising:

calculating, by the defect-identification program, a measure for the recognized coating surface defects; wherein the characterization of the currently presented coating surface is computed as a function of one or more of the qualitative and the quantitative characterization of the measure.

3. The method of claim 2, wherein one or more of:

the measure comprises a quantitative measure selected from the group consisting of: the area of a defect, the number of bubbles or depressions indicated in the digital image, one or more of a maximum, minimum and average size of the bubbles, and depressions in the digital image; and the measure comprises a qualitative measure, the qualitative measure comprising one or more of a type of the defect selected from the group consisting of: a cratering defect, an abrasion defect, an adhesion failure defect, an alligatoring defect, a bleeding defect, a blistering defect, a bloom defect, a bridging defect, a bubbling defect, a cathodic disbanding defect, a checking defect, a cissing defect, a cobwebbing defect, a cracking defect, a crazing defect, a crowsfooting defect, a delamination defect, a fading defect, a flaking defect, a grinning defect, a heat defect, an impact defect, an intercoat contamination defect, a mud cracking defect, an orange peeling defect, a peeling defect, a pinholes defect, a rippled coating defect, a runs defect, a rust rashing defect, a rust spotting defect, a rust staining defect, a sags defect, a settlement defect, a skinning defect, a solvent lifting defect, a solvent popping defect, a stress cracking defect, an undercutting defect, and a wrinkling defect.

4. The method of claim 1, wherein the predefined distance range comprises a range of distances between a presented coating surface and the at least one camera which enables the at least one camera to acquire an image having a resolution of at least a predefined minimum resolution, wherein the predefined minimum resolution comprises a coating-defect-type-specific minimum resolution.

5. The method of claim 1, wherein one or more of:
the automatically adjusting of the relative distance of the at least one camera to the currently presented coating surface comprises one or more of automatically modifying the position of the at least one camera and automatically modifying a respective position of a carrier comprising a sample with the currently presented coating surface such that a distance between the at least one camera and the currently presented coating surface lies within the predefined distance range; and
the automatically adjusting of the angle of the at least one camera relative to the currently presented coating surface comprising modifying an orientation of the at least one camera such that the at least one camera is oriented towards the currently presented coating surface at an image acquisition angle lying within the predefined image acquisition angle range.

6. The method of claim 1, wherein:
at least one of the one or more coating surface defect types is stored in association with a predefined illumination angle range, the predefined illumination angle range stored in association with a particular defect type being a range of an illumination angle of a light source relative to a coating surface allowing the acquisition of digital images of coating surfaces that enables the defect identification program to identify the defect type in the digital image of the currently presented coating surface;
and the method further comprising, for each of at least one determined coating surface defect types to be identified:
automatically identifying one of predefined illumination angle ranges stored in association with a determined defect type;
using, by the defects-identification program, an identified predefined illumination angle range for determining whether one or more light sources are positioned relative to the currently presented coating surface such that an illumination angle lies within the identified predefined illumination angle range; and
when the illumination angle of the one or more light sources lies outside of the identified predefined illumination angle range, one or more of:
positioning the one or more light sources and the currently presented coating surface relative to each other such that the illumination angle lies within the identified predefined illumination angle range; and
generating a feedback signal indicating that, or how, adjustment of the positioning of the one or more light sources and the currently presented coating surface relative to each other such that the illumination angle lies within the identified predefined illumination angle range.

7. The method of claim 1, further comprising:
after the positioning of one or more of the currently presented coating surface, the at least one camera, and the one or more light sources relative to each other, using the at least one camera for acquiring the digital image of the currently presented coating surface.

8. The method of claim 1, the processing of the digital image further comprising:
performing, by the defect-identification program, one or more of: a classification of the digital image with respect to one or more of a type and amount of surface defects depicted therein; a semantic segmentation of the digital image based on one or more surface defect types depicted therein; object detection of defect instances in the digital image; and an instance segmentation of the digital image, thereby automatically assigning one or more labels to one or more of a whole of the digital image, to image regions and individual pixels, each label being indicative of the type of a defect identified in the digital image; and
outputting the one or more labels as assigned.

9. The method of claim 1, the defects-identification program being selected from the group consisting of:
a first application program installed on one or more of a stationary data processing system, a portable data processing system, a portable telecommunication device, and a smartphone;
a second application program installed on a portable device or a stationary device specially configured for quality control of coating surfaces;
a third application program installed on a high-throughput facility for one or more of automated, or semi-automated, manufacturing and testing of coatings;
a web application one or more of downloaded and instantiated via a network;
a program executed within one or more of a browser and a JavaScript program;
a server program instantiated on a server computer, the server program being operatively coupled via a network connection to a client program instantiated on a client data processing system, the client program being configured for one or more of: acquiring digital images and providing the digital images via the network to the server program; displaying results provided by the server program.

10. The method of claim 1, wherein the predictive model has learned from training data comprising the training images in a training step performed by a machine learning program configured to recognize patterns in digital images, the machine learning program comprising a neural network.

11. The method of claim 1, further comprising:
generating the predictive model by performing a training step on training data comprising the training images, the training images comprising labels, the labels identifying one or more of locations and types of defects in respective coating surfaces depicted in the training images, the predictive model being trained for recognizing defect types using labeled training images using back propagation.

12. The method of claim 1, wherein each of the training images has assigned additional data being processed in a training step for enabling the predictive model to correlate the additional data with defect types, the additional data comprising one or more of:
a quantitative measure of one or more defects depicted in a training image; and
one or more parameters selected from the group consisting of:
an indication of one or more components of a coating used for generating a coating surface depicting in the training image;
an indication of an absolute or relative amount of one or more of the components of a coating composition; and
one or more manufacturing-process parameters, the manufacturing-process parameters characterizing a process of generating a given coating composition, the process parameters comprising one or more of mixing speed and mixing duration of the coating composition; and one or more application-process parameters, the application-process parameters characterizing a process of applying a respective coating composition on a substrate, the application-process parameters comprising one or more of: an amount of the respective coating composition applied per area of a coating surface; the type of substrate; and a type of application device; and one or more system parameters of an imaging system used for acquiring the training images, the system parameters being selected from the group consisting of: types of one or more light sources used for illuminating coating surfaces, brightness of the one or more light sources, illumination angle, wavelength of the one or more light source, types of one or more cameras used for acquiring digital images of the coating surfaces, one or more image acquisition angles, and one or more positions of the one or more cameras.

13. The method of claim 12, wherein the system parameters comprise at least one or more of: the illumination angle, the image acquisition angle of the at least one camera, and the relative distance of the at least one camera and the currently presented coating surface.

14. A computer system for one or more of qualitative and quantitative characterization of a coating surface, the computer system comprising:

a non-transitory computer-readable storage medium having program instructions for a defects-identification program stored thereon, the defect-identification program being operatively coupled to at least one camera and being configured to recognize coating surface defect types, the defects-identification program comprising a predictive model having been trained on training images acquired within one or more of a predefined distance range and a predefined image acquisition angle range relative to coating surfaces depicted in the training images;

a data storage medium wherein each of multiple coating surface defect types is stored in association with at least one of a predefined distance range of distances of at least one camera and coating surface and one or more predefined image acquisition angle ranges, the predefined image acquisition angle ranges and distance ranges stored in association with a particular defect type being one or more of angles ranges and distances ranges allowing the acquisition of a digital image of a coating surface that enables the defect identification program to identify said defect type in a digital image of a coating surface;

wherein the program instructions are executable by a processor of a computer device to cause the computer device to:

determine at least one coating surface defect type to be identified;

for each of the at least one determined coating surface defect types to be identified:

automatically identify at least one of the one of the predefined distance ranges and the one of the one or more predefined image acquisition angle ranges which is stored in association with the determined defect type;

determine whether the at least one camera is positioned within one or more of the predefined distance range and the predefined image acquisition angle range relative to a currently presented coating surface, whereby the defects-identification program uses at least one of the identified predefined distance range and the identified predefined image acquisition angle range for the determination whether the camera is positioned within the predefined distance range or image acquisition angle range;

in dependence on the result of the determination, one or more of:

generate a feedback signal whether adjustment of a position of the at least one camera is required such that the at least one camera is within one or more of the predefined distance range and the predefined image acquisition angle range;

automatically adjust a relative distance of the at least one camera and the currently presented coating surface such that the position of the at least one camera is within the predefined distance range from the currently presented coating surface; and automatically adjust an angle of the at least one camera such that the position of the at least one camera is within the predefined image acquisition angle range;

enable the at least one camera to acquire a digital image of the currently presented coating surface only when the at least one camera is within one or more of the predefined distance range and the predefined image acquisition angle range;

process the digital image acquired from the enabled at least one camera in order to recognize one or more of the defect types; and output a characterization of the currently presented coating surface, the characterization being computed as a function of coating surface defects recognized by the defect-identification program during the processing.

15. A system comprising one or more of:

the computer system of claim 14;

the at least one camera of the computing system; and a facility for testing compositions for paints, varnishes, printing inks, grinding resins, pigment concentrates or other coating materials, wherein the facility comprises:

at least one workstation configured for applying one or more coating compositions on at least one surface of multiple objects, an automated transport system for transporting the coated objects to an image acquisition and analysis system, wherein the system is configured to use the image acquisition and analysis system for automatically acquiring images of coating surfaces of the multiple objects and for outputting a characterization of the coating surfaces.

* * * * *